United States Patent
Sera

(10) Patent No.: US 11,472,855 B2
(45) Date of Patent: Oct. 18, 2022

(54) RNA-BINDING PROTEIN

(71) Applicant: Takashi Sera, Okayama (JP)

(72) Inventor: Takashi Sera, Okayama (JP)

(*) Notice: Subject to any disclaimer, the term of this patent is extended or adjusted under 35 U.S.C. 154(b) by 164 days.

(21) Appl. No.: 16/494,796

(22) PCT Filed: Mar. 16, 2018

(86) PCT No.: PCT/JP2018/010489
§ 371 (c)(1),
(2) Date: Nov. 22, 2019

(87) PCT Pub. No.: WO2018/169058
PCT Pub. Date: Sep. 20, 2018

(65) Prior Publication Data
US 2020/0095294 A1    Mar. 26, 2020

(30) Foreign Application Priority Data
Mar. 17, 2017 (JP) .............................. JP2017-053093

(51) Int. Cl.
*C07K 14/47* (2006.01)
(52) U.S. Cl.
CPC .................................. *C07K 14/47* (2013.01)
(58) Field of Classification Search
None
See application file for complete search history.

(56) References Cited

U.S. PATENT DOCUMENTS

2013/0323813 A1    12/2013    Filipovska et al.

FOREIGN PATENT DOCUMENTS

| JP | 2013128413 A | 7/2013 |
| WO | 2012068627 A1 | 5/2012 |

OTHER PUBLICATIONS

Abil et al., "Modular assembly of designer PUF protein for specific post-transcriptional regulation of endogenous RNA," Journal of Biological Engineering, vol. 8, No. 7, pp. 1-11 (2014).
Cheong et al., "Engineering RNA sequence specificity of Pumilio repeats," PNAS, vol. 103, No. 37, pp. 13635-13639 (Sep. 12, 2006).
International Preliminary Report on Patentability dated Sep. 17, 2019 in International Application No. PCT/JP2018/010489.
International Search Report and Written Opinion dated Jun. 12, 2018 in International Application No. PCT/JP2018/010489.
Wang et al., "Modular Recognition of RNA by a Human Pumilio-Homology Domain," Cell, vol. 110, pp. 501-512 (2002).
Extended European Search Report dated Dec. 10, 2020 in European Application No. 18767056.7.

*Primary Examiner* — Anand U Desai
(74) *Attorney, Agent, or Firm* — Panitch Schwarze Belisario & Nadel LLP

(57) ABSTRACT

An object of the present invention is to provide a soluble RNA-binding protein having high binding ability. The present invention provides an RNA-binding protein having an amino acid sequence represented by R1'-R1X—R2X—(R5X or R6Y)L-(R5X—R6Y)$_M$-(R5X or R6Y)$_N$—R7X—R8X—R8' wherein each symbol means an amino acid sequence recited in the specification.

10 Claims, 93 Drawing Sheets

Specification includes a Sequence Listing.

[Figure 1]

hPUF_MT (F856A)
R1 : HIMEASQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R4 : HVLKCVKDQNGNHVVQKCIECVQPQSLQFIIDAFKG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (F865A)
R1 : HIMEFSQDQHGSRAIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R4 : HVLKCVKDQNGNHVVQKCIECVQPQSLQFIIDAFKG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 2]

hPUF_MT (F856A/F865A)

R1 : HIMEASQDQHGSRAIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R4 : HVLKCVKDQNGNHVVQKCIECVQPQSLQFIIDAFKG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (F905A)

R1 : HIMEFSQDQHGSRFIQLKLERATPAERQLVFNEILQ
R2 : AAYQLMVDVFGNYVIQKAFEFGSLEQKLALAERIRG
R3 : HVLSLALQMYGCRVIQKALEFIPSDQQNEMVRELDG
R4 : HVLKCVKDQNGNHVVQKCIECVQPQSLQFIIDAFKG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 3]
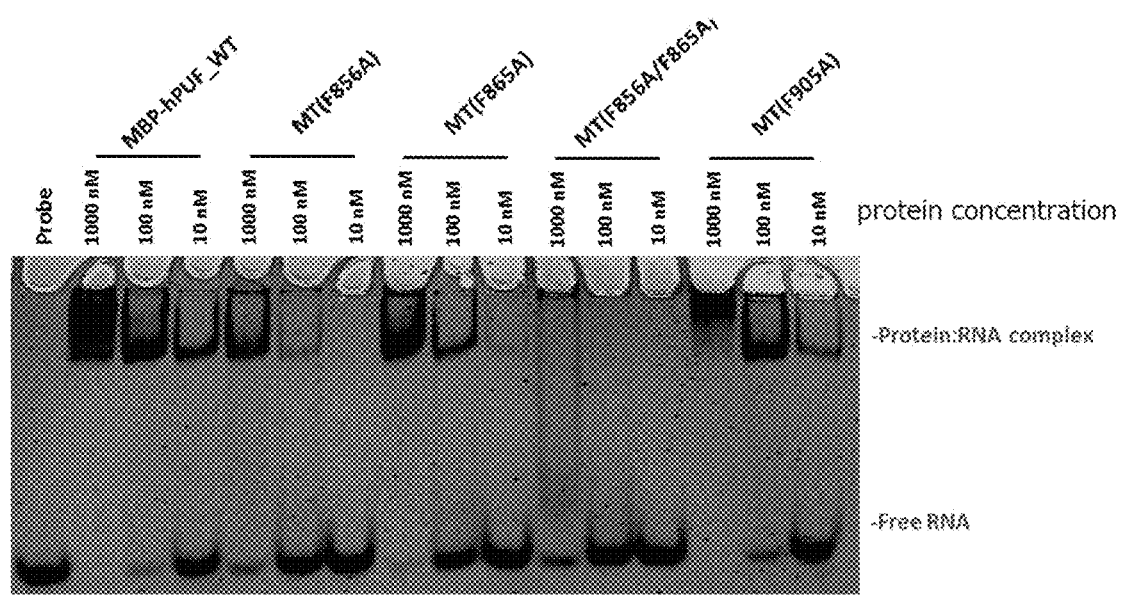

[Figure 4]

hPUF_MT (R3→R5)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R4 : HVLKCVKDQNGNHVVQKCIECVQPQSLQFIIDAFKG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (R4→R6)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 5]
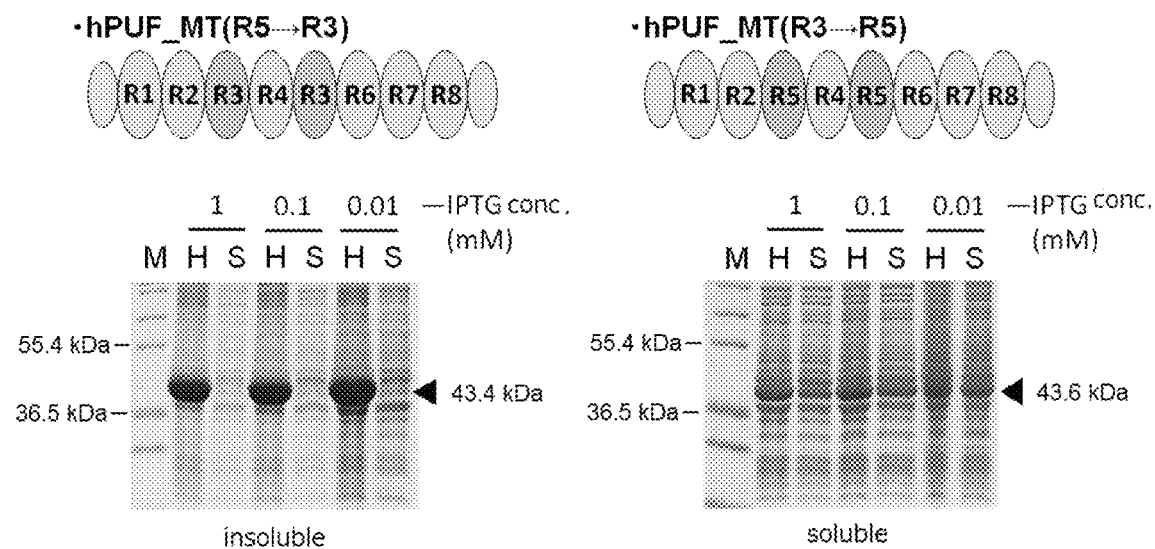
[Figure 6]
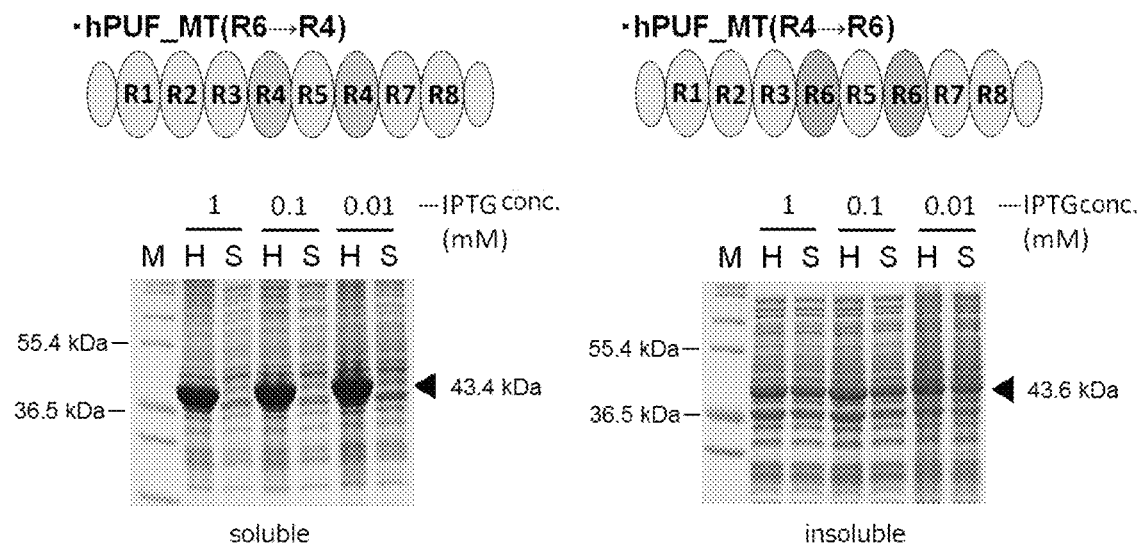

[Figure 7]
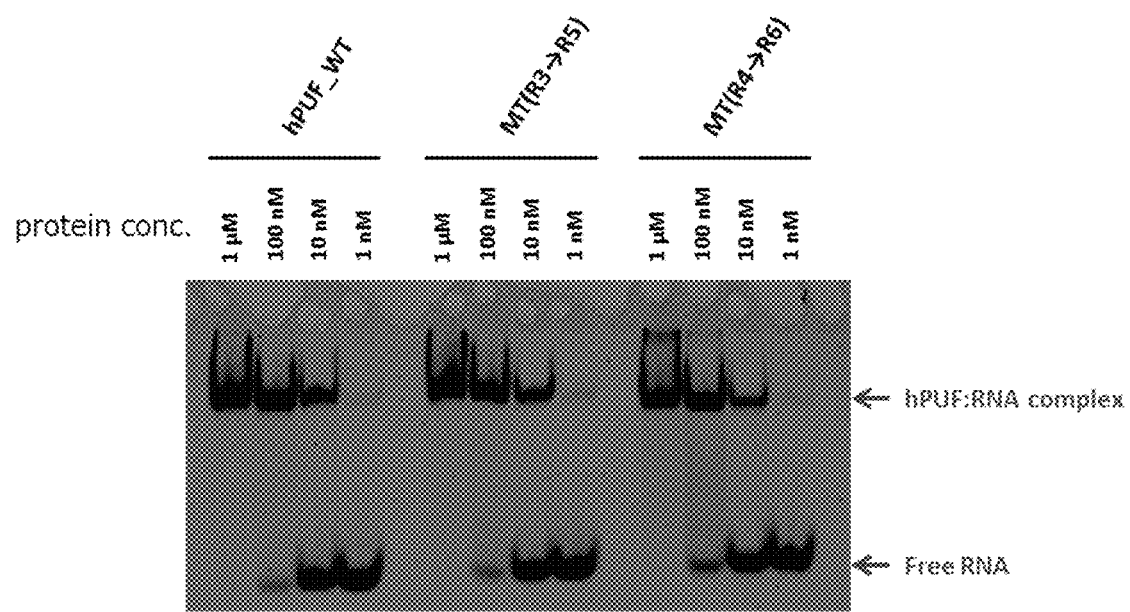

[Figure 8]

hPUF_MT (R3→R5, R4→R5)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R5 : QVFALSTHPYGCRVIQRILEHCLPDQTLPILEELHQ
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (R3→R5, R4→R5_R13H)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R5 : QVFALSTHPYGCHVIQRILEHCLPDQTLPILEELHQ
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 9]

```
hPUF_MT (R4→R6, R5→R6)
R1  : HIMEFSQDQHGSRFIQLKLERATPAERQLVFNEILQ
R2  : AAYQLMVDVFGNYVIQKFFEFGSLEQKLALAERIRG
R3  : HVLSLALQMYGCRVIQKALEFIPSDQQNEMVRELDG
R6  : HTEQLVQDQYGNYVIQHVLEHGRPEDKSKIVAEIRG
R6  : HTEQLVQDQYGNYVIQHVLEHGRPEDKSKIVAEIRG
R6  : HTEQLVQDQYGNYVIQHVLEHGRPEDKSKIVAEIRG
R7  : NVLVLSQHKFASNVVEKCVTHASRTERAVLIDEVCTMNDGPHS
R8  : ALYTMMKDQYANYVVQKMIDVAEPGQRKIVMHKIRP hPUF_MT (R4→R6, R5→R6_Y13R)
R1  : HIMEFSQDQHGSRFIQLKLERATPAERQLVFNEILQ
R2  : AAYQLMVDVFGNYVIQKFFEFGSLEQKLALAERIRG
R3  : HVLSLALQMYGCRVIQKALEFIPSDQQNEMVRELDG
R6  : HTEQLVQDQYGNYVIQHVLEHGRPEDKSKIVAEIRG
R6  : HTEQLVQDQYGNRVIQHVLEHGRPEDKSKIVAEIRG
R6  : HTEQLVQDQYGNYVIQHVLEHGRPEDKSKIVAEIRG
R7  : NVLVLSQHKFASNVVEKCVTHASRTERAVLIDEVCTMNDGPHS
R8  : ALYTMMKDQYANYVVQKMIDVAEPGQRKIVMHKIRP
```

[Figure 10]
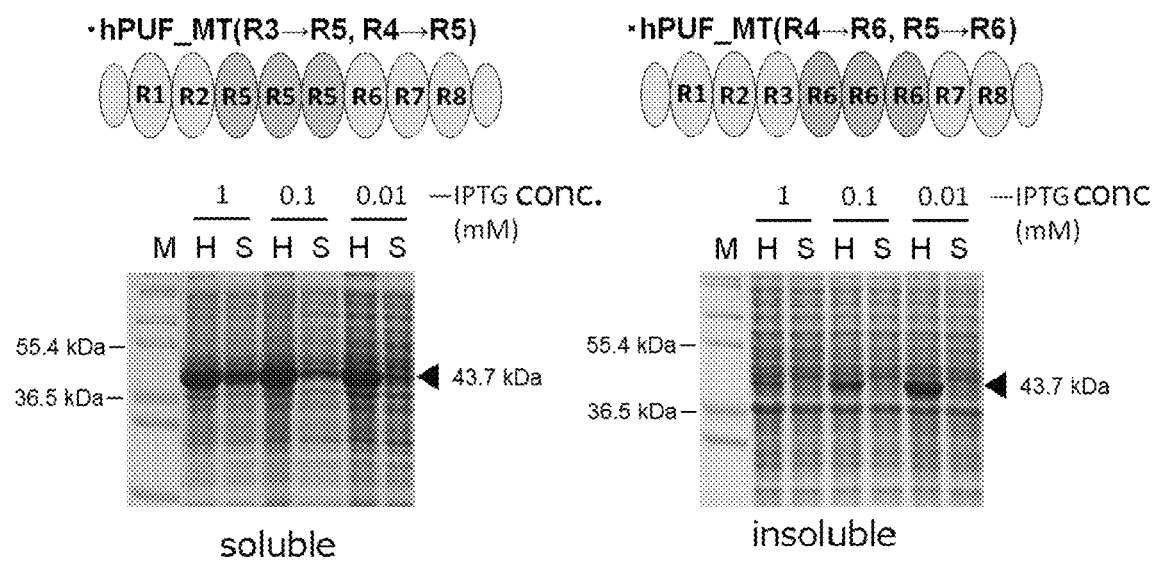
[Figure 11]
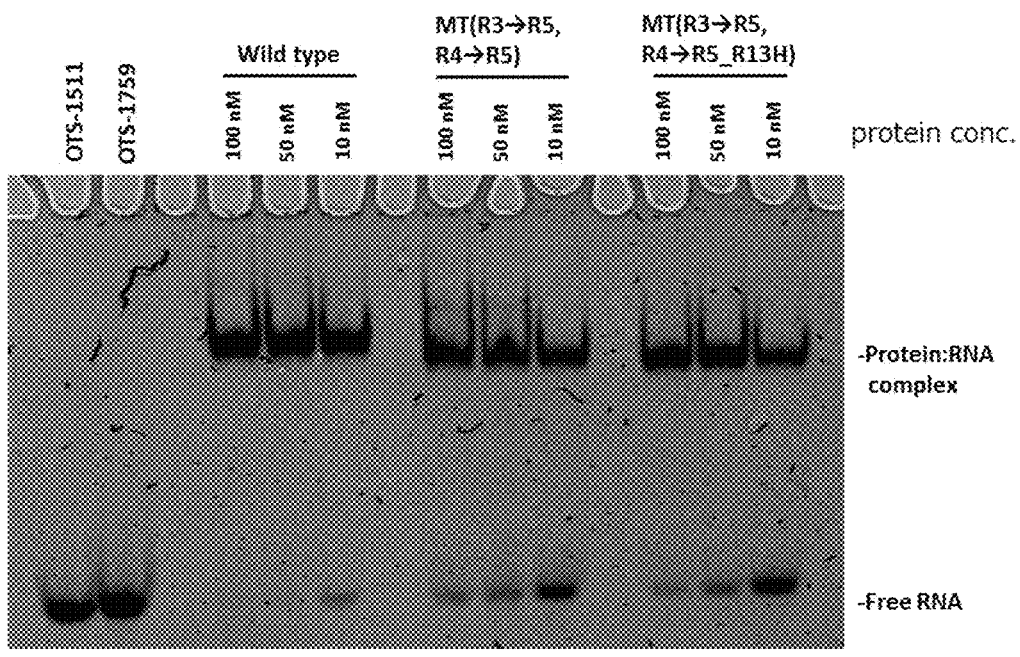

[Figure 12]

hPUF_MT (R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (1-6-5-6-5-6-7-8)
R1 : HIMEFSQDQHGSRFIQLKLERATPAERQLVFNEILQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

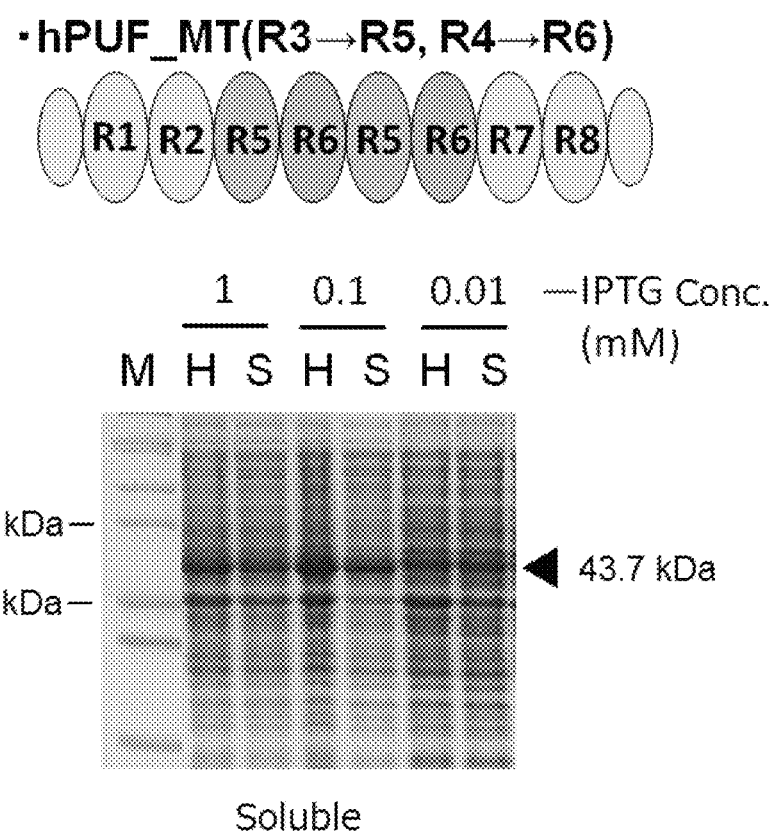
[Figure 13]

[Figure 14]
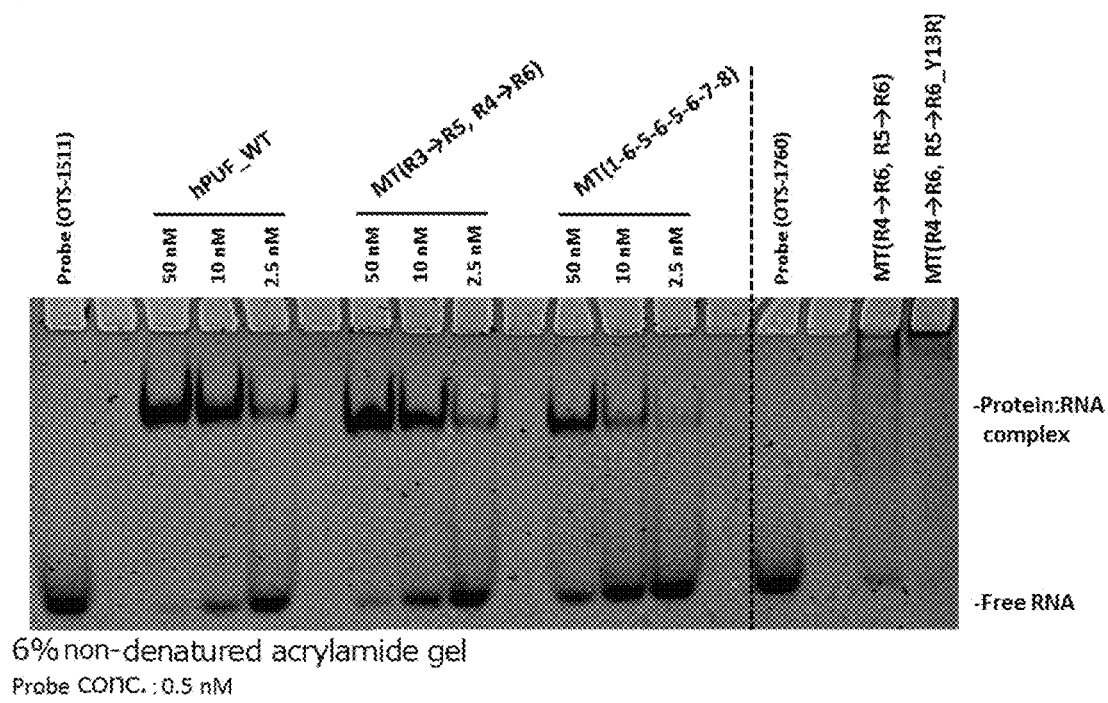

[Figure 15]

hPUF_MT (1-2-5-6-5-6-5_ILQ-8)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEEILQ
R8 : ALYTMMKDQYANYVVQKMIDVAEPGQRKIVMHKIRP hPUF_MT (1-6-5-6-5-6-5-6_IRP)
R1 : HIMEFSQDQHGSRFIQLKLERATPAERQLVFNEILQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : QVFALSTHPYGCRVIQRILEHCLPDQTLPILEELHQ
R6 : HTEQLVQDQYGNYVIQHVLEHGRPEDKSKIVAEIRP

[Figure 16]
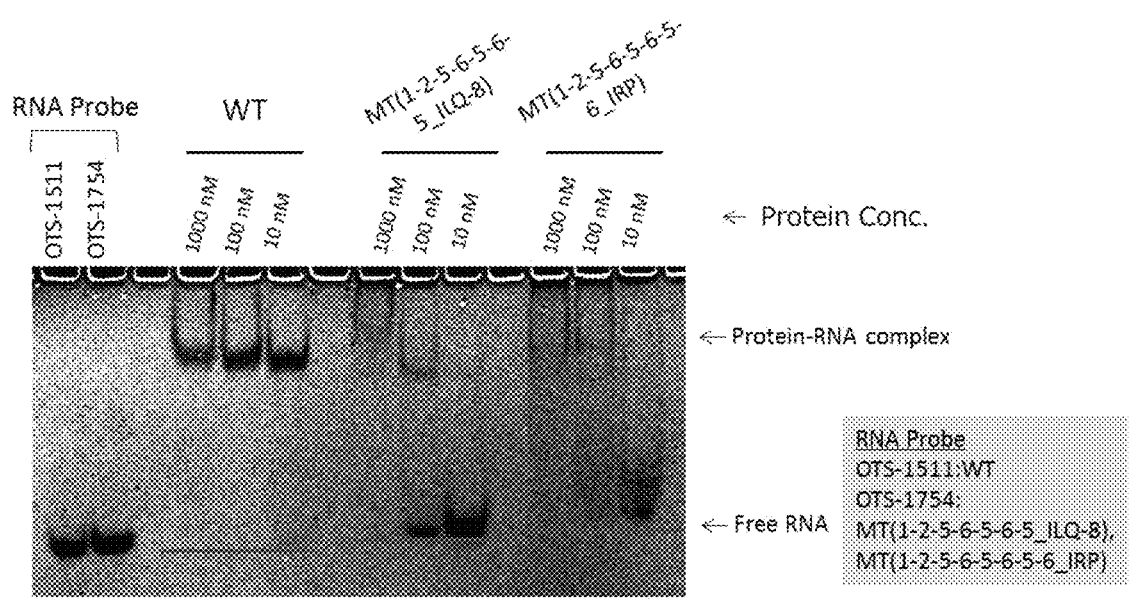

[Figure 17]

```
hPUF_MT (1-5-5-5-5-6-7-8)
R1  : HIMEFSQDQHGSRFIQLKLERATPAERQLVFNEILQ
R5  : QVFALSTHPYGCRVIQRILEHCLPDQTLPILEELHQ
R5  : QVFALSTHPYGCRVIQRILEHCLPDQTLPILEELHQ
R5  : QVFALSTHPYGCRVIQRILEHCLPDQTLPILEELHQ
R5  : QVFALSTHPYGCRVIQRILEHCLPDQTLPILEELHQ
R6  : HTEQLVQDQYGNYVIQHVLEHGRPEDKSKIVAEIRG
R7  : NVLVLSQHKFASNVVEKCVTHASRTERAVLIDEVCTMNDGPHS
R8  : ALYTMMKDQYANYVVQKMIDVAEPGQRKIVMHKIRP hPUF_MT (1-2-5-6-5-6-5-6-7-8)
R1  : HIMEFSQDQHGSRFIQLKLERATPAERQLVFNEILQ
R2  : AAYQLMVDVFGNYVIQKFFEFGSLEQKLALAERIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R7  : NVLVLSQHKFASNVVEKCVTHASRTERAVLIDEVCTMNDGPHS
R8  : ALYTMMKDQYANYVVQKMIDVAEPGQRKIVMHKIRP
```

[Figure 18]

```
hPUF_MT (1-5-5-5-5-5-7-8)
R1  : HIMEFSQDQHGSRFIQLKLERATPAERQLVFNEILQ
R5  : QVFALSTHPYGCRVIQRILEHCLPDQTLPILEELHQ
R5  : QVFALSTHPYGCRVIQRILEHCLPDQTLPILEELHQ
R5  : QVFALSTHPYGCHVIQRILEHCLPDQTLPILEELHQ
R5  : QVFALSTHPYGCRVIQRILEHCLPDQTLPILEELHQ
R5  : QVFALSTHPYGCRVIQRILEHCLPDQTLPILEELHQ
R7  : NVLVLSQHKFASNVVEKCVTHASRTERAVLIDEVCTMNDGPHS
R8  : ALYTMMKDQYANYVVQKMIDVAEPGQRKIVMHKIRP
```

[Figure 19]

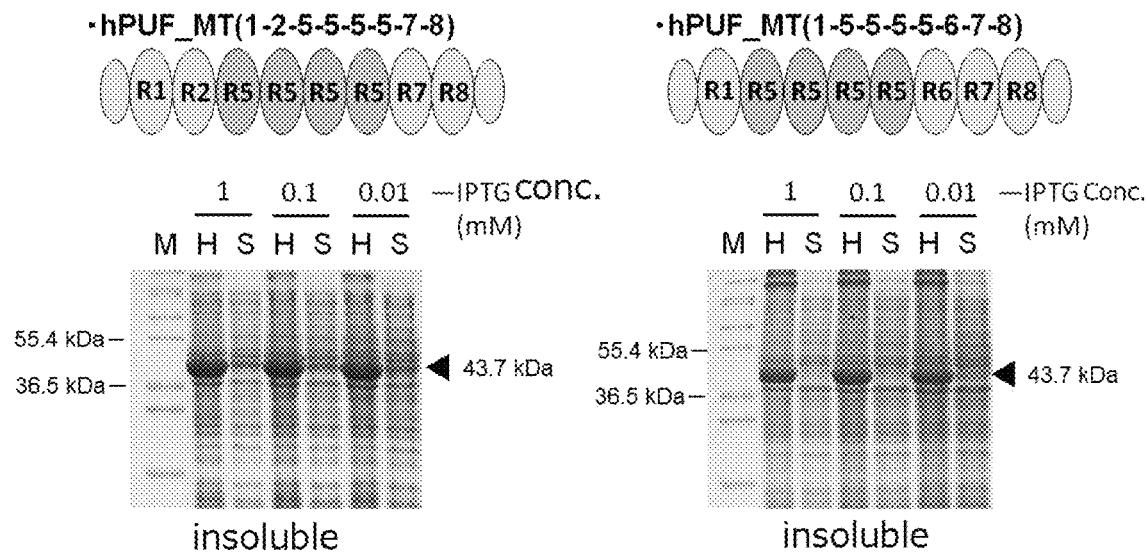

[Figure 20]
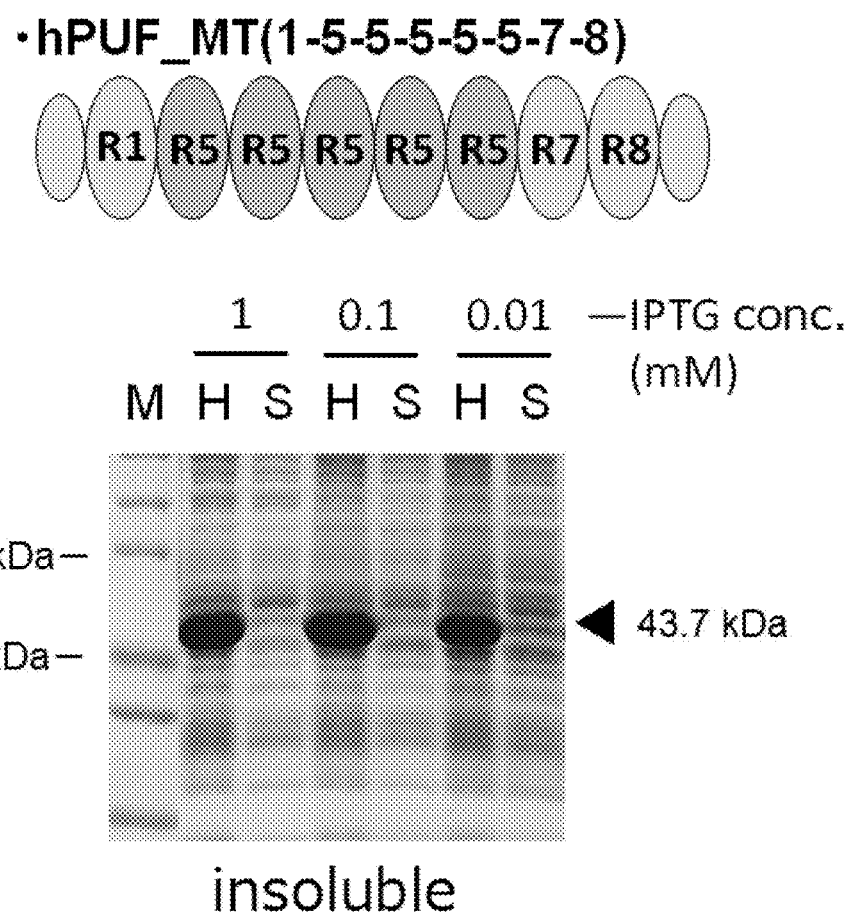

[Figure 21]
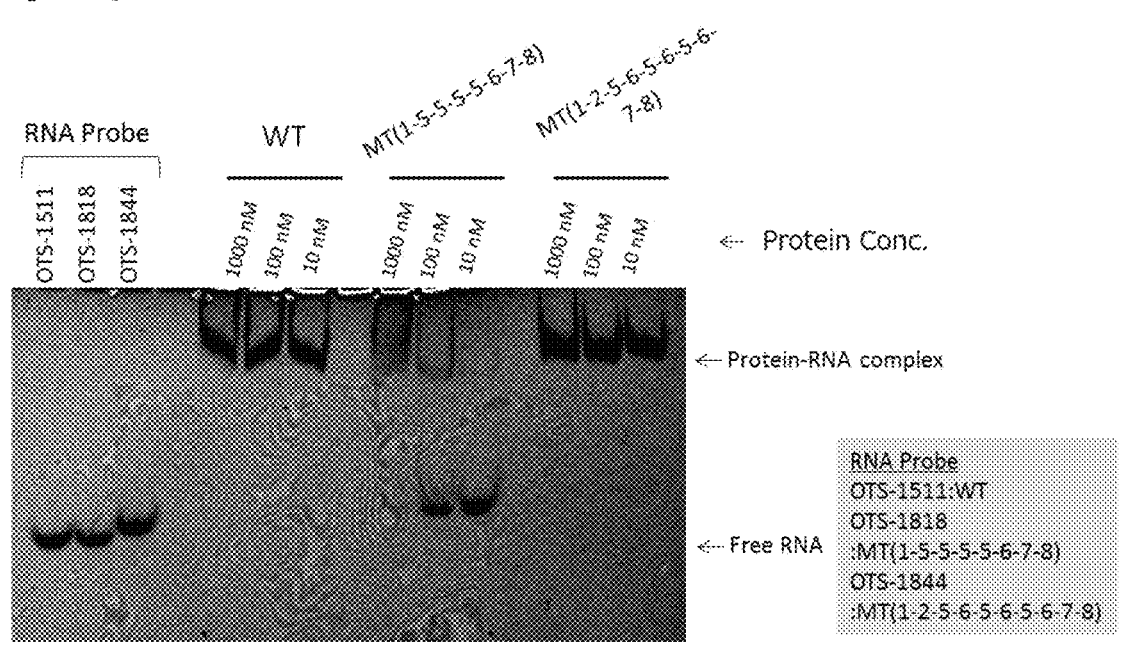

[Figure 22]

hPUF_MT (R7→R5)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R4 : HVLKCVKDQNGNHVVQKCIECVQPQSLQFIIDAFKG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEEILQ
R8 : ALYTMMKDQYANYVVQKMIDVAEPGQRKIVMHKIRP hPUF_MT (R7_ILQ)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R4 : HVLKCVKDQNGNHVVQKCIECVQPQSLQFIIDAFKG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEILQ
R8 : ALYTMMKDQYANYVVQKMIDVAEPGQRKIVMHKIRP

[Figure 23]

hPUF_MT (R7_IRG)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R4 : HVLKCVKDQNGNHVVQKCIECVQPQSLQFIIDAFKG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEIRG
R8 : ALYTMMKDQYANYVVQKMIDVAEPGQRKIVMHKIRP

[Figure 24]

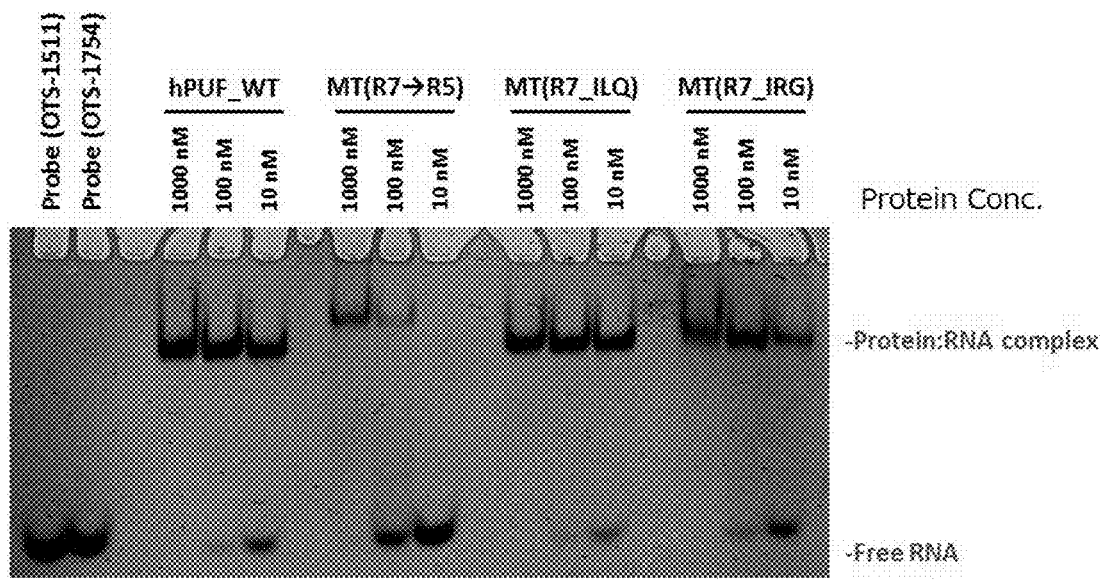

[Figure 25]
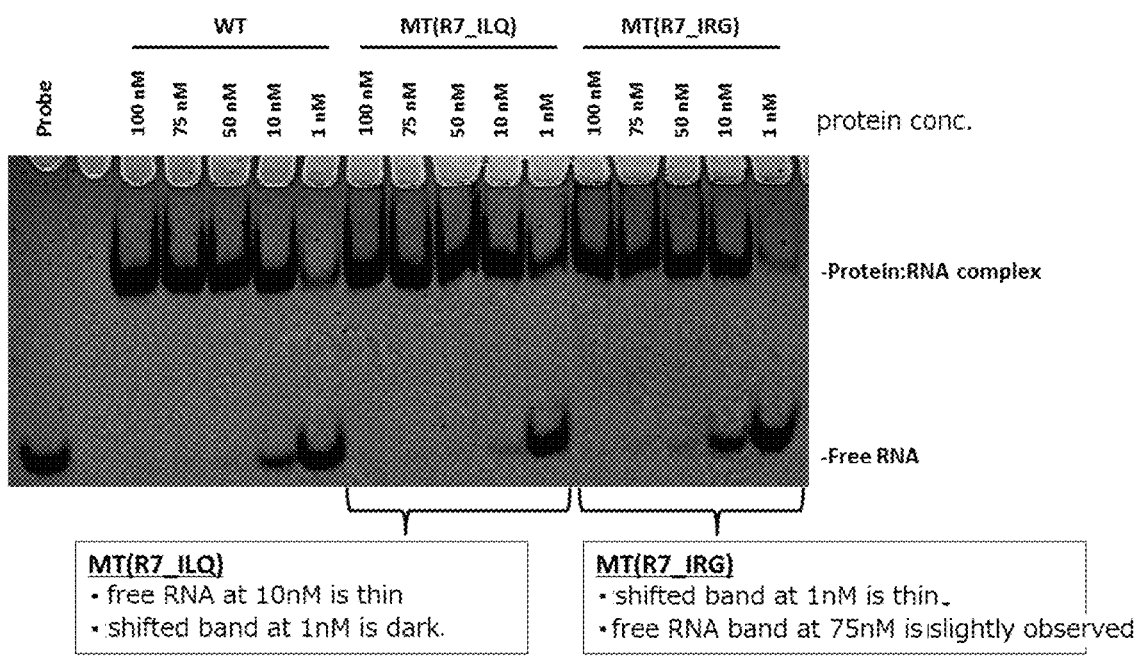

[Figure 26]

hPUF_MT (R7→R5)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R4 : HVLKCVKDQNGNHVVQKCIECVQPQSLQFIIDAFKG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEEILQ
R8 : ALYTMMKDQYANYVVQKMIDVAEPGQRKIVMHKIRP hPUF_MT (R8→R5)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R4 : HVLKCVKDQNGNHVVQKCIECVQPQSLQFIIDAFKG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R5 : QVFALSTHPYGCRVIQRILEHCLPDQTLPILEELHQ

[Figure 27]
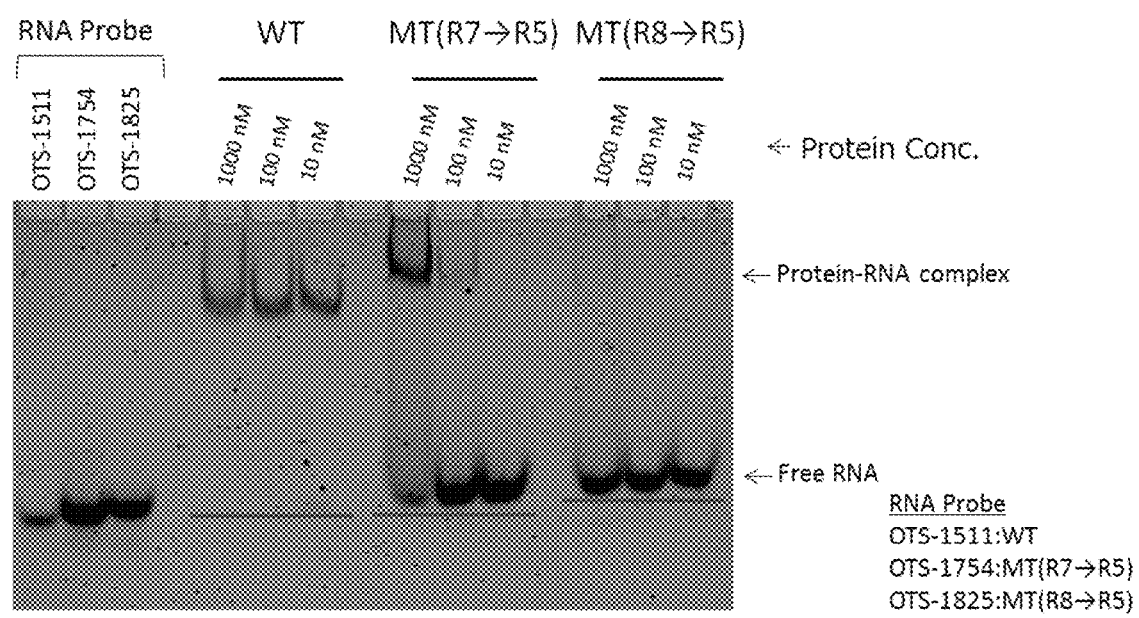

[Figure 28]

```
hPUF_MT (R3→RC, R4→RC, R5→RC)
R1  : HIMEFSQDQHGSRFIQLKLERATPAERQLVFNEILQ
R2  : AAYQLMVDVFGNYVIQKFFEFGSLEQKLALAERIRG
R3  : HVLQLSQDQYGCRVIQKILEHATPEQRQLIVDEIRG
R4  : HVLQLSQDQYGCRVIQKILEHATPEQRQLIVDEIRG
R5  : HVLQLSQDQYGCRVIQKILEHATPEQRQLIVDEIRG
R6  : HTEQLVQDQYGNYVIQHVLEHGRPEDKSKIVAEIRG
R7  : NVLVLSQHKFASNVVEKCVTHASRTERAVLIDEVCTMNDGPHS
R8  : ALYTMMKDQYANYVVQKMIDVAEPGQRKIVMHKIRP hPUF_MT (R3→RC2, R4→RC2, R5→RC2)
R1  : HIMEFSQDQHGSRFIQLKLERATPAERQLVFNEILQ
R2  : AAYQLMVDVFGNYVIQKFFEFGSLEQKLALAERIRG
R3  : HVLALSQDQYGCRVIQKILEHALPDQRLLIVEEIRG
R4  : HVLALSQDQYGCRVIQKILEHALPDQRLLIVEEIRG
R5  : HVLALSQDQYGCRVIQKILEHALPDQRLLIVEEIRG
R6  : HTEQLVQDQYGNYVIQHVLEHGRPEDKSKIVAEIRG
R7  : NVLVLSQHKFASNVVEKCVTHASRTERAVLIDEVCTMNDGPHS
R8  : ALYTMMKDQYANYVVQKMIDVAEPGQRKIVMHKIRP
```

[Figure 29]
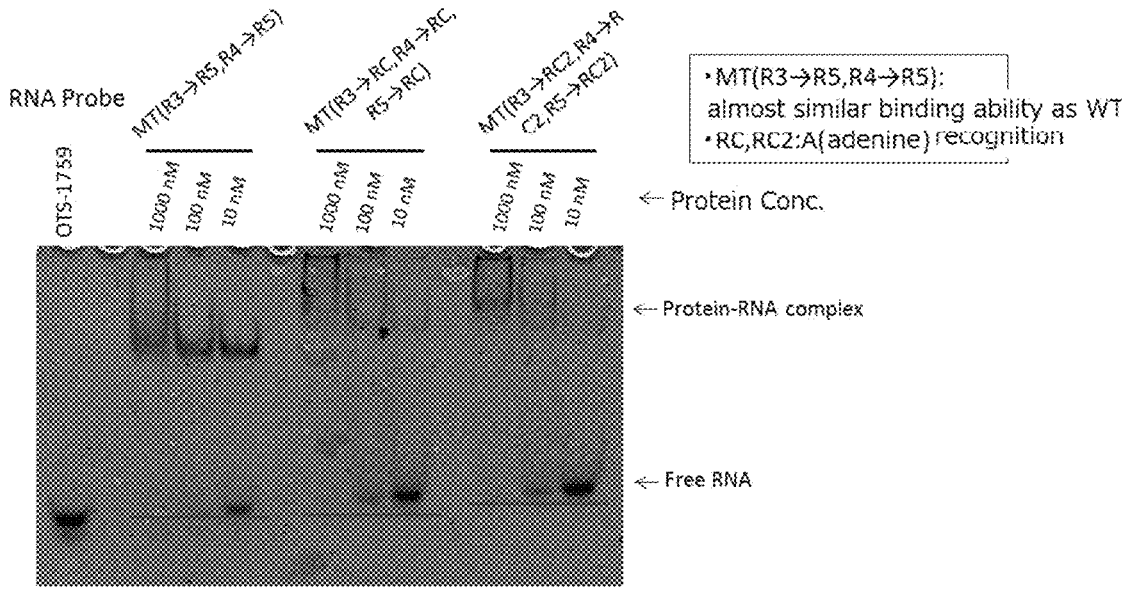
[Figure 30]
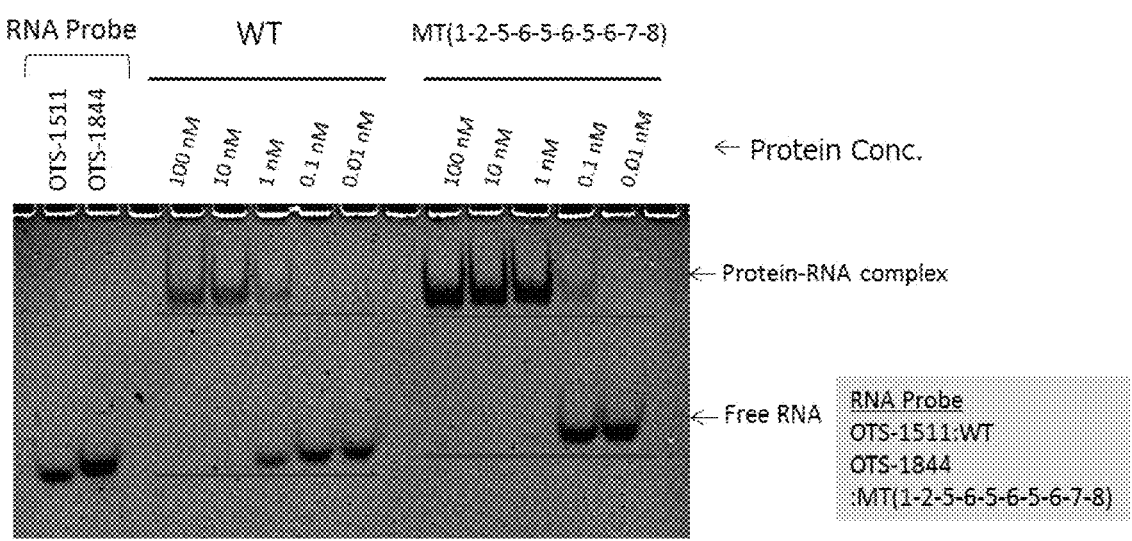

[Figure 31]

```
hPUF_MT (1-2-5-6-5-6-5-6-5-6-7-8)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP
```

[Figure 32]

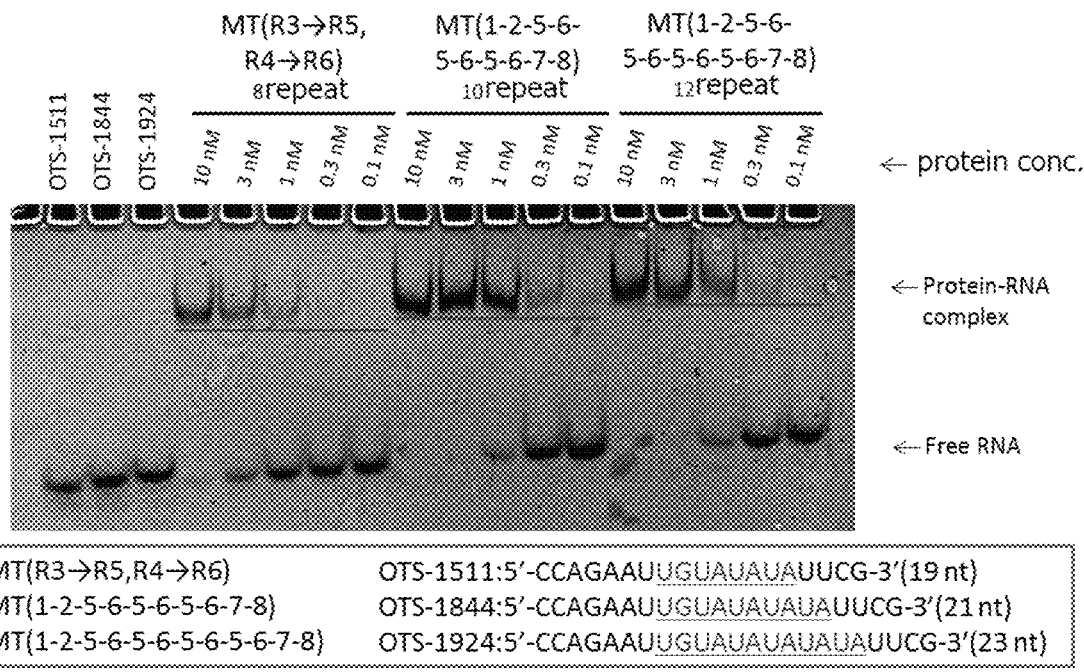

[Figure 33]

```
hPUF_MT (1-2-5-6-5-6-5-6-5-6-5-6-7-8)
R1  : HIMEFSQDQHGSRFIQLKLERATPAERQLVFNEILQ
R2  : AAYQLMVDVFGNYVIQKFFEFGSLEQKLALAERIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R7  : NVLVLSQHKFASNVVEKCVTHASRTERAVLIDEVCTMNDGPHS
R8  : ALYTMMKDQYANYVVQKMIDVAEPGQRKIVMHKIRP
```

[Figure 34]

```
hPUF_MT (1-2-5-6-5-6-5-6-5-6-5-6-5-6-7-8)
R1  : HIMEFSQDQHGSRFIQLKLERATPAERQLVFNEILQ
R2  : AAYQLMVDVFGNYVIQKFFEFGSLEQKLALAERIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R7  : NVLVLSQHKFASNVVEKCVTHASRTERAVLIDEVCTMNDGPHS
R8  : ALYTMMKDQYANYVVQKMIDVAEPGQRKIVMHKIRP
```

[Figure 35]
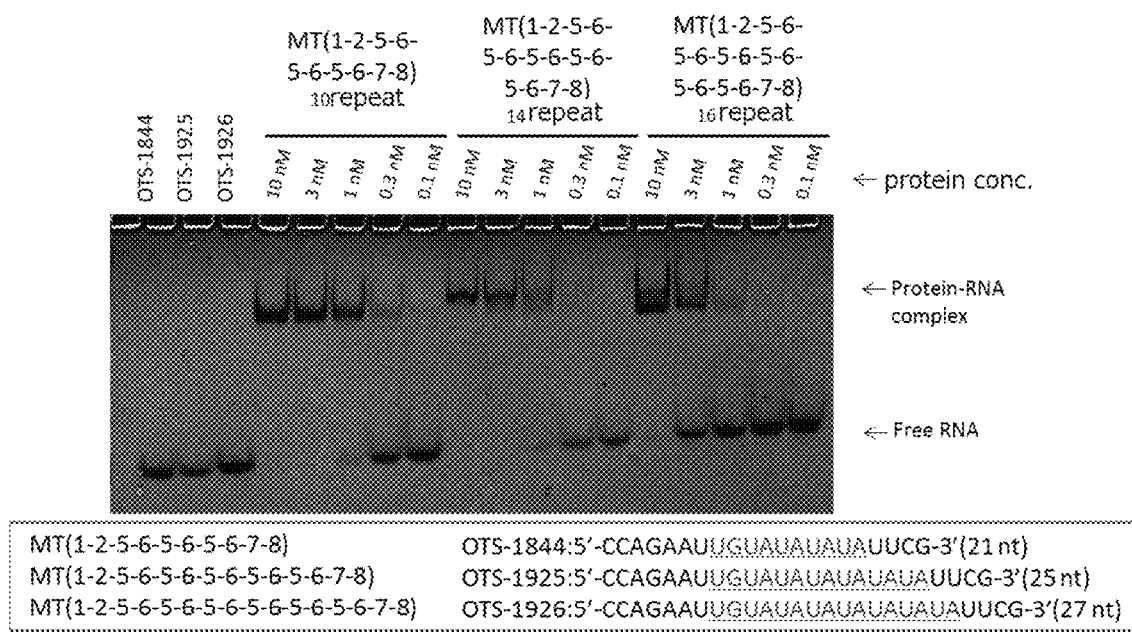

[Figure 36]

hPUF_MT (R3→R5, R4→R5)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R5 : QVFALSTHPYGCRVIQRILEHCLPDQTLPILEELHQ
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (R3→R5_C12N, R4→R5_C12N, R5_C12N)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGNRVIQRILEHCLPDQTLPILEELHQ
R5 : QVFALSTHPYGNRVIQRILEHCLPDQTLPILEELHQ
R5 : QVFALSTHPYGNRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 37]

hPUF_MT (R3→R5_C12S, Q16E,  R4→R5_C12S, Q16E,  R5_C12S, Q16E)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIERILEHCLPDQTLPILEELHQ
R5 : QVFALSTHPYGSRVIERILEHCLPDQTLPILEELHQ
R5 : QVFALSTHPYGSRVIERILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (R3→R5_C12S, Q16R,  R4→R5_C12S, Q16R,  R5_C12S, Q16R)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIRRILEHCLPDQTLPILEELHQ
R5 : QVFALSTHPYGSRVIRRILEHCLPDQTLPILEELHQ
R5 : QVFALSTHPYGSRVIRRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 38]

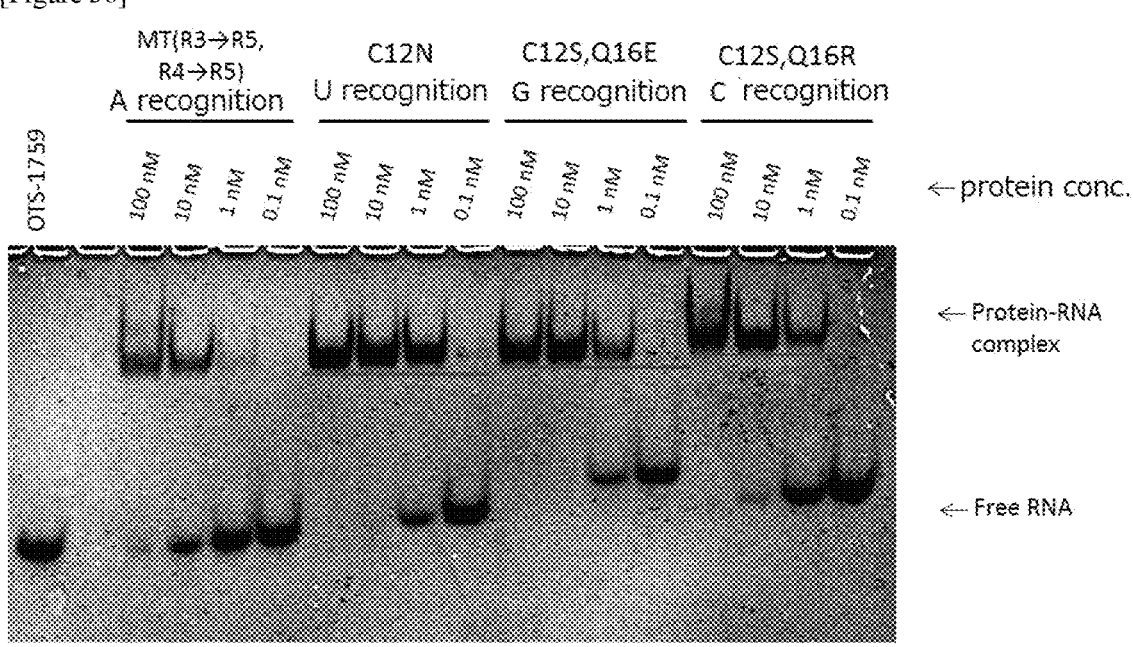

[Figure 39]
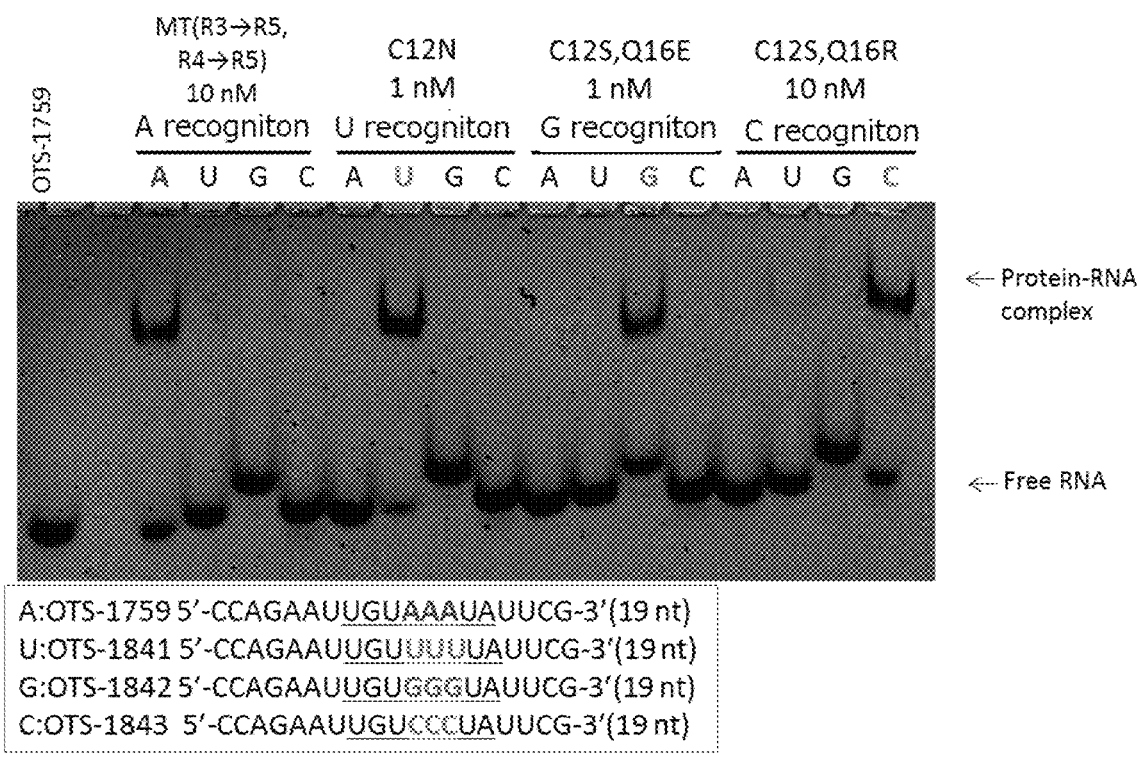

[Figure 40]

hPUF_MT (R4→R6)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (R4→R6_N12C, R6_N12C)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R6 : HTEQLVQDQYGCYVIQHVLEHGRPEDKSKIVAEIRG
R5 : QVFALSTHPYGCRVIQRILEHCLPDQTLPILEELHQ
R6 : HTEQLVQDQYGCYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 41]

hPUF_MT (R4→R6_N12S, Q16E, R6_N12S, Q16E)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R6 : HTEQLVQDQYGSYVIEHVLEHGRPEDKSKIVAEIRG
R5 : QVFALSTHPYGCRVIQRILEHCLPDQTLPILEELHQ
R6 : HTEQLVQDQYGSYVIEHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (R4→R6_N12S, Q16R, R6_N12S, Q16R)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R6 : HTEQLVQDQYGSYVIRHVLEHGRPEDKSKIVAEIRG
R5 : QVFALSTHPYGCRVIQRILEHCLPDQTLPILEELHQ
R6 : HTEQLVQDQYGSYVIRHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 42]
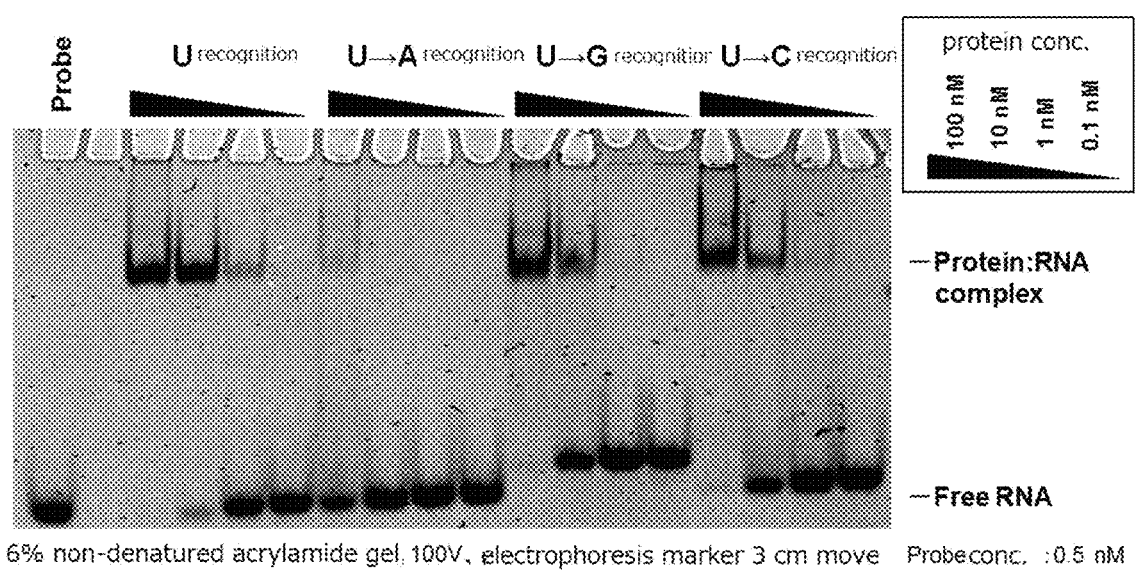

[Figure 43]
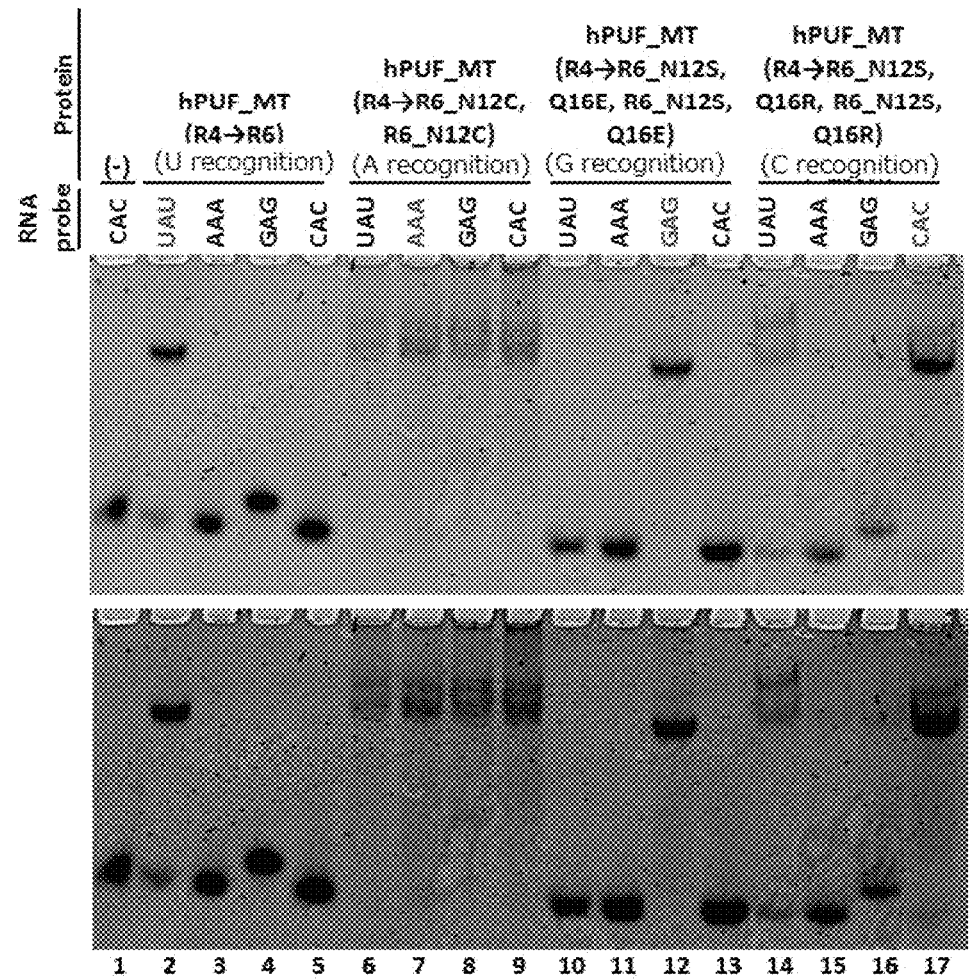

[Figure 44]

hPUF_MT (R5_R13K)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R4 : HVLKCVKDQNGNHVVQKCIECVQPQSLQFIIDAFKG
R5 : QVFALSTHPYGCKVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (R6_Y13F)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R4 : HVLKCVKDQNGNHVVQKCIECVQPQSLQFIIDAFKG
R5 : QVFALSTHPYGCRVIQRILEHCLPDQTLPILEELHQ
R6 : HTEQLVQDQYGNFVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 45]

hPUF_MT (R6_Y13H)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R4 : HVLKCVKDQNGNHVVQKCIECVQPQSLQFIIDAFKG
R5 : QVFALSTHPYGCRVIQRILEHCLPDQTLPILEELHQ
R6 : HTEQLVQDQYGNHVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (R6_Y13W)
R1 : HIMEFSQDQHGSRFIQLKLERATPAERQLVFNEILQ
R2 : AAYQLMVDVFGNYVIQKFFEFGSLEQKLALAERIRG
R3 : HVLSLALQMYGCRVIQKALEFIPSDQQNEMVRELDG
R4 : HVLKCVKDQNGNHVVQKCIECVQPQSLQFIIDAFKG
R5 : QVFALSTHPYGCRVIQRILEHCLPDQTLPILEELHQ
R6 : HTEQLVQDQYGNWVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 46]
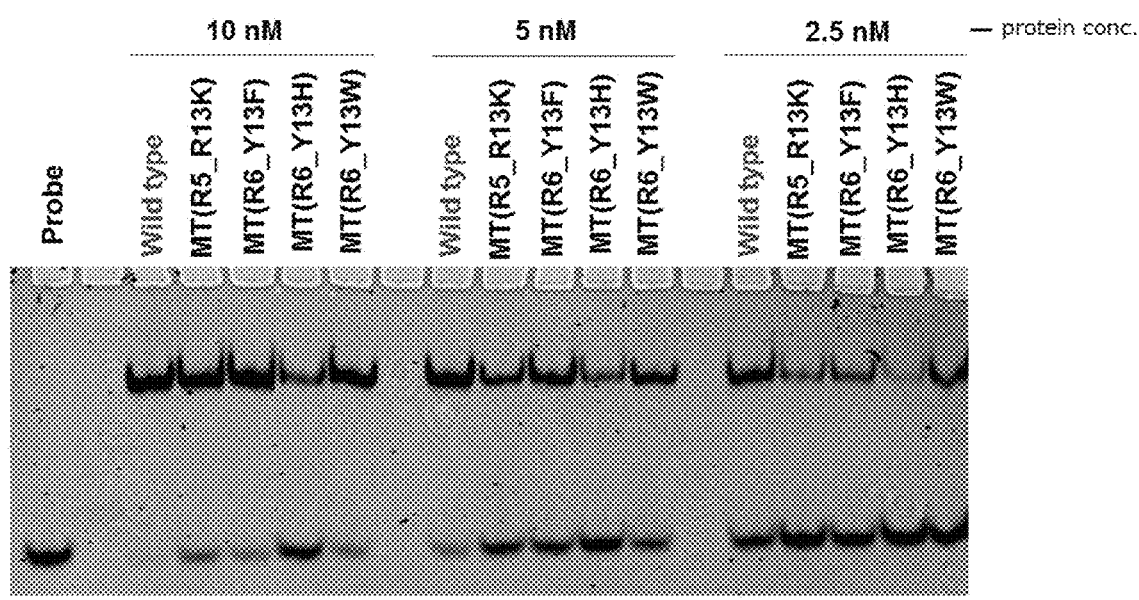

[Figure 47]

hPUF_MT (R3→R5, R4→R5)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R5 : QVFALSTHPYGCRVIQRILEHCLPDQTLPILEELHQ
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (R3→R5, R4→R5_R13H, R5_R13H)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R5 : QVFALSTHPYGCHVIQRILEHCLPDQTLPILEELHQ
R5 : QVFALSTHPYGCHVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 48]

```
hPUF_MT (R3→R5, R4→R5_R13F, R5_R13F)
R1  : HIMEFSQDQHGSRFIQLKLERATPAERQLVFNEILQ
R2  : AAYQLMVDVFGNYVIQKFFEFGSLEQKLALAERIRG
R5  : QVFALSTHPYGCRVIQRILEHCLPDQTLPILEELHQ
R5  : QVFALSTHPYGCFVIQRILEHCLPDQTLPILEELHQ
R5  : QVFALSTHPYGCFVIQRILEHCLPDQTLPILEELHQ
R6  : HTEQLVQDQYGNYVIQHVLEHGRPEDKSKIVAEIRG
R7  : NVLVLSQHKFASNVVEKCVTHASRTERAVLIDEVCTMNDGPHS
R8  : ALYTMMKDQYANYVVQKMIDVAEPGQRKIVMHKIRP hPUF_MT (R3→R5, R4→R5_R13Y, R5_R13Y)
R1  : HIMEFSQDQHGSRFIQLKLERATPAERQLVFNEILQ
R2  : AAYQLMVDVFGNYVIQKFFEFGSLEQKLALAERIRG
R5  : QVFALSTHPYGCRVIQRILEHCLPDQTLPILEELHQ
R5  : QVFALSTHPYGCYVIQRILEHCLPDQTLPILEELHQ
R5  : QVFALSTHPYGCYVIQRILEHCLPDQTLPILEELHQ
R6  : HTEQLVQDQYGNYVIQHVLEHGRPEDKSKIVAEIRG
R7  : NVLVLSQHKFASNVVEKCVTHASRTERAVLIDEVCTMNDGPHS
R8  : ALYTMMKDQYANYVVQKMIDVAEPGQRKIVMHKIRP
```

[Figure 49]

hPUF_MT (R3→R5, R4→R5_R13W, R5_R13W)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R5 : QVFALSTHPYGCWVIQRILEHCLPDQTLPILEELHQ
R5 : QVFALSTHPYGCWVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 50]

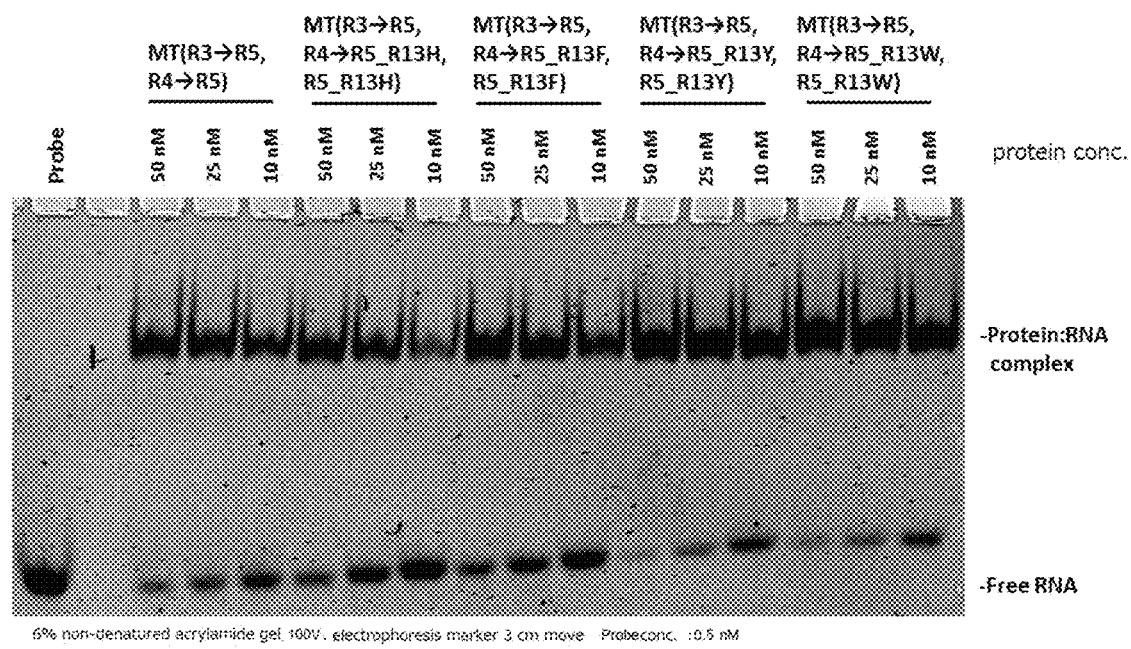

[Figure 51]

```
hPUF_MT (R3→R5, R4→R5_R13K, R5_R13K)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQKILEHCLPDQTLPILEELHQ
R5 : QVFALSTHPYGCKVIQKILEHCLPDQTLPILEELHQ
R5 : QVFALSTHPYGCKVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP
```

[Figure 52]

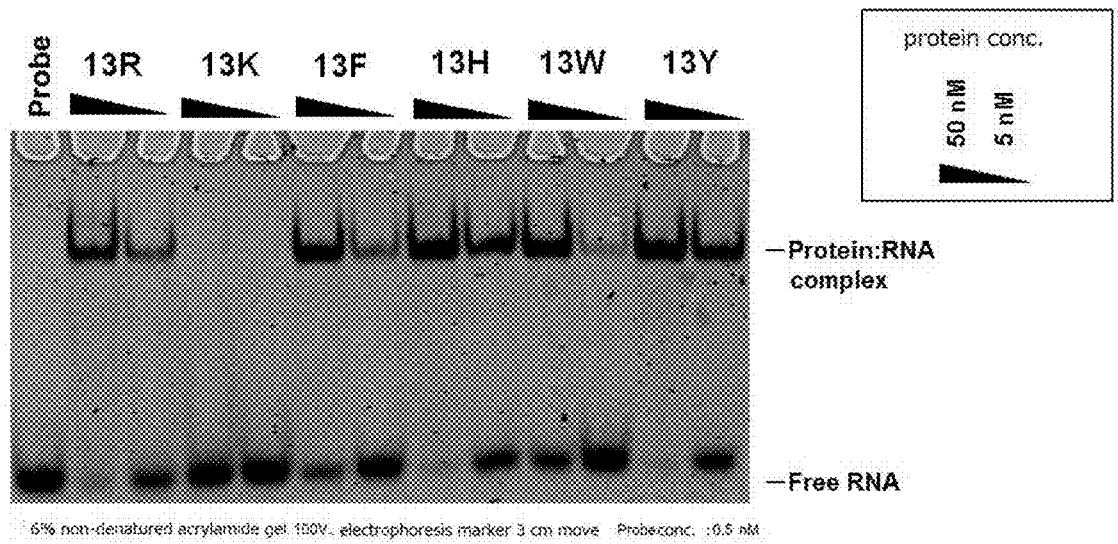

[Figure 53]

```
hPUF_MT (R5:A_13R)₃(R6:C_13Y)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGSYVIRHVLEHGRPEDKSKIVAEIRG
R5 : QVFALSTHPYGCRVIQRILEHCLPDQTLPILEELHQ
R6 : HTEQLVQDQYGSYVIRHVLEHGRPEDKSKIVAEIRG
R5 : QVFALSTHPYGCRVIQRILEHCLPDQTLPILEELHQ
R6 : HTEQLVQDQYGSYVIRHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (R5:A_13R)₃(R6:C_13R)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGSRVIRHVLEHGRPEDKSKIVAEIRG
R5 : QVFALSTHPYGCRVIQRILEHCLPDQTLPILEELHQ
R6 : HTEQLVQDQYGSRVIRHVLEHGRPEDKSKIVAEIRG
R5 : QVFALSTHPYGCRVIQRILEHCLPDQTLPILEELHQ
R6 : HTEQLVQDQYGSRVIRHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP
```

[Figure 54]

hPUF_MT (R5:A_13R) (R5:A_13Y)$_2$ (R6:C_13Y)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGSYVIRHVLEHGRPEDKSKIVAEIRG
R5 : QVFALSTHPYGCYVIQRILEHCLPDQTLPILEELHQ
R6 : HTEQLVQDQYGSYVIRHVLEHGRPEDKSKIVAEIRG
R5 : QVFALSTHPYGCYVIQRILEHCLPDQTLPILEELHQ
R6 : HTEQLVQDQYGSYVIRHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 55]

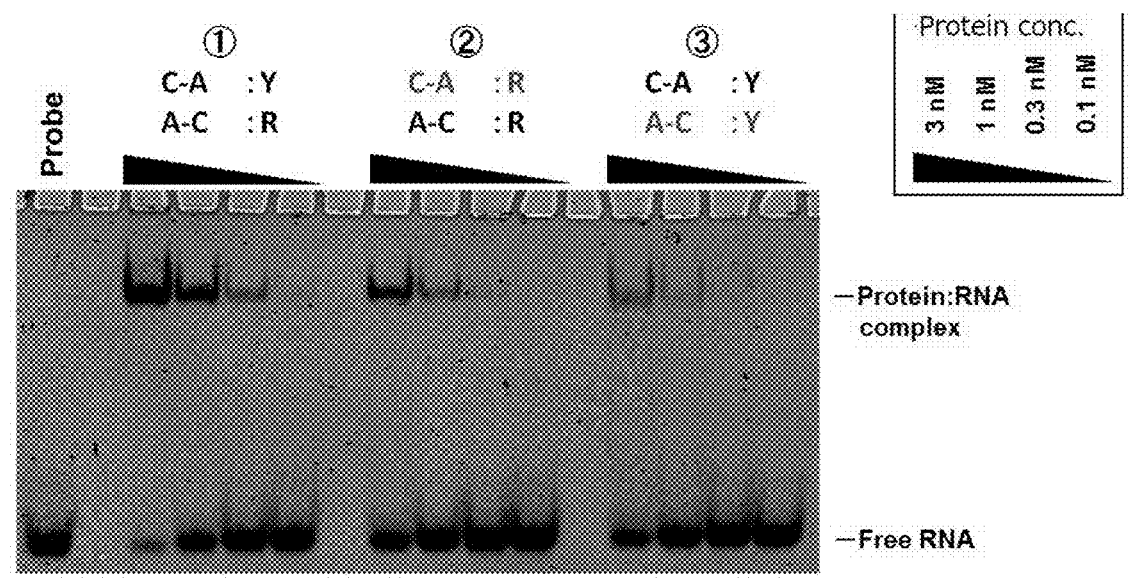

[Figure 56]

hPUF_MT (R5:A_13R)$_3$ (R6:G_13Y)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGSYVIEHVLEHGRPEDKSKIVAEIRG
R5 : QVFALSTHPYGCRVIQRILEHCLPDQTLPILEELHQ
R6 : HTEQLVQDQYGSYVIEHVLEHGRPEDKSKIVAEIRG
R5 : QVFALSTHPYGCRVIQRILEHCLPDQTLPILEELHQ
R6 : HTEQLVQDQYGSYVIEHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (R5:A_13R)$_3$ (R6:G_13R)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGSRVIEHVLEHGRPEDKSKIVAEIRG
R5 : QVFALSTHPYGCRVIQRILEHCLPDQTLPILEELHQ
R6 : HTEQLVQDQYGSRVIEHVLEHGRPEDKSKIVAEIRG
R5 : QVFALSTHPYGCRVIQRILEHCLPDQTLPILEELHQ
R6 : HTEQLVQDQYGSRVIEHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 57]

hPUF_MT (R5:A_13R) (R5:A_13Y)$_2$ (R6:G_13Y)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGSYVIEHVLEHGRPEDKSKIVAEIRG
R5 : QVFALSTHPYGCYVIQRILEHCLPDQTLPILEELHQ
R6 : HTEQLVQDQYGSYVIEHVLEHGRPEDKSKIVAEIRG
R5 : QVFALSTHPYGCYVIQRILEHCLPDQTLPILEELHQ
R6 : HTEQLVQDQYGSYVIEHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 58]

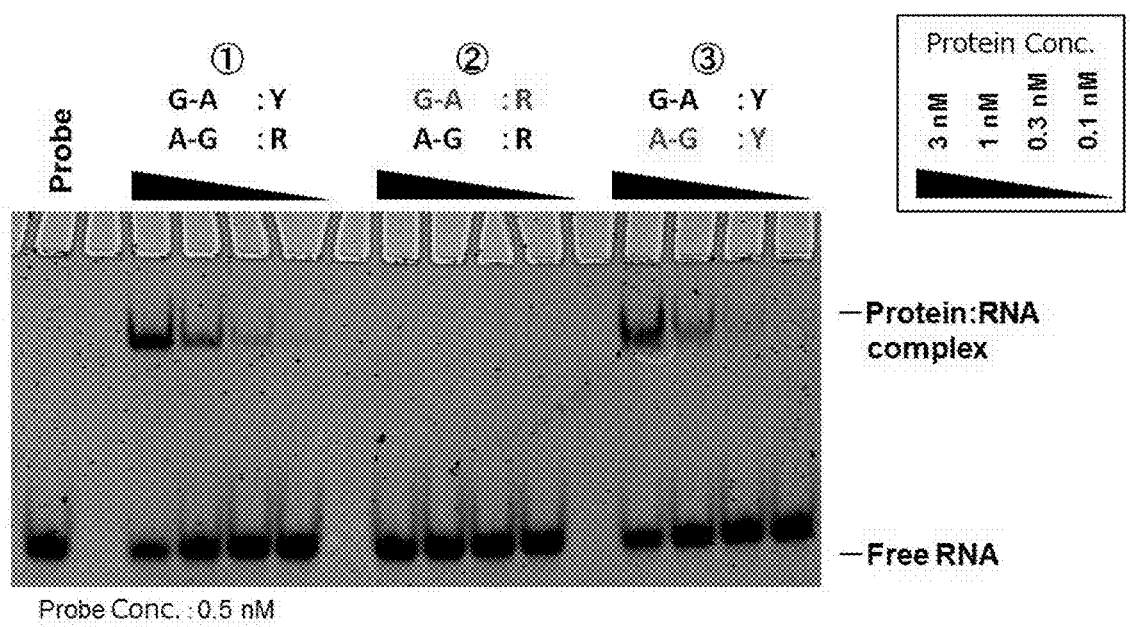

[Figure 59]

```
hPUF_MT (R5:G_13R)₃ (R6:U_13Y)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIERILEHCLPDQTLPILEELHQ
R6 : HTEQLVQDQYGNYVIQHVLEHGRPEDKSKIVAEIRG
R5 : QVFALSTHPYGSRVIERILEHCLPDQTLPILEELHQ
R6 : HTEQLVQDQYGNYVIQHVLEHGRPEDKSKIVAEIRG
R5 : QVFALSTHPYGSRVIERILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP hPUF_MT (R5:G_13R)₃ (R6:U_13R)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIERILEHCLPDQTLPILEELHQ
R6 : HTEQLVQDQYGNRVIQHVLEHGRPEDKSKIVAEIRG
R5 : QVFALSTHPYGSRVIERILEHCLPDQTLPILEELHQ
R6 : HTEQLVQDQYGNRVIQHVLEHGRPEDKSKIVAEIRG
R5 : QVFALSTHPYGSRVIERILEHCLPDQTLPILEELHQ
R6 : HTEQLVQDQYGNRVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP
```

[Figure 60]

hPUF_MT (R5:A_13R) (R5:A_13Y)$_2$ (R6:G_13Y)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSYVIERILEHCLPDQTLPILEELHQ
R6 : HTEQLVQDQYGNYVIQHVLEHGRPEDKSKIVAEIRG
R5 : QVFALSTHPYGSYVIERILEHCLPDQTLPILEELHQ
R6 : HTEQLVQDQYGNYVIQHVLEHGRPEDKSKIVAEIRG
R5 : QVFALSTHPYGSYVIERILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 61]

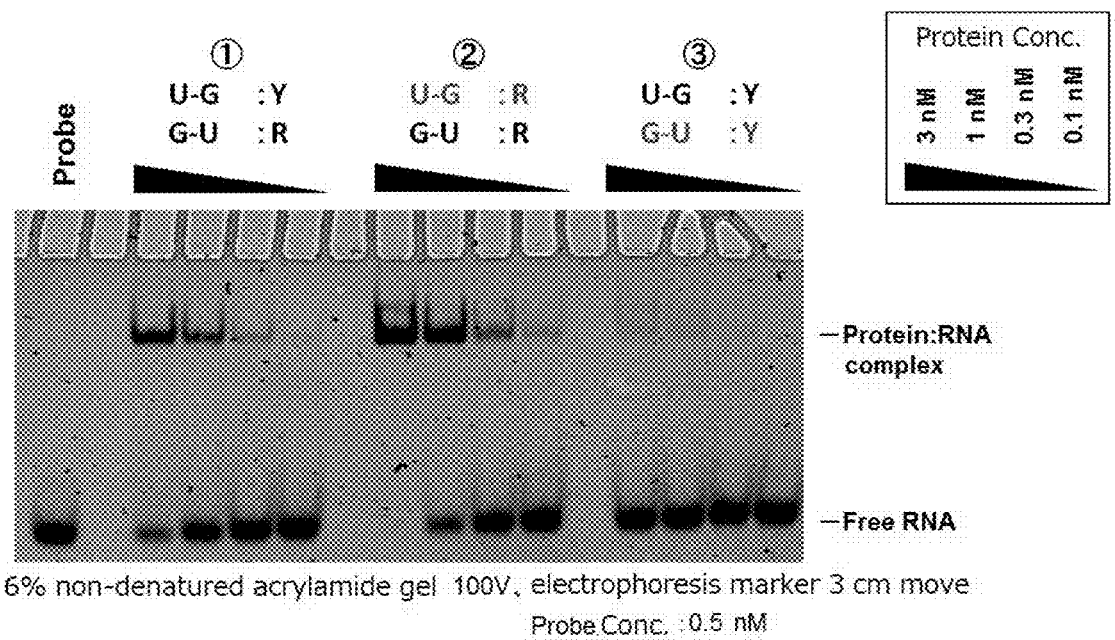

[Figure 62]

hPUF_MT (MT (5_(6)$_8$))
R1 : ELHQHTEQLVQDQYGCYVIQHVLEHGRPEDKSKIVA
R2 : ELHQHTEQLVQDQYGNYVIQHVLEHGRPEDKSKIVA
R3 : ELHQHTEQLVQDQYGCYVIQHVLEHGRPEDKSKIVA
R4 : ELHQHTEQLVQDQYGNYVIQHVLEHGRPEDKSKIVA
R5 : ELHQHTEQLVQDQYGCYVIQHVLEHGRPEDKSKIVA
R6 : ELHQHTEQLVQDQYGNYVIQHVLEHGRPEDKSKIVA
R7 : ELHQHTEQLVQDQYGSYVIEHVLEHGRPEDKSKIVA
R8 : ELHQHTEQLVQDQYGNYVIQHVLEHGRPEDKSKIVA hPUF_MT (6_(56)$_4$)
R1 : EIRGQVFALSTHPYGCRVIQRILEHCLPDQTLPILEELHQ
R2 :     HTEQLVQDQYGNYVIQHVLEHGRPEDKSKIVAEIRG
R3 :     QVFALSTHPYGCRVIQRILEHCLPDQTLPILEELHQ
R4 :     HTEQLVQDQYGNYVIQHVLEHGRPEDKSKIVAEIRG
R5 :     QVFALSTHPYGCRVIQRILEHCLPDQTLPILEELHQ
R6 :     HTEQLVQDQYGNYVIQHVLEHGRPEDKSKIVAEIRG
R7 :     QVFALSTHPYGSRVIERILEHCLPDQTLPILEELHQ
R8 :     HTEQLVQDQYGNYVIQHVLEHGRPEDKSKIVAEIRG
※ underline: terminal 4 amino acid of R6

[Figure 63]

hPUF_MT (4_(56)$_4$)

```
R1  : AFKGQVFALSTHPYGCRVIQRILEHCLPDQTLPILEELHQ
R2  :     HTEQLVQDQYGNYVIQHVLEHGRPEDKSKIVAAFKG
R3  :     QVFALSTHPYGCRVIQRILEHCLPDQTLPILEELHQ
R4  :     HTEQLVQDQYGNYVIQHVLEHGRPEDKSKIVAAFKG
R5  :     QVFALSTHPYGCRVIQRILEHCLPDQTLPILEELHQ
R6  :     HTEQLVQDQYGNYVIQHVLEHGRPEDKSKIVAAFKG
R7  :     QVFALSTHPYGSRVIERILEHCLPDQTLPILEELHQ
R8  :     HTEQLVQDQYGNYVIQHVLEHGRPEDKSKIVAEIRG
```

※ underline: terminal 4 amino acid of R4

[Figure 64]

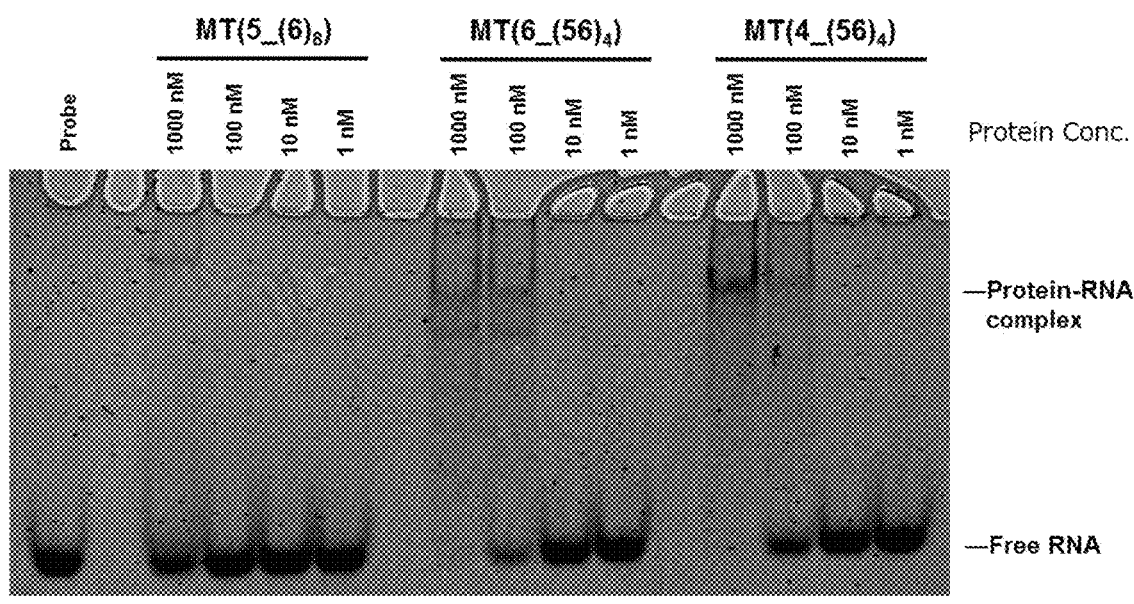

[Figure 65]

hPUF_MT (1-2-6-5-6-5-6-7-8)
R1 : HIMEFSQDQHGSRFIQLKLERATPAERQLVFNEILQ
R2 : AAYQLMVDVFGNYVIQKFFEFGSLEQKLALAERIRG
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 66]

hPUF_MT (1-2-5-5-6-5-6-7-8)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 67]

hPUF_MT (1-2-5-6-5-6-6-7-8)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 68]

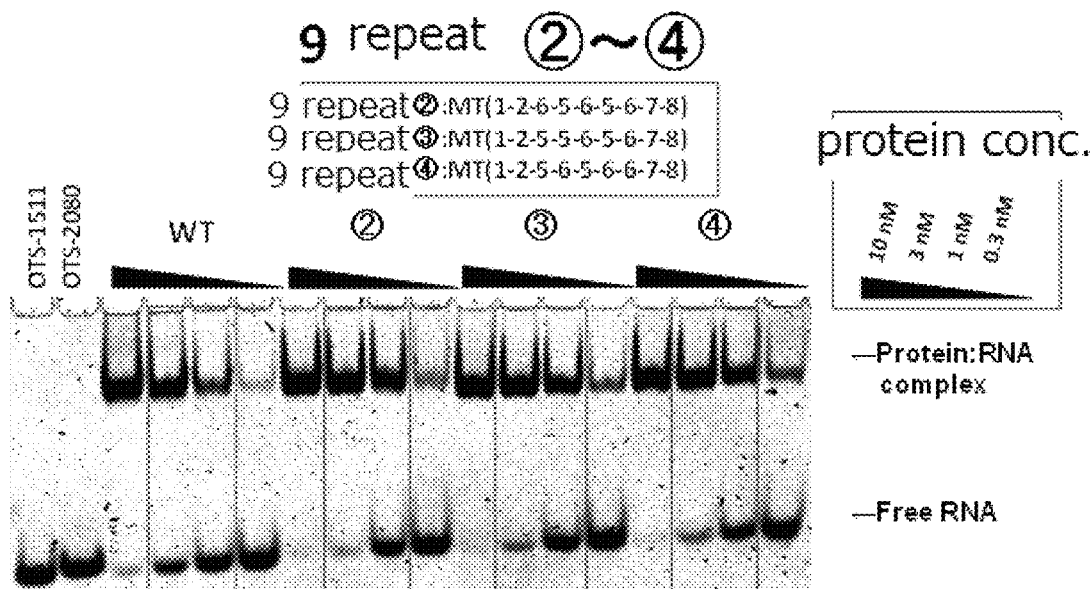

[Figure 69]

```
hPUF_MT (1-2-5-5-6-5-6-5-6-7-8)
R1  : HIMEFSQDQHGSRFIQLKLERATPAERQLVFNEILQ
R2  : AAYQLMVDVFGNYVIQKFFEFGSLEQKLALAERIRG
R5  : QVFALSTHPYGCRVIQRILEHCLPDQTLPILEELHQ
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R7  : NVLVLSQHKFASNVVEKCVTHASRTERAVLIDEVCTMNDGPHS
R8  : ALYTMMKDQYANYVVQKMIDVAEPGQRKIVMHKIRP
```

[Figure 70]

```
hPUF_MT (1-2-5-5-6-5-6-5-6-5-6-7-8)
R1  : HIMEFSQDQHGSRFIQLKLERATPAERQLVFNEILQ
R2  : AAYQLMVDVFGNYVIQKFFEFGSLEQKLALAERIRG
R5  : QVFALSTHPYGCRVIQRILEHCLPDQTLPILEELHQ
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R5  : QVFALSTHPYGCRVIQRILEHCLPDQTLPILEELHQ
R6  : HTEQLVQDQYGNYVIQHVLEHGRPEDKSKIVAEIRG
R7  : NVLVLSQHKFASNVVEKCVTHASRTERAVLIDEVCTMNDGPHS
R8  : ALYTMMKDQYANYVVQKMIDVAEPGQRKIVMHKIRP
```

[Figure 71]

```
hPUF_MT (1-2-5-5-6-5-6-5-6-5-6-5-6-7-8)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP
```

[Figure 72]

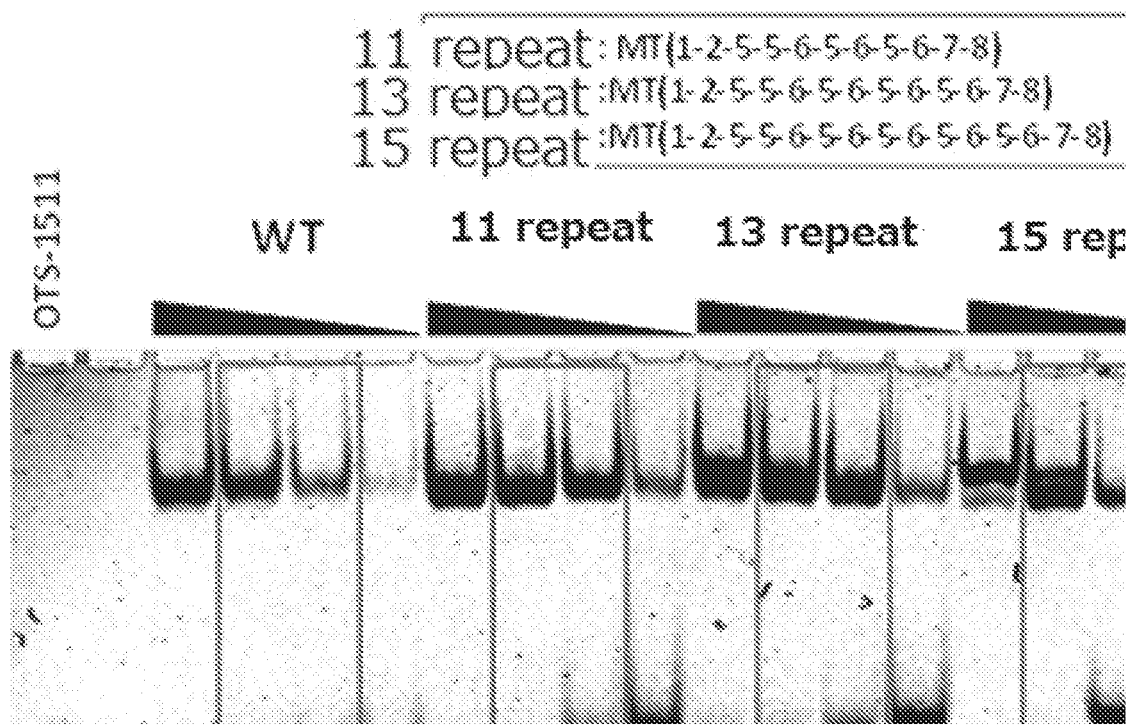

[Figure 73]

hPUF_MT (R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 74]

hPUF_MT (R1_S12N, R3→R5, R4→R6)
R1 : HIMEFSQDQHGNRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 75]

hPUF_MT (R1_Q16E, R3→R5, R4→R6)
R1 : HIMEFSQDQHGSRFIELKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 76]

hPUF_MT (R1_Q16R, R3→R5, R4→R6)
R1 : HIMEFSQDQHGSRFIRLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 77]

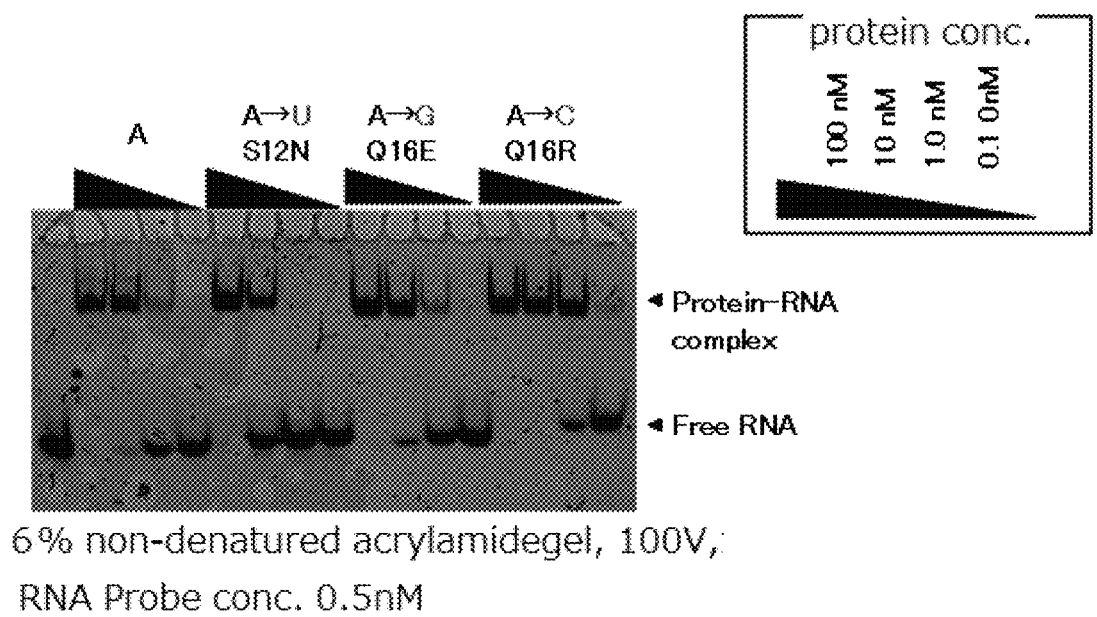

[Figure 78]

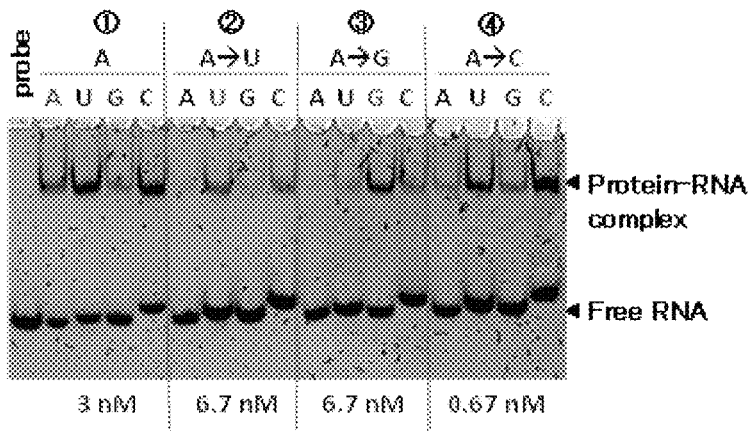

6% non-denatured acrylamidegel, 100V,
RNA Probe conc. 0.5nM

[Figure 79]

```
hPUF_MT (R3→R5, R4→R6)  (=new backbone)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP
```

[Figure 80]

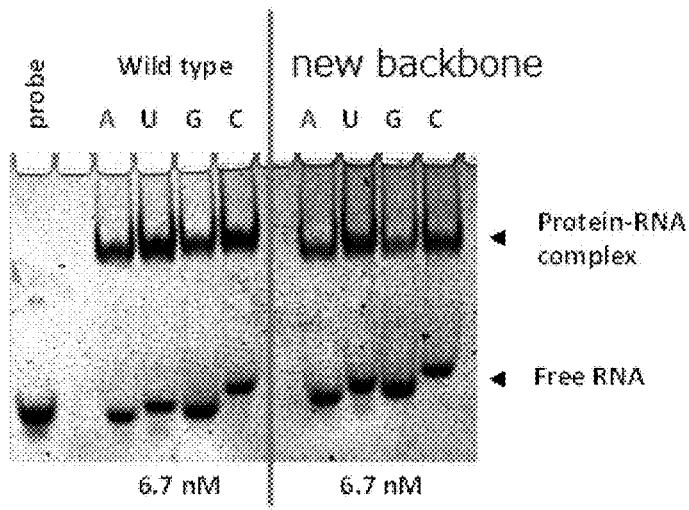

6% non-denatured acrylamidegel, 100V,
RNA Probe conc. 0.5nM

[Figure 81]

hPUF_MT (R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 82]

hPUF_MT (R2_N12C, R3→R5, R4→R6)
R1 : HIMEFSQDQHGSRFIQLKLERATPAERQLVFNEILQ
R2 : AAYQLMVDVFGCYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 83]

hPUF_MT (R2_N12S, R3→R5, R4→R6)
R1 : HIMEFSQDQHGSRFIQLKLERATPAERQLVFNEILQ
R2 : AAYQLMVDVFGSYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 84]

hPUF_MT (R2_N12S, Q16E, R3→R5, R4→R6)
R1 : HIMEFSQDQHGSRFIQLKLERATPAERQLVFNEILQ
R2 : AAYQLMVDVFGSYVIEKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 85]

hPUF_MT (R2_N12S, Q16R, R3→R5, R4→R6)
R1 : HIMEFSQDQHGSRFIQLKLERATPAERQLVFNEILQ
R2 : AAYQLMVDVFGSYVIRKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 86]

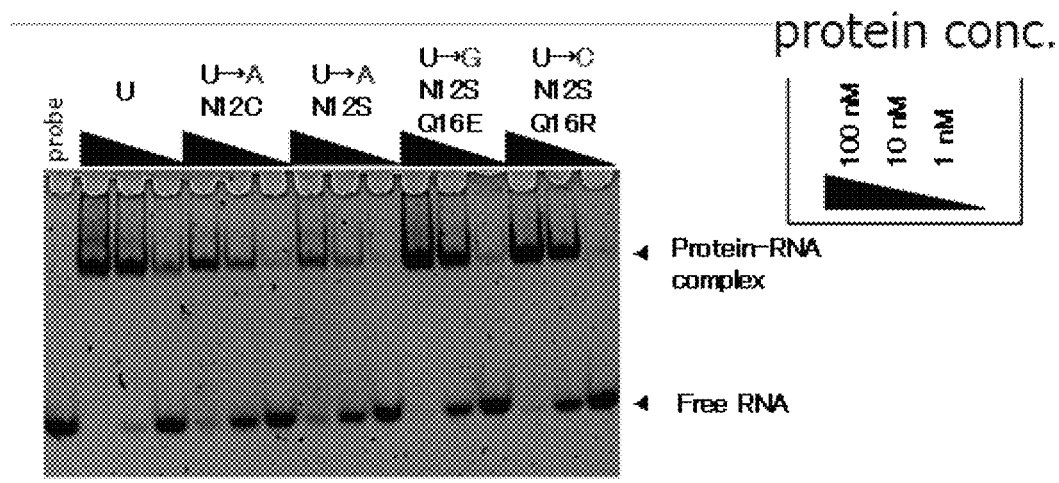

6% non-denatured acrylamidegel, 100V,
RNA probe conc.:0.5nM

[Figure 87]

hPUF_MT (R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 88]

hPUF_MT (R2_N12C, R3→R5, R4→R6)
R1 : HIMEFSQDQHGSRFIQLKLERATPAERQLVFNEILQ
R2 : AAYQLMVDVFGCYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 89]

hPUF_MT (R2_N12S, Q16E, R3→R5, R4→R6)
R1 : HIMEFSQDQHGSRFIQLKLERATPAERQLVFNEILQ
R2 : AAYQLMVDVFGSYVIEKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 90]

hPUF_MT (R2_N12S, Q16R, R3→R5, R4→R6)
R1 : HIMEFSQDQHGSRFIQLKLERATPAERQLVFNEILQ
R2 : AAYQLMVDVFGSYVIRKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 91]

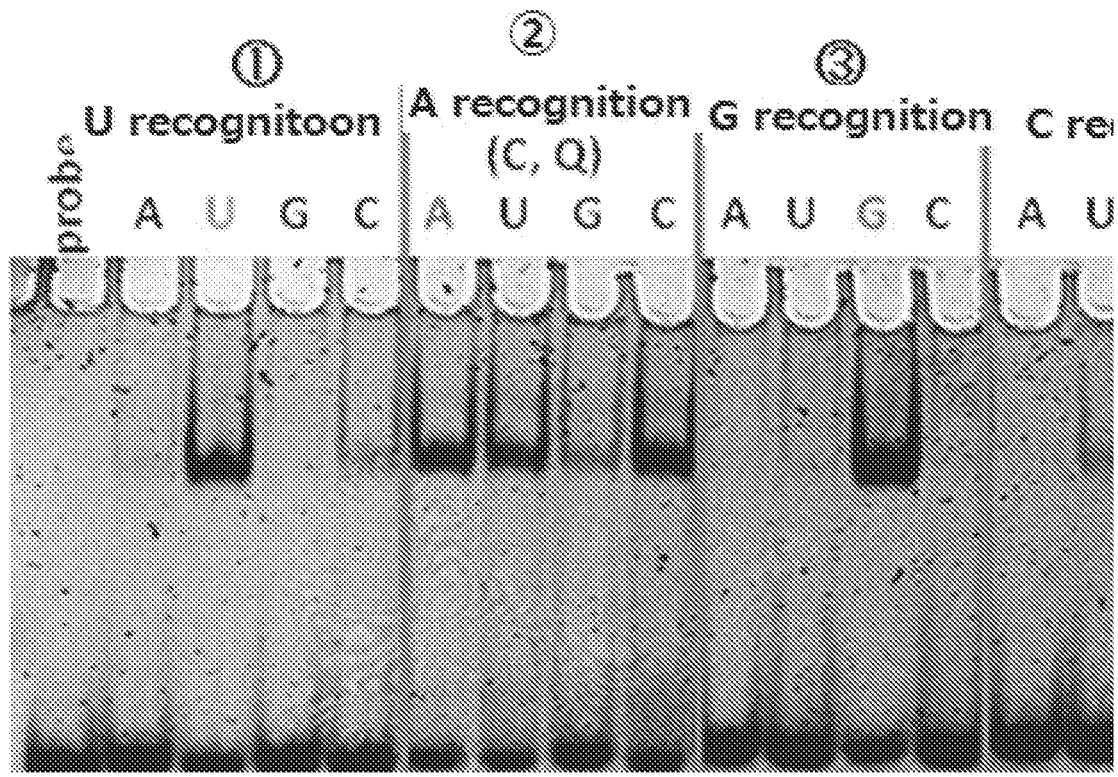

[Figure 92]

hPUF_MT (R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 93]

hPUF_MT (R7_S12C, E16Q, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFACNVVQKCVTHASRTERAVLIDEVCTMNDGPHS
R8 : ALYTMMKDQYANYVVQKMIDVAEPGQRKIVMHKIRP

[Figure 94]

hPUF_MT (R7_E16Q, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVQKCVTHASRTERAVLIDEVCTMNDGPHS
R8 : ALYTMMKDQYANYVVQKMIDVAEPGQRKIVMHKIRP

[Figure 95]

hPUF_MT (R7_S12N, E16Q, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFANNVVQKCVTHASRTERAVLIDEVCTMNDGPHS
R8 : ALYTMMKDQYANYVVQKMIDVAEPGQRKIVMHKIRP

[Figure 96]

hPUF_MT (R7_E16R, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVRKCVTHASRTERAVLIDEVCTMNDGPHS
R8 : ALYTMMKDQYANYVVQKMIDVAEPGQRKIVMHKIRP

[Figure 97]

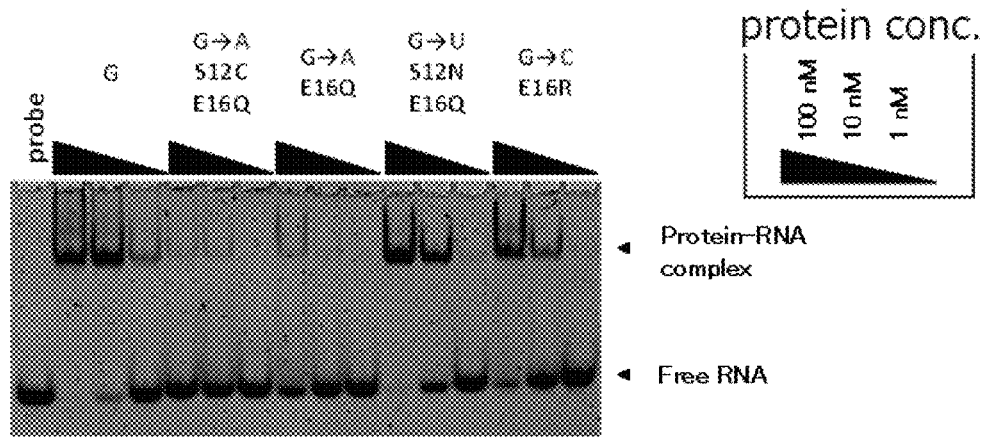

[Figure 98]

hPUF_MT (R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 99]

hPUF_MT (R7_S12C, E16Q, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFACNVVQKCVTHASRTERAVLIDEVCTMNDGPHS
R8 : ALYTMMKDQYANYVVQKMIDVAEPGQRKIVMHKIRP

[Figure 100]

hPUF_MT (R7_S12N, E16Q, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFANNVVQKCVTHASRTERAVLIDEVCTMNDGPHS
R8 : ALYTMMKDQYANYVVQKMIDVAEPGQRKIVMHKIRP

[Figure 101]

hPUF_MT (R7_E16R, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVRKCVTHASRTERAVLIDEVCTMNDGPHS
R8 : ALYTMMKDQYANYVVQKMIDVAEPGQRKIVMHKIRP

[Figure 102]

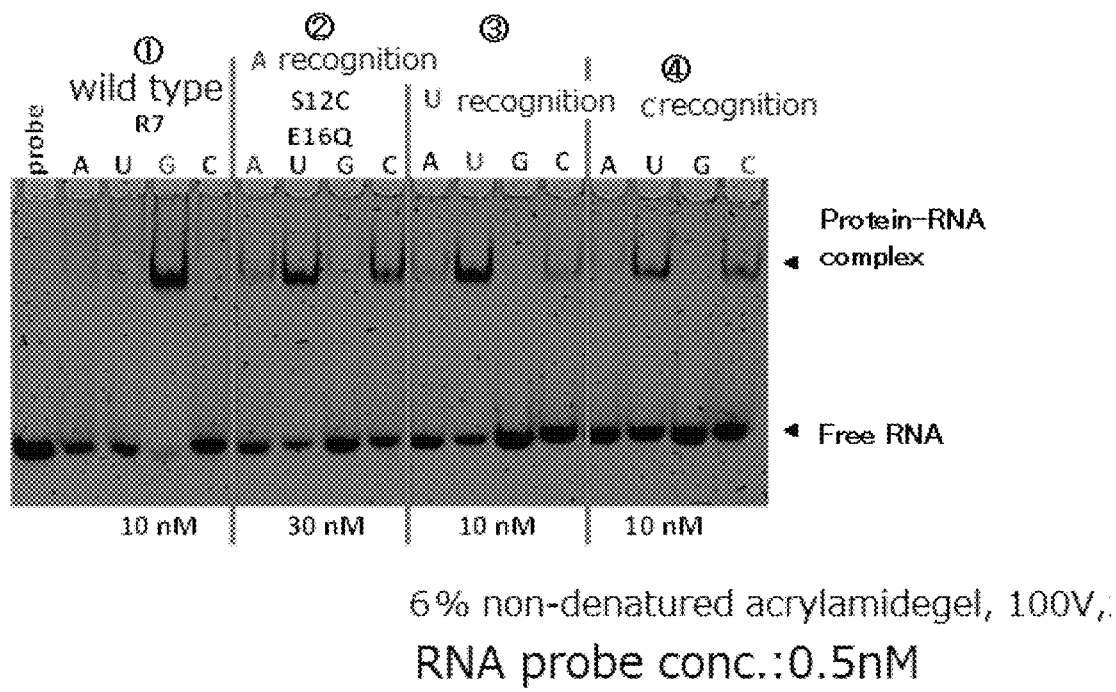

6% non-denatured acrylamidegel, 100V,
RNA probe conc.:0.5nM

[Figure 103]

hPUF_MT (R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 104]

hPUF_MT (R8_N12C, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYACYVVQKMIDVAEPGQRKIVMHKIRP

[Figure 105]

hPUF_MT (R8_N12S, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYASYVVQKMIDVAEPGQRKIVMHKIRP

[Figure 106]

hPUF_MT (R8_N12S, Q16E, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYASYVVEKMIDVAEPGQRKIVMHKIRP

[Figure 107]

hPUF_MT (R8_N12S, Q16R, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYASYVVRKMIDVAEPGQRKIVMHKIRP

[Figure 108]

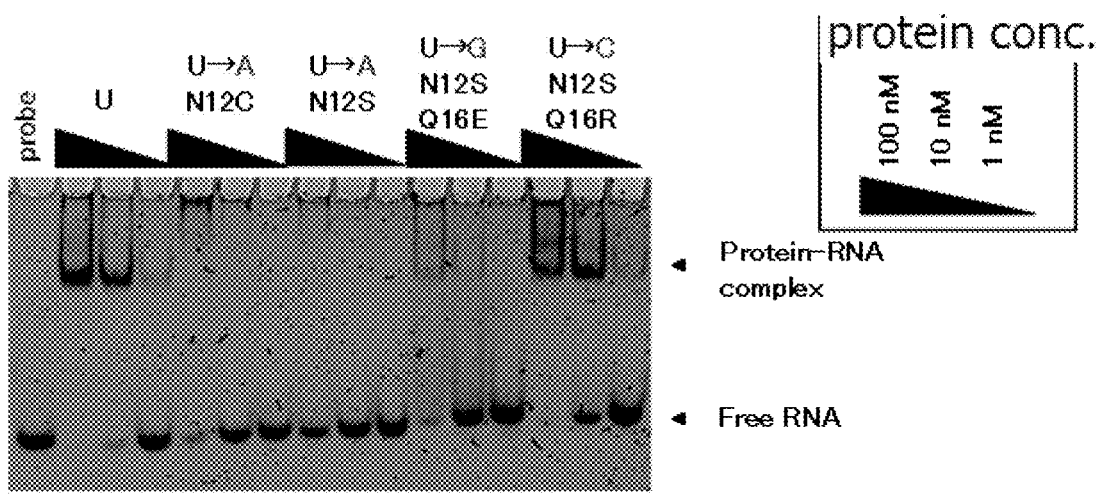

6% non-denatured acrylamidegel, 100V,
RNA probe conc.:0.5nM

[Figure 109]

hPUF_MT (R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 110]

hPUF_MT (R8_N12C, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYACYVVQKMIDVAEPGQRKIVMHKIRP

[Figure 111]

hPUF_MT (R8_N12S, Q16E, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYASYVVEKMIDVAEPGQRKIVMHKIRP

[Figure 112]

hPUF_MT (R8_N12S, Q16R, R3→R5, R4→R6)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYASYVVRKMIDVAEPGQRKIVMHKIRP

[Figure 113]

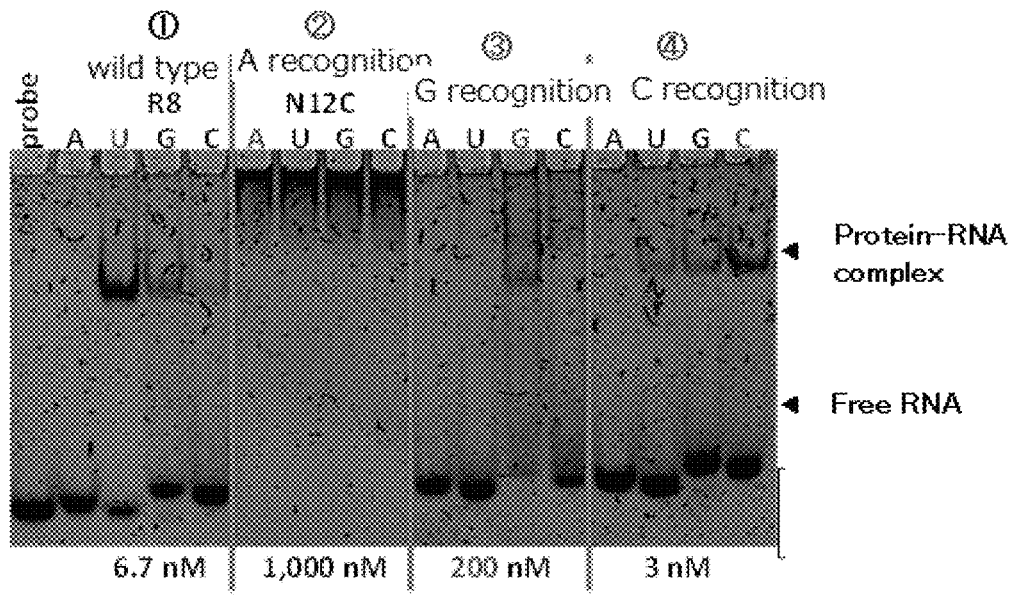

6% non-denatured acrylamidegel, 100V,
RNA probe conc.:0.5nM

[Figure 114]
verification of stacking amino acids
about different nucleotides
① Y and R are arranged alternately
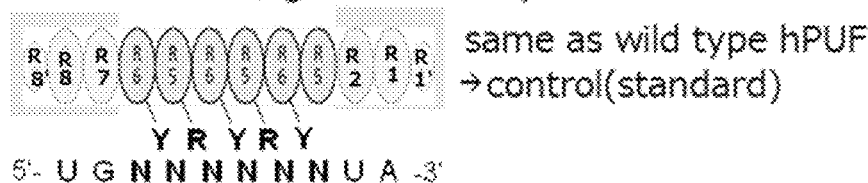
same as wild type hPUF
→control(standard)
② All are R
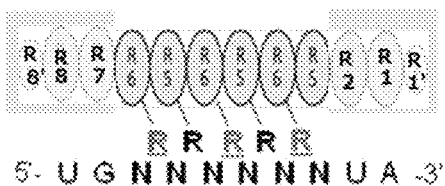
③ All are Y
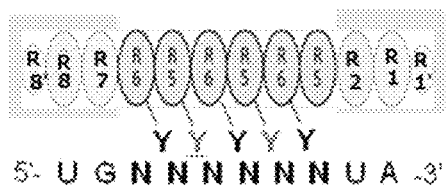
[Figure 115]
Optimization of amino acid between U-A/A-U
① Y and R are arranged alternately
same as wild type hPUF
→control(standard)
② All are R
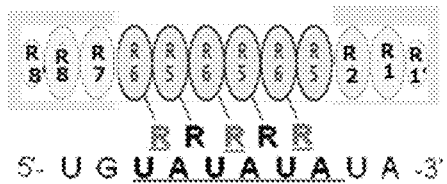
③ All are Y
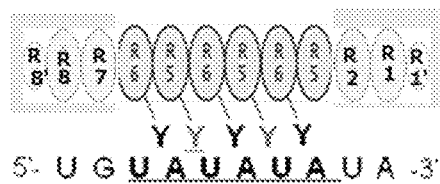

[Figure 116]

hPUF_MT (R5:A_13R)₃(R6:U_13Y)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 117]

hPUF_MT (R5:A_13R)₃(R6:U_13R)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNRVIQHVLEHGRPEDKSKIVAEIRG
R5 : QVFALSTHPYGCRVIQRILEHCLPDQTLPILEELHQ
R6 : HTEQLVQDQYGNRVIQHVLEHGRPEDKSKIVAEIRG
R5 : QVFALSTHPYGCRVIQRILEHCLPDQTLPILEELHQ
R6 : HTEQLVQDQYGNRVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 118]

hPUF_MT (R5:A_13R) (R5:A_13Y)$_2$ (R6:U_13Y)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R6 : HTEQLVQDQYGNYVIQHVLEHGRPEDKSKIVAEIRG
R5 : QVFALSTHPYGCYVIQRILEHCLPDQTLPILEELHQ
R6 : HTEQLVQDQYGNYVIQHVLEHGRPEDKSKIVAEIRG
R5 : QVFALSTHPYGCYVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 119]

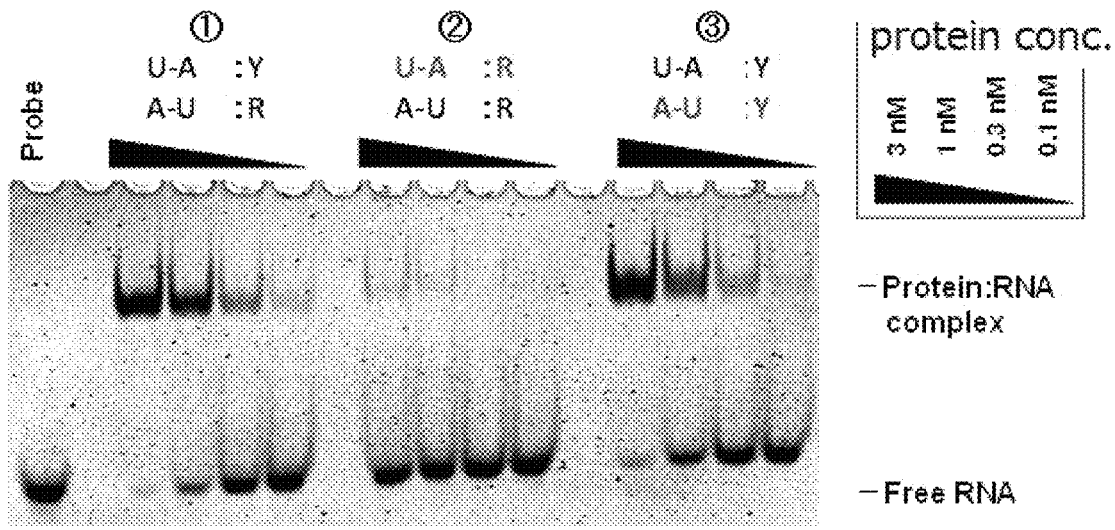

[Figure 120]

Optimization of amino acid between C-G/G-C

① Y and R are arranged alternately

same as wild type hPUF
→control(standard)

② All are R

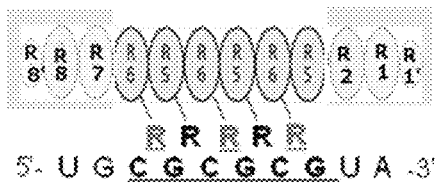

③ All are Y

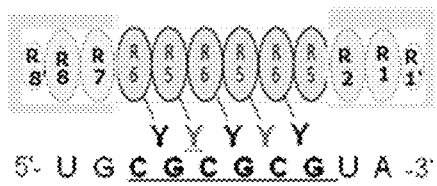

[Figure 121]

hPUF_MT (R5:G_13R)₃(R6:C_13Y)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIERILEHCLPDQTLPILEELHQ
R6 : HTEQLVQDQYGSYVIRHVLEHGRPEDKSKIVAEIRG
R5 : QVFALSTHPYGSRVIERILEHCLPDQTLPILEELHQ
R6 : HTEQLVQDQYGSYVIRHVLEHGRPEDKSKIVAEIRG
R5 : QVFALSTHPYGSRVIERILEHCLPDQTLPILEELHQ
R6 : HTEQLVQDQYGSYVIRHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 122]

hPUF_MT (R5:G_13R)$_3$ (R6:C_13R)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIERILEHCLPDQTLPILEELHQ
R6 : HTEQLVQDQYGSRVIRHVLEHGRPEDKSKIVAEIRG
R5 : QVFALSTHPYGSRVIERILEHCLPDQTLPILEELHQ
R6 : HTEQLVQDQYGSRVIRHVLEHGRPEDKSKIVAEIRG
R5 : QVFALSTHPYGSRVIERILEHCLPDQTLPILEELHQ
R6 : HTEQLVQDQYGSRVIRHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 123]

hPUF_MT (R5:G_13R) (R5:G_13Y)$_2$ (R6:C_13Y)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIERILEHCLPDQTLPILEELHQ
R6 : HTEQLVQDQYGSYVIRHVLEHGRPEDKSKIVAEIRG
R5 : QVFALSTHPYGSYVIERILEHCLPDQTLPILEELHQ
R6 : HTEQLVQDQYGSYVIRHVLEHGRPEDKSKIVAEIRG
R5 : QVFALSTHPYGSYVIERILEHCLPDQTLPILEELHQ
R6 : HTEQLVQDQYGSYVIRHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 124]
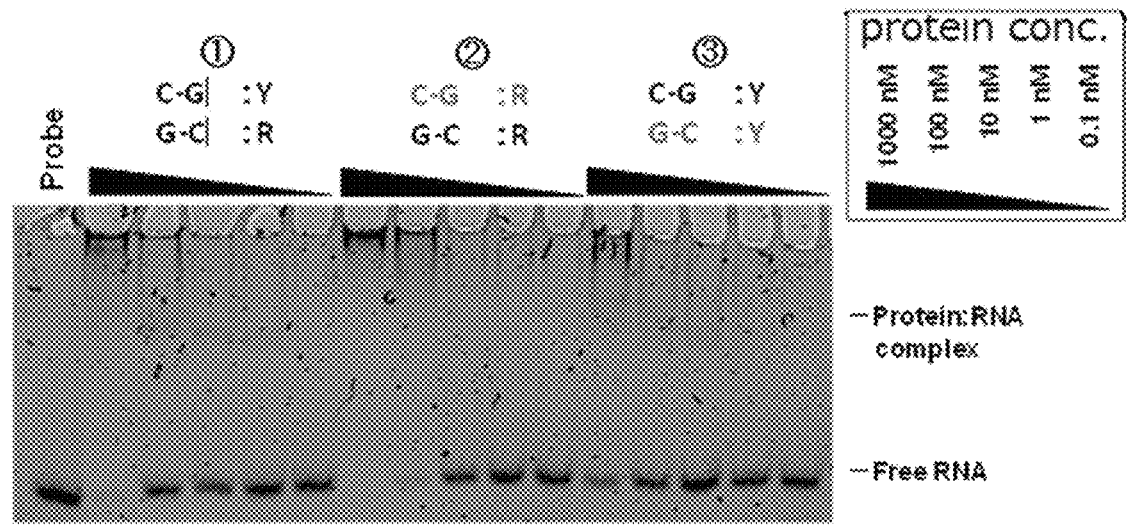
6% non-denatured acrylamidegel, 100V,
electrophoresis marker 3 cm move
Probe conc.: 0.5nM
[Figure 125]
Optimization of amino acid between U-C/C-U
①Y and R are arranged alternately
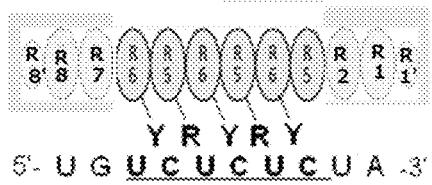
same as wild type hPUF
→control(standard)
②All are R
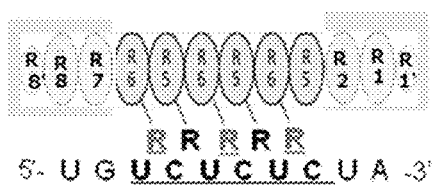
③All are Y
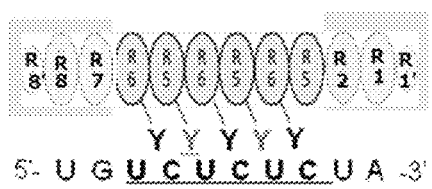

[Figure 126]

hPUF_MT (R5:C_13R)$_3$(R6:U_13Y)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIRRILEHCLPDQTLPILEELHQ
R6 : HTEQLVQDQYGNYVIQHVLEHGRPEDKSKIVAEIRG
R5 : QVFALSTHPYGSRVIRRILEHCLPDQTLPILEELHQ
R6 : HTEQLVQDQYGNYVIQHVLEHGRPEDKSKIVAEIRG
R5 : QVFALSTHPYGSRVIRRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 127]

hPUF_MT (R5:C_13R)$_3$(R6:U_13R)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIRRILEHCLPDQTLPILEELHQ
R6 : HTEQLVQDQYGNRVIQHVLEHGRPEDKSKIVAEIRG
R5 : QVFALSTHPYGSRVIRRILEHCLPDQTLPILEELHQ
R6 : HTEQLVQDQYGNRVIQHVLEHGRPEDKSKIVAEIRG
R5 : QVFALSTHPYGSRVIRRILEHCLPDQTLPILEELHQ
R6 : HTEQLVQDQYGNRVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 128]

hPUF_MT (R5:C_13R) (R5:C_13Y)$_2$ (R6:U_13Y)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIRRILEHCLPDQTLPILEELHQ
R6 : HTEQLVQDQYGNYVIQHVLEHGRPEDKSKIVAEIRG
R5 : QVFALSTHPYGSYVIRRILEHCLPDQTLPILEELHQ
R6 : HTEQLVQDQYGNYVIQHVLEHGRPEDKSKIVAEIRG
R5 : QVFALSTHPYGSYVIRRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 129]

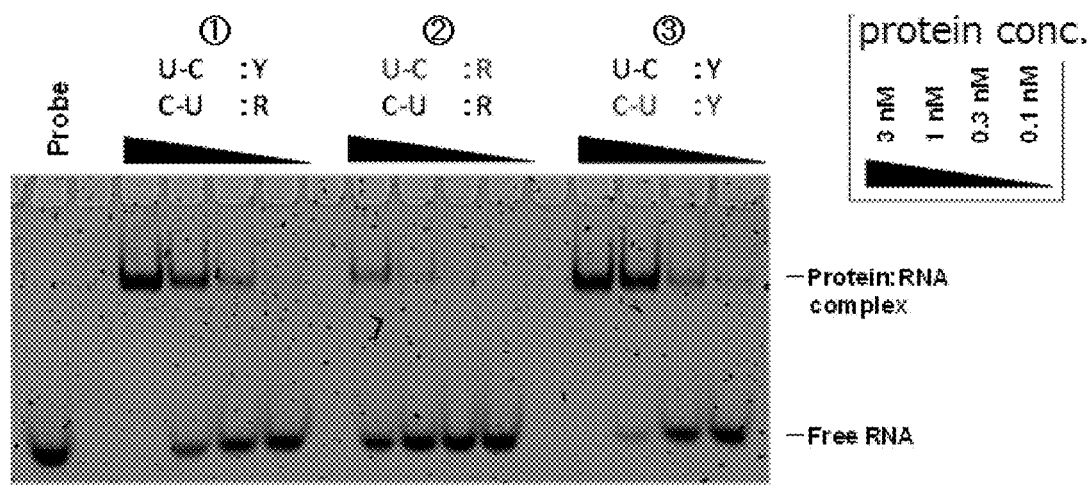

[Figure 130]
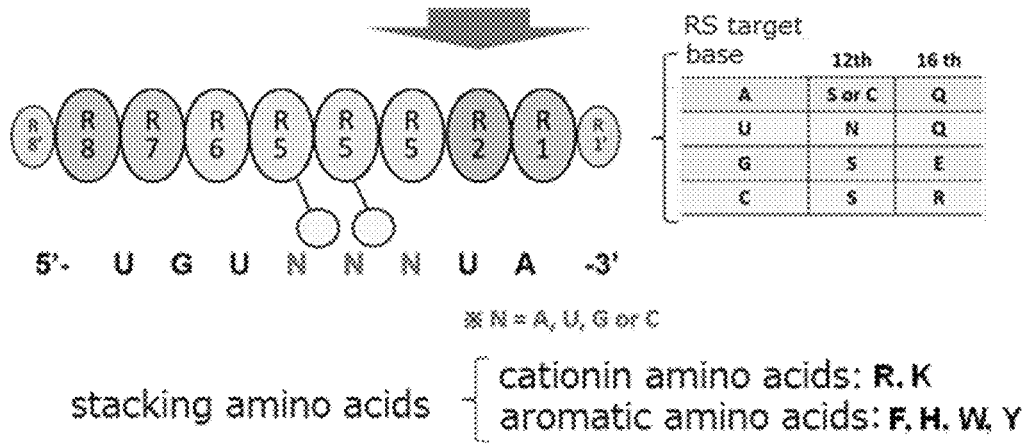
[Figure 131]
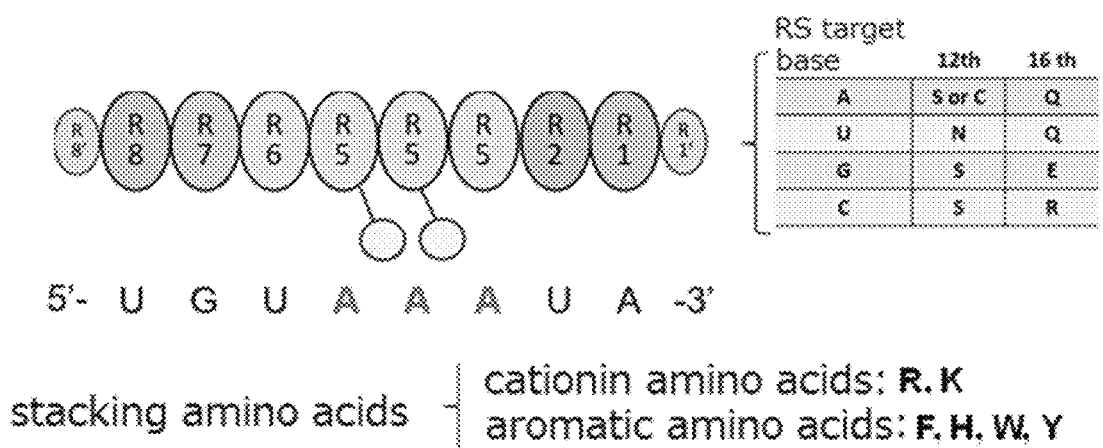

[Figure 132]

hPUF_MT (R3→R5, R4→R5)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R5 : QVFALSTHPYGCRVIQRILEHCLPDQTLPILEELHQ
R5 : QVFALSTHPYGCRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 133]

hPUF_MT (R3→R5, R4→R5_R13K, R5_R13K)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQKILEHCLPDQTLPILEELHQ
R5 : QVFALSTHPYGCKVIQKILEHCLPDQTLPILEELHQ
R5 : QVFALSTHPYGCKVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 134]

hPUF_MT (R3→R5, R4→R5_R13F, R5_R13F)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R5 : QVFALSTHPYGCFVIQRILEHCLPDQTLPILEELHQ
R5 : QVFALSTHPYGCFVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 135]

```
hPUF_MT (R3→R5, R4→R5_R13H, R5_R13H)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R5 : QVFALSTHPYGCHVIQRILEHCLPDQTLPILEELHQ
R5 : QVFALSTHPYGCHVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP
```

[Figure 136]

```
hPUF_MT (R3→R5, R4→R5_R13W, R5_R13W)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R5 : QVFALSTHPYGCWVIQRILEHCLPDQTLPILEELHQ
R5 : QVFALSTHPYGCWVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP
```

[Figure 137]

```
hPUF_MT (R3→R5, R4→R5_R13Y, R5_R13Y)
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGCRVIQRILEHCLPDQTLPILEELHQ
R5 : QVFALSTHPYGCYVIQRILEHCLPDQTLPILEELHQ
R5 : QVFALSTHPYGCYVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP
```

[Figure 138]
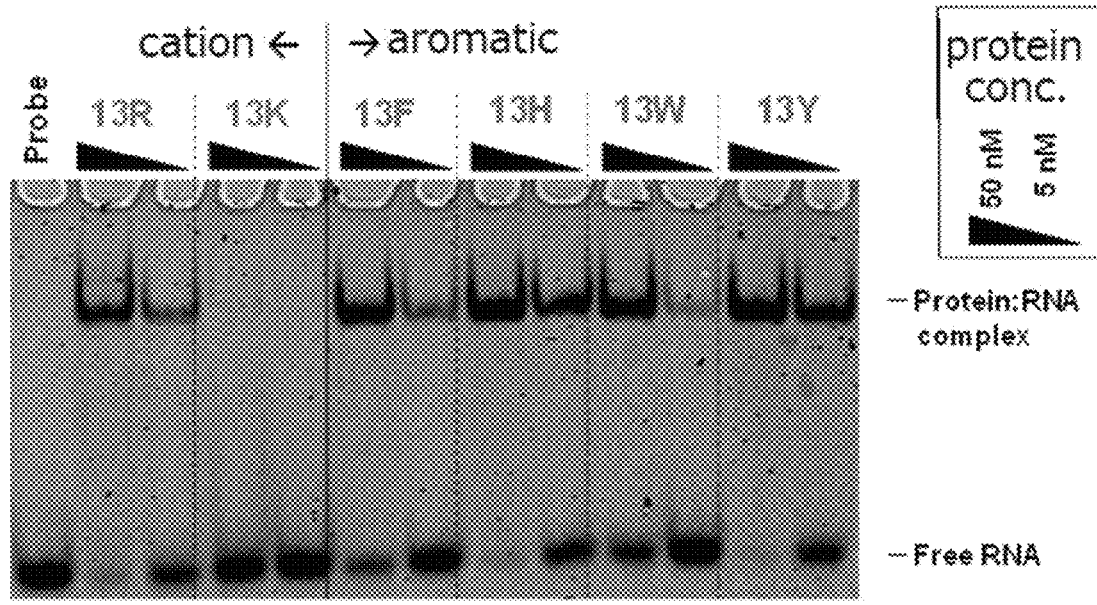
[Figure 139]
Optimization of amino acids between G-G
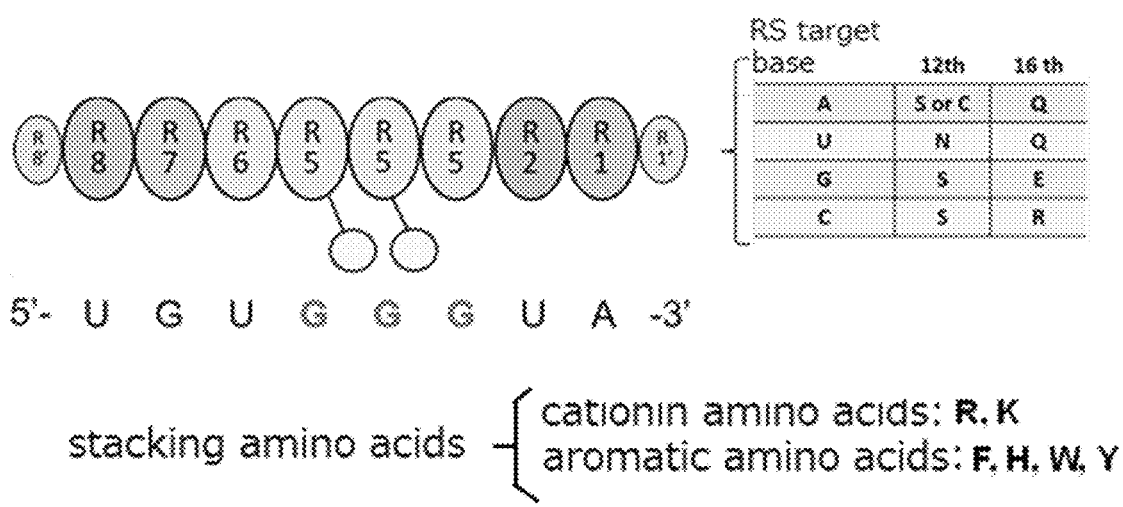

[Figure 140]

hPUF_MT (R5:G_13R)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIERILEHCLPDQTLPILEELHQ
R5 : QVFALSTHPYGSRVIERILEHCLPDQTLPILEELHQ
R5 : QVFALSTHPYGSRVIERILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 141]

hPUF_MT (R5:G_13K)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIERILEHCLPDQTLPILEELHQ
R5 : QVFALSTHPYGSKVIERILEHCLPDQTLPILEELHQ
R5 : QVFALSTHPYGSKVIERILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 142]

hPUF_MT (R5:G_13F)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIERILEHCLPDQTLPILEELHQ
R5 : QVFALSTHPYGSFVIERILEHCLPDQTLPILEELHQ
R5 : QVFALSTHPYGSFVIERILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 143]

hPUF_MT (R5:G_13H)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIERILEHCLPDQTLPILEELHQ
R5 : QVFALSTHPYGSHVIERILEHCLPDQTLPILEELHQ
R5 : QVFALSTHPYGSHVIERILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 144]

hPUF_MT (R5:G_13W)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIERILEHCLPDQTLPILEELHQ
R5 : QVFALSTHPYGSWVIERILEHCLPDQTLPILEELHQ
R5 : QVFALSTHPYGSWVIERILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 145]

hPUF_MT (R5:G_13Y)$_3$
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIERILEHCLPDQTLPILEELHQ
R5 : QVFALSTHPYGSYVIERILEHCLPDQTLPILEELHQ
R5 : QVFALSTHPYGSYVIERILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 146]
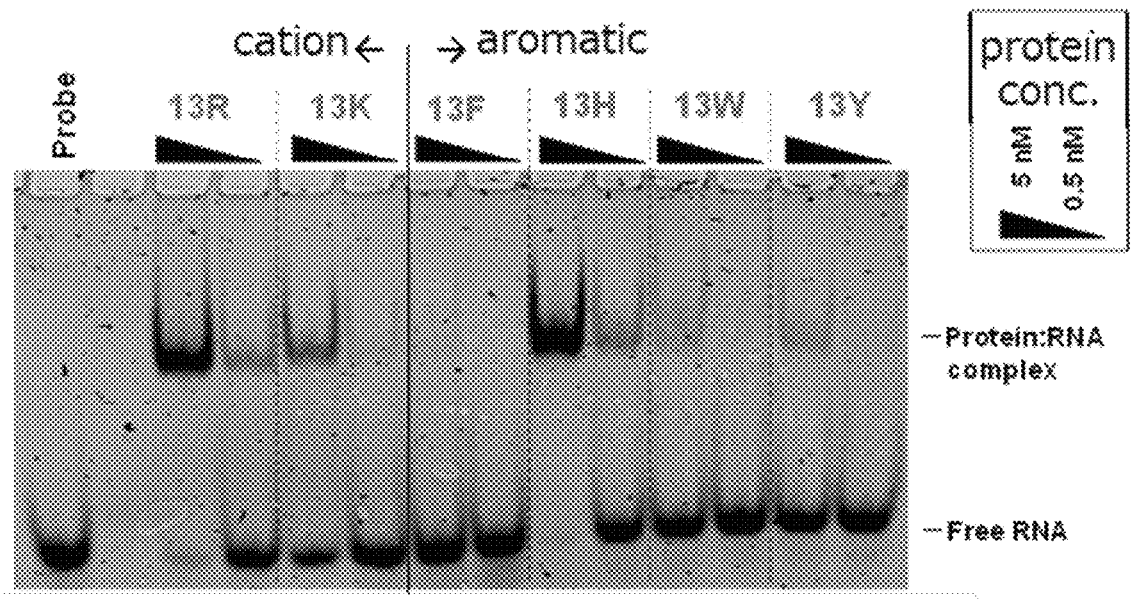
[Figure 147]
Optimization of amino acids between U-U
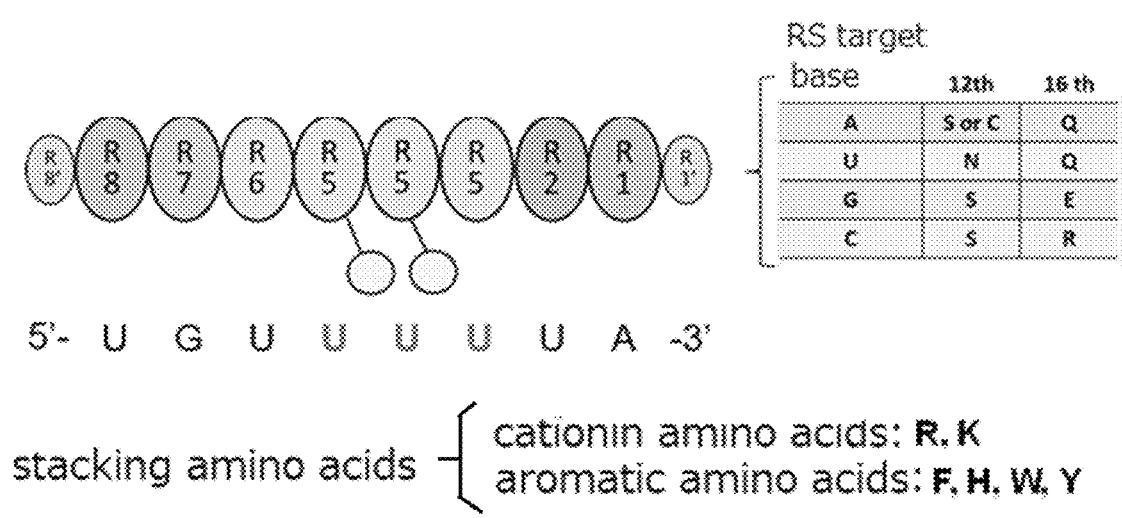

[Figure 148]

hPUF_MT (R5:U_13R)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGNRVIQRILEHCLPDQTLPILEELHQ
R5 : QVFALSTHPYGNRVIQRILEHCLPDQTLPILEELHQ
R5 : QVFALSTHPYGNRVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 149]

hPUF_MT (R5:U_13K)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGNRVIQRILEHCLPDQTLPILEELHQ
R5 : QVFALSTHPYGNKVIQRILEHCLPDQTLPILEELHQ
R5 : QVFALSTHPYGNKVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 150]

hPUF_MT (R5:U_13F)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGNRVIQRILEHCLPDQTLPILEELHQ
R5 : QVFALSTHPYGNFVIQRILEHCLPDQTLPILEELHQ
R5 : QVFALSTHPYGNFVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 151]

hPUF_MT (R5:U_13H)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGNRVIQRILEHCLPDQTLPILEELHQ
R5 : QVFALSTHPYGNHVIQRILEHCLPDQTLPILEELHQ
R5 : QVFALSTHPYGNHVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 152]

hPUF_MT (R5:U_13W)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGNRVIQRILEHCLPDQTLPILEELHQ
R5 : QVFALSTHPYGNWVIQRILEHCLPDQTLPILEELHQ
R5 : QVFALSTHPYGNWVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 153]

hPUF_MT (R5:U_13Y)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGNRVIQRILEHCLPDQTLPILEELHQ
R5 : QVFALSTHPYGNYVIQRILEHCLPDQTLPILEELHQ
R5 : QVFALSTHPYGNYVIQRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 154]
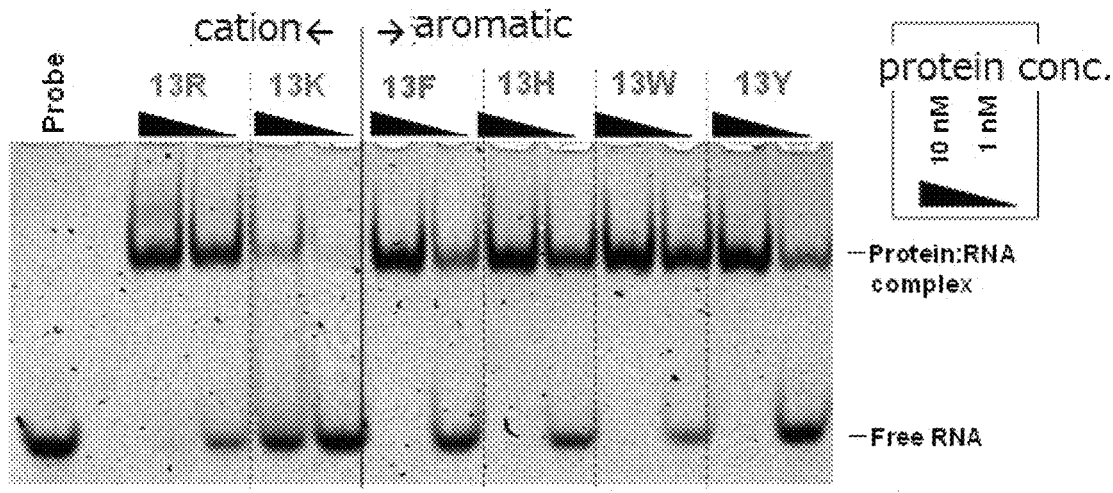
[Figure 155]

[Figure 156]

hPUF_MT (R5:C_13R)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIRRILEHCLPDQTLPILEELHQ
R5 : QVFALSTHPYGSRVIRRILEHCLPDQTLPILEELHQ
R5 : QVFALSTHPYGSRVIRRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 157]

hPUF_MT (R5:C_13K)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIRRILEHCLPDQTLPILEELHQ
R5 : QVFALSTHPYGSKVIRRILEHCLPDQTLPILEELHQ
R5 : QVFALSTHPYGSKVIRRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 158]

hPUF_MT (R5:C_13F)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIRRILEHCLPDQTLPILEELHQ
R5 : QVFALSTHPYGSFVIRRILEHCLPDQTLPILEELHQ
R5 : QVFALSTHPYGSFVIRRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 159]

hPUF_MT (R5:C_13H)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIRRILEHCLPDQTLPILEELHQ
R5 : QVFALSTHPYGSHVIRRILEHCLPDQTLPILEELHQ
R5 : QVFALSTHPYGSHVIRRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 160]

hPUF_MT (R5:C_13W)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIRRILEHCLPDQTLPILEELHQ
R5 : QVFALSTHPYGSWVIRRILEHCLPDQTLPILEELHQ
R5 : QVFALSTHPYGSWVIRRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 161]

hPUF_MT (R5:C_13Y)₃
R1 : HIMEFSQDQHGSRFIQLKLERATPAERQLVFNEILQ
R2 : AAYQLMVDVFGNYVIQKFFEFGSLEQKLALAERIRG
R5 : QVFALSTHPYGSRVIRRILEHCLPDQTLPILEELHQ
R5 : QVFALSTHPYGSYVIRRILEHCLPDQTLPILEELHQ
R5 : QVFALSTHPYGSYVIRRILEHCLPDQTLPILEELHQ
R6 : HTEQLVQDQYGNYVIQHVLEHGRPEDKSKIVAEIRG
R7 : NVLVLSQHKFASNVVEKCVTHASRTERAVLIDEVCTMNDGPHS
R8 : ALYTMMKDQYANYVVQKMIDVAEPGQRKIVMHKIRP

[Figure 162]
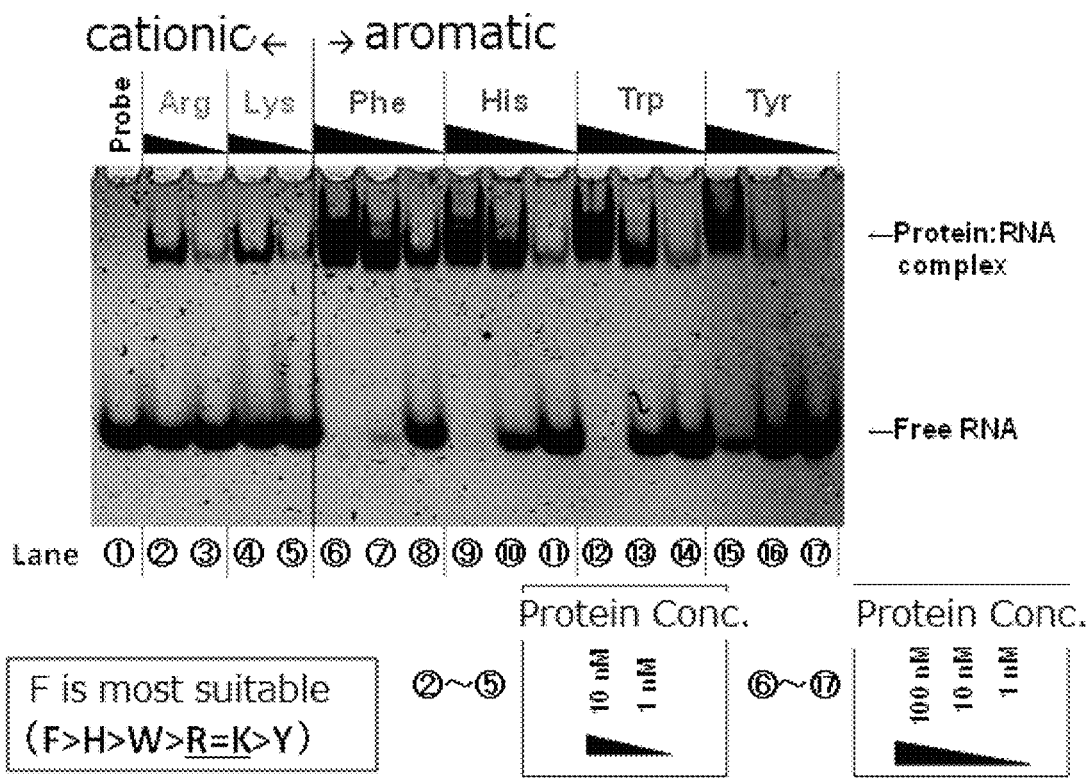
[Figure 163]
Regularity of wild type stacking amino acids
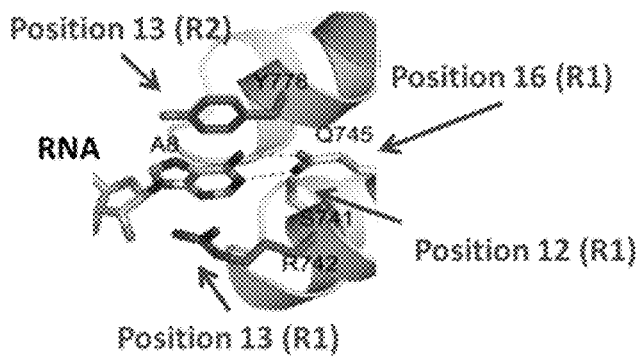
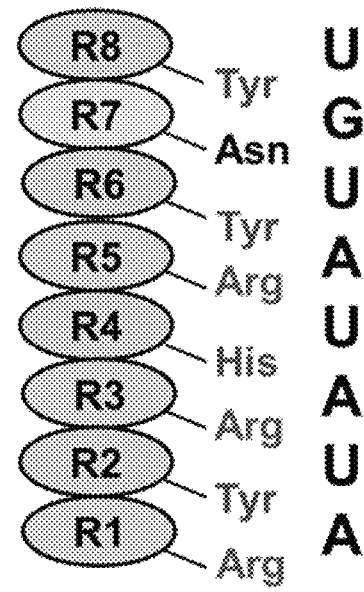

SEQUENCE LISTING

```
<160> NUMBER OF SEQ ID NOS: 169

<210> SEQ ID NO 1
<211> LENGTH: 36
<212> TYPE: PRT
<213> ORGANISM: Homo sapiens

<400> SEQUENCE: 1

His Ile Met Glu Phe Ser Gln Asp Gln His Gly Ser Arg Phe Ile Gln
1               5                   10                  15

Leu Lys Leu Glu Arg Ala Thr Pro Ala Glu Arg Gln Leu Val Phe Asn
            20                  25                  30

Glu Ile Leu Gln
        35

<210> SEQ ID NO 2
<211> LENGTH: 36
<212> TYPE: PRT
<213> ORGANISM: Homo sapiens

<400> SEQUENCE: 2

Ala Ala Tyr Gln Leu Met Val Asp Val Phe Gly Asn Tyr Val Ile Gln
1               5                   10                  15

Lys Phe Phe Glu Phe Gly Ser Leu Glu Gln Lys Leu Ala Leu Ala Glu
            20                  25                  30

Arg Ile Arg Gly
        35

<210> SEQ ID NO 3
<211> LENGTH: 36
<212> TYPE: PRT
<213> ORGANISM: Homo sapiens
```

```
<400> SEQUENCE: 3

His Val Leu Ser Leu Ala Leu Gln Met Tyr Gly Cys Arg Val Ile Gln
1               5                   10                  15

Lys Ala Leu Glu Phe Ile Pro Ser Asp Gln Gln Asn Glu Met Val Arg
            20                  25                  30

Glu Leu Asp Gly
        35

<210> SEQ ID NO 4
<211> LENGTH: 36
<212> TYPE: PRT
<213> ORGANISM: Homo sapiens

<400> SEQUENCE: 4

His Val Leu Lys Cys Val Lys Asp Gln Asn Gly Asn His Val Val Gln
1               5                   10                  15

Lys Cys Ile Glu Cys Val Gln Pro Gln Ser Leu Gln Phe Ile Ile Asp
            20                  25                  30

Ala Phe Lys Gly
        35

<210> SEQ ID NO 5
<211> LENGTH: 36
<212> TYPE: PRT
<213> ORGANISM: Homo sapiens

<400> SEQUENCE: 5

Gln Val Phe Ala Leu Ser Thr His Pro Tyr Gly Cys Arg Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 6
<211> LENGTH: 36
<212> TYPE: PRT
<213> ORGANISM: Homo sapiens

<400> SEQUENCE: 6

His Thr Glu Gln Leu Val Gln Asp Gln Tyr Gly Asn Tyr Val Ile Gln
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 7
<211> LENGTH: 43
<212> TYPE: PRT
<213> ORGANISM: Homo sapiens

<400> SEQUENCE: 7

Asn Val Leu Val Leu Ser Gln His Lys Phe Ala Ser Asn Val Val Glu
1               5                   10                  15

Lys Cys Val Thr His Ala Ser Arg Thr Glu Arg Ala Val Leu Ile Asp
            20                  25                  30

Glu Val Cys Thr Met Asn Asp Gly Pro His Ser
        35                  40
```

```
<210> SEQ ID NO 8
<211> LENGTH: 36
<212> TYPE: PRT
<213> ORGANISM: Homo sapiens

<400> SEQUENCE: 8

Ala Leu Tyr Thr Met Met Lys Asp Gln Tyr Ala Asn Tyr Val Val Gln
 1               5                  10                  15

Lys Met Ile Asp Val Ala Glu Pro Gly Gln Arg Lys Ile Val Met His
             20                  25                  30

Lys Ile Arg Pro
             35

<210> SEQ ID NO 9
<211> LENGTH: 24
<212> TYPE: PRT
<213> ORGANISM: Homo sapiens

<400> SEQUENCE: 9

Gly Arg Ser Arg Leu Leu Glu Asp Phe Arg Asn Asn Arg Tyr Pro Asn
 1               5                  10                  15

Leu Gln Leu Arg Glu Ile Ala Gly
             20

<210> SEQ ID NO 10
<211> LENGTH: 30
<212> TYPE: PRT
<213> ORGANISM: Homo sapiens

<400> SEQUENCE: 10

His Ile Ala Thr Leu Arg Lys Tyr Thr Tyr Gly Lys His Ile Leu Ala
 1               5                  10                  15

Lys Leu Glu Lys Tyr Tyr Met Lys Asn Gly Val Asp Leu Gly
             20                  25                  30

<210> SEQ ID NO 11
<211> LENGTH: 36
<212> TYPE: PRT
<213> ORGANISM: Artificial Sequence
<220> FEATURE:
<223> OTHER INFORMATION: recombinant peptide

<400> SEQUENCE: 11

Gln Val Phe Ala Leu Ser Thr His Pro Tyr Gly Asn Arg Val Ile Gln
 1               5                  10                  15

Arg Ile Leu Glu His Cys Leu Pro Asp Gln Thr Leu Pro Ile Leu Glu
             20                  25                  30

Glu Leu His Gln
             35

<210> SEQ ID NO 12
<211> LENGTH: 36
<212> TYPE: PRT
<213> ORGANISM: Artificial Sequence
<220> FEATURE:
<223> OTHER INFORMATION: recombinant protein

<400> SEQUENCE: 12

Gln Val Phe Ala Leu Ser Thr His Pro Tyr Gly Ser Arg Val Ile Glu
 1               5                  10                  15

Arg Ile Leu Glu His Cys Leu Pro Asp Gln Thr Leu Pro Ile Leu Glu
             20                  25                  30
```

Glu Leu His Gln
        35

<210> SEQ ID NO 13
<211> LENGTH: 36
<212> TYPE: PRT
<213> ORGANISM: Artificial Sequence
<220> FEATURE:
<223> OTHER INFORMATION: recombinant protein

<400> SEQUENCE: 13

Gln Val Phe Ala Leu Ser Thr His Pro Tyr Gly Ser Arg Val Ile Arg
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 14
<211> LENGTH: 36
<212> TYPE: PRT
<213> ORGANISM: Artificial Sequence
<220> FEATURE:
<223> OTHER INFORMATION: recombinant protein

<400> SEQUENCE: 14

His Thr Glu Gln Leu Val Gln Asp Gln Tyr Gly Cys Tyr Val Ile Gln
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 15
<211> LENGTH: 36
<212> TYPE: PRT
<213> ORGANISM: Artificial Sequence
<220> FEATURE:
<223> OTHER INFORMATION: recombinant peptide

<400> SEQUENCE: 15

His Thr Glu Gln Leu Val Gln Asp Gln Tyr Gly Ser Tyr Val Ile Glu
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 16
<211> LENGTH: 36
<212> TYPE: PRT
<213> ORGANISM: Artificial Sequence
<220> FEATURE:
<223> OTHER INFORMATION: recombinant protein

<400> SEQUENCE: 16

His Thr Glu Gln Leu Val Gln Asp Gln Tyr Gly Ser Tyr Val Ile Arg
1               5                   10                  15

His Val Leu Glu His Gly Arg Pro Glu Asp Lys Ser Lys Ile Val Ala
            20                  25                  30

Glu Ile Arg Gly
        35

```
<210> SEQ ID NO 17
<211> LENGTH: 36
<212> TYPE: PRT
<213> ORGANISM: Artificial Sequence
<220> FEATURE:
<223> OTHER INFORMATION: recombinant protein

<400> SEQUENCE: 17

His Thr Glu Gln Leu Val Gln Asp Gln Tyr Gly Asn Tyr Val Ile Gln
1               5                   10                  15

His Val Leu Glu His Gly Arg Pro Glu Asp Lys Ser Lys Ile Val Ala
            20                  25                  30

Ala Phe Lys Gly
        35

<210> SEQ ID NO 18
<211> LENGTH: 36
<212> TYPE: PRT
<213> ORGANISM: Artificial Sequence
<220> FEATURE:
<223> OTHER INFORMATION: recombinant protein

<400> SEQUENCE: 18

His Thr Glu Gln Leu Val Gln Asp Gln Tyr Gly Cys Tyr Val Ile Gln
1               5                   10                  15

His Val Leu Glu His Gly Arg Pro Glu Asp Lys Ser Lys Ile Val Ala
            20                  25                  30

Ala Phe Lys Gly
        35

<210> SEQ ID NO 19
<211> LENGTH: 36
<212> TYPE: PRT
<213> ORGANISM: Artificial Sequence
<220> FEATURE:
<223> OTHER INFORMATION: recombinant protein

<400> SEQUENCE: 19

His Thr Glu Gln Leu Val Gln Asp Gln Tyr Gly Ser Tyr Val Ile Glu
1               5                   10                  15

His Val Leu Glu His Gly Arg Pro Glu Asp Lys Ser Lys Ile Val Ala
            20                  25                  30

Ala Phe Lys Gly
        35

<210> SEQ ID NO 20
<211> LENGTH: 36
<212> TYPE: PRT
<213> ORGANISM: Artificial Sequence
<220> FEATURE:
<223> OTHER INFORMATION: recombinant peptide

<400> SEQUENCE: 20

His Thr Glu Gln Leu Val Gln Asp Gln Tyr Gly Ser Tyr Val Ile Arg
1               5                   10                  15

His Val Leu Glu His Gly Arg Pro Glu Asp Lys Ser Lys Ile Val Ala
            20                  25                  30

Ala Phe Lys Gly
        35

<210> SEQ ID NO 21
```

```
<211> LENGTH: 36
<212> TYPE: PRT
<213> ORGANISM: Artificial Sequence
<220> FEATURE:
<223> OTHER INFORMATION: recombinant peptide

<400> SEQUENCE: 21

Gln Val Phe Ala Leu Ser Thr His Pro Tyr Gly Cys His Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 22
<211> LENGTH: 36
<212> TYPE: PRT
<213> ORGANISM: Artificial Sequence
<220> FEATURE:
<223> OTHER INFORMATION: recombinant peptide

<400> SEQUENCE: 22

Gln Val Phe Ala Leu Ser Thr His Pro Tyr Gly Asn Arg Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 23
<211> LENGTH: 36
<212> TYPE: PRT
<213> ORGANISM: Artificial Sequence
<220> FEATURE:
<223> OTHER INFORMATION: recombinant peptide

<400> SEQUENCE: 23

Gln Val Phe Ala Leu Ser Thr His Pro Tyr Gly Cys Lys Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 24
<211> LENGTH: 36
<212> TYPE: PRT
<213> ORGANISM: Artificial Sequence
<220> FEATURE:
<223> OTHER INFORMATION: recombinant peptide

<400> SEQUENCE: 24

Gln Val Phe Ala Leu Ser Thr His Pro Tyr Gly Cys Phe Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 25
<211> LENGTH: 36
<212> TYPE: PRT
<213> ORGANISM: Artificial Sequence
```

<220> FEATURE:
<223> OTHER INFORMATION: recombinant peptide

<400> SEQUENCE: 25

Gln Val Phe Ala Leu Ser Thr His Pro Tyr Gly Cys Tyr Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 26
<211> LENGTH: 36
<212> TYPE: PRT
<213> ORGANISM: Artificial Sequence
<220> FEATURE:
<223> OTHER INFORMATION: recombinant peptide

<400> SEQUENCE: 26

Gln Val Phe Ala Leu Ser Thr His Pro Tyr Gly Cys Trp Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 27
<211> LENGTH: 36
<212> TYPE: PRT
<213> ORGANISM: Artificial Sequence
<220> FEATURE:
<223> OTHER INFORMATION: recombinant peptide

<400> SEQUENCE: 27

His Thr Glu Gln Leu Val Gln Asp Gln Tyr Gly Asn Trp Val Ile Gln
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 28
<211> LENGTH: 36
<212> TYPE: PRT
<213> ORGANISM: Artificial Sequence
<220> FEATURE:
<223> OTHER INFORMATION: recombinant peptide

<400> SEQUENCE: 28

Asn Val Leu Val Leu Ser Gln His Lys Phe Ala Ser Asn Val Val Glu
1               5                   10                  15

Lys Cys Val Thr His Ala Ser Arg Thr Glu Arg Ala Val Leu Ile Asp
            20                  25                  30

Glu Ile Leu Gln
        35

<210> SEQ ID NO 29
<211> LENGTH: 36
<212> TYPE: PRT
<213> ORGANISM: Artificial Sequence
<220> FEATURE:
<223> OTHER INFORMATION: recombinant peptide

<400> SEQUENCE: 29

Asn Val Leu Val Leu Ser Gln His Lys Phe Ala Ser Asn Val Val Glu
1               5                   10                  15

Lys Cys Val Thr His Ala Ser Arg Thr Glu Arg Ala Val Leu Ile Asp
            20                  25                  30

Glu Ile Arg Gly
        35

<210> SEQ ID NO 30
<211> LENGTH: 19
<212> TYPE: RNA
<213> ORGANISM: Artificial Sequence
<220> FEATURE:
<223> OTHER INFORMATION: primer

<400> SEQUENCE: 30
ccagaauugu auauauucg                                            19

<210> SEQ ID NO 31
<211> LENGTH: 19
<212> TYPE: RNA
<213> ORGANISM: Artificial Sequence
<220> FEATURE:
<223> OTHER INFORMATION: primer

<400> SEQUENCE: 31
ccagaauugu aaauauucg                                            19

<210> SEQ ID NO 32
<211> LENGTH: 19
<212> TYPE: RNA
<213> ORGANISM: Artificial Sequence
<220> FEATURE:
<223> OTHER INFORMATION: primer

<400> SEQUENCE: 32
ccagaauugu uuauauucg                                            19

<210> SEQ ID NO 33
<211> LENGTH: 19
<212> TYPE: RNA
<213> ORGANISM: Artificial Sequence
<220> FEATURE:
<223> OTHER INFORMATION: primer

<400> SEQUENCE: 33
ccagaauuau auauauucg                                            19

<210> SEQ ID NO 34
<211> LENGTH: 19
<212> TYPE: RNA
<213> ORGANISM: Artificial Sequence
<220> FEATURE:
<223> OTHER INFORMATION: primer

<400> SEQUENCE: 34
ccagaauugu aaaaauucg                                            19

<210> SEQ ID NO 35
<211> LENGTH: 21
<212> TYPE: RNA
<213> ORGANISM: Artificial Sequence
<220> FEATURE:
<223> OTHER INFORMATION: primer

```
<400> SEQUENCE: 35
ccagaauugu auauauauuc g                                           21

<210> SEQ ID NO 36
<211> LENGTH: 19
<212> TYPE: RNA
<213> ORGANISM: Artificial Sequence
<220> FEATURE:
<223> OTHER INFORMATION: primer

<400> SEQUENCE: 36
ccagaauagu auauauucg                                              19

<210> SEQ ID NO 37
<211> LENGTH: 23
<212> TYPE: RNA
<213> ORGANISM: Artificial Sequence
<220> FEATURE:
<223> OTHER INFORMATION: primer

<400> SEQUENCE: 37
ccagaauugu auauauauau ucg                                         23

<210> SEQ ID NO 38
<211> LENGTH: 25
<212> TYPE: RNA
<213> ORGANISM: Artificial Sequence
<220> FEATURE:
<223> OTHER INFORMATION: primer

<400> SEQUENCE: 38
ccagaauugu auauauauau auucg                                       25

<210> SEQ ID NO 39
<211> LENGTH: 27
<212> TYPE: RNA
<213> ORGANISM: Artificial Sequence
<220> FEATURE:
<223> OTHER INFORMATION: primer

<400> SEQUENCE: 39
ccagaauugu auauauauau auauucg                                     27

<210> SEQ ID NO 40
<211> LENGTH: 19
<212> TYPE: RNA
<213> ORGANISM: Artificial Sequence
<220> FEATURE:
<223> OTHER INFORMATION: primer

<400> SEQUENCE: 40
ccagaauugu uuuuauucg                                              19

<210> SEQ ID NO 41
<211> LENGTH: 19
<212> TYPE: RNA
<213> ORGANISM: Artificial Sequence
<220> FEATURE:
<223> OTHER INFORMATION: primer

<400> SEQUENCE: 41
ccagaauugu gggguauucg                                             19

<210> SEQ ID NO 42
<211> LENGTH: 19
```

```
<212> TYPE: RNA
<213> ORGANISM: Artificial Sequence
<220> FEATURE:
<223> OTHER INFORMATION: primer

<400> SEQUENCE: 42
ccagaauugu cccuauucg                                                       19

<210> SEQ ID NO 43
<211> LENGTH: 19
<212> TYPE: RNA
<213> ORGANISM: Artificial Sequence
<220> FEATURE:
<223> OTHER INFORMATION: primer

<400> SEQUENCE: 43
ccagaauuga aaauauucg                                                       19

<210> SEQ ID NO 44
<211> LENGTH: 19
<212> TYPE: RNA
<213> ORGANISM: Artificial Sequence
<220> FEATURE:
<223> OTHER INFORMATION: primer

<400> SEQUENCE: 44
ccagaauugg agauauucg                                                       19

<210> SEQ ID NO 45
<211> LENGTH: 19
<212> TYPE: RNA
<213> ORGANISM: Artificial Sequence
<220> FEATURE:
<223> OTHER INFORMATION: primer

<400> SEQUENCE: 45
ccagaauugc acauauucg                                                       19

<210> SEQ ID NO 46
<211> LENGTH: 21
<212> TYPE: RNA
<213> ORGANISM: Artificial Sequence
<220> FEATURE:
<223> OTHER INFORMATION: primer

<400> SEQUENCE: 46
ccagaauugc acacauauuc g                                                    21

<210> SEQ ID NO 47
<211> LENGTH: 21
<212> TYPE: RNA
<213> ORGANISM: Artificial Sequence
<220> FEATURE:
<223> OTHER INFORMATION: primer

<400> SEQUENCE: 47
ccagaauugg agagauauuc g                                                    21

<210> SEQ ID NO 48
<211> LENGTH: 20
<212> TYPE: RNA
<213> ORGANISM: Artificial Sequence
<220> FEATURE:
<223> OTHER INFORMATION: primer

<400> SEQUENCE: 48
```
ccagaauugu auauuauucg     20

<210> SEQ ID NO 49
<211> LENGTH: 20
<212> TYPE: RNA
<213> ORGANISM: Artificial Sequence
<220> FEATURE:
<223> OTHER INFORMATION: primer

<400> SEQUENCE: 49
ccagaauugu auaauauucg     20

<210> SEQ ID NO 50
<211> LENGTH: 20
<212> TYPE: RNA
<213> ORGANISM: Artificial Sequence
<220> FEATURE:
<223> OTHER INFORMATION: primer

<400> SEQUENCE: 50
ccagaauugu uauauauucg     20

<210> SEQ ID NO 51
<211> LENGTH: 19
<212> TYPE: RNA
<213> ORGANISM: Artificial Sequence
<220> FEATURE:
<223> OTHER INFORMATION: primer

<400> SEQUENCE: 51
ccagaauugu auauuucg     19

<210> SEQ ID NO 52
<211> LENGTH: 19
<212> TYPE: RNA
<213> ORGANISM: Artificial Sequence
<220> FEATURE:
<223> OTHER INFORMATION: primer

<400> SEQUENCE: 52
ccagaauugu auauguucg     19

<210> SEQ ID NO 53
<211> LENGTH: 19
<212> TYPE: RNA
<213> ORGANISM: Artificial Sequence
<220> FEATURE:
<223> OTHER INFORMATION: primer

<400> SEQUENCE: 53
ccagaauugu auaucuucg     19

<210> SEQ ID NO 54
<211> LENGTH: 19
<212> TYPE: RNA
<213> ORGANISM: Artificial Sequence
<220> FEATURE:
<223> OTHER INFORMATION: primer

<400> SEQUENCE: 54
ccagaauugu auaaauucg     19

<210> SEQ ID NO 55
<211> LENGTH: 19
<212> TYPE: RNA
<213> ORGANISM: Artificial Sequence

```
<220> FEATURE:
<223> OTHER INFORMATION: primer

<400> SEQUENCE: 55
ccagaauugu auagauucg                                              19

<210> SEQ ID NO 56
<211> LENGTH: 19
<212> TYPE: RNA
<213> ORGANISM: Artificial Sequence
<220> FEATURE:
<223> OTHER INFORMATION: primer

<400> SEQUENCE: 56
ccagaauugu auacauucg                                              19

<210> SEQ ID NO 57
<211> LENGTH: 19
<212> TYPE: RNA
<213> ORGANISM: Artificial Sequence
<220> FEATURE:
<223> OTHER INFORMATION: primer

<400> SEQUENCE: 57
ccagaauuuu auauauucg                                              19

<210> SEQ ID NO 58
<211> LENGTH: 19
<212> TYPE: RNA
<213> ORGANISM: Artificial Sequence
<220> FEATURE:
<223> OTHER INFORMATION: primer

<400> SEQUENCE: 58
ccagaauucu auauauucg                                              19

<210> SEQ ID NO 59
<211> LENGTH: 19
<212> TYPE: RNA
<213> ORGANISM: Artificial Sequence
<220> FEATURE:
<223> OTHER INFORMATION: primer

<400> SEQUENCE: 59
ccagaauggu auauauucg                                              19

<210> SEQ ID NO 60
<211> LENGTH: 19
<212> TYPE: RNA
<213> ORGANISM: Artificial Sequence
<220> FEATURE:
<223> OTHER INFORMATION: primer

<400> SEQUENCE: 60
ccagaaucgu auauauucg                                              19

<210> SEQ ID NO 61
<211> LENGTH: 21
<212> TYPE: RNA
<213> ORGANISM: Artificial Sequence
<220> FEATURE:
<223> OTHER INFORMATION: primer

<400> SEQUENCE: 61
ccagaauugc gcgcguauuc g                                           21
```

<210> SEQ ID NO 62
<211> LENGTH: 21
<212> TYPE: RNA
<213> ORGANISM: Artificial Sequence
<220> FEATURE:
<223> OTHER INFORMATION: primer

<400> SEQUENCE: 62
ccagaauugu cucucuauuc g                                              21

<210> SEQ ID NO 63
<211> LENGTH: 36
<212> TYPE: PRT
<213> ORGANISM: Artificial Sequence
<220> FEATURE:
<223> OTHER INFORMATION: recombinant peptide

<400> SEQUENCE: 63

His Ile Met Glu Ala Ser Gln Asp Gln His Gly Ser Arg Phe Ile Gln
1               5                   10                  15

Leu Lys Leu Glu Arg Ala Thr Pro Ala Glu Arg Gln Leu Val Phe Asn
            20                  25                  30

Glu Ile Leu Gln
        35

<210> SEQ ID NO 64
<211> LENGTH: 36
<212> TYPE: PRT
<213> ORGANISM: Artificial Sequence
<220> FEATURE:
<223> OTHER INFORMATION: recombinant peptide

<400> SEQUENCE: 64

His Ile Met Glu Phe Ser Gln Asp Gln His Gly Ser Arg Ala Ile Gln
1               5                   10                  15

Leu Lys Leu Glu Arg Ala Thr Pro Ala Glu Arg Gln Leu Val Phe Asn
            20                  25                  30

Glu Ile Leu Gln
        35

<210> SEQ ID NO 65
<211> LENGTH: 36
<212> TYPE: PRT
<213> ORGANISM: Artificial Sequence
<220> FEATURE:
<223> OTHER INFORMATION: recombinant peptide

<400> SEQUENCE: 65

His Ile Met Glu Ala Ser Gln Asp Gln His Gly Ser Arg Ala Ile Gln
1               5                   10                  15

Leu Lys Leu Glu Arg Ala Thr Pro Ala Glu Arg Gln Leu Val Phe Asn
            20                  25                  30

Glu Ile Leu Gln
        35

<210> SEQ ID NO 66
<211> LENGTH: 36
<212> TYPE: PRT
<213> ORGANISM: Artificial Sequence
<220> FEATURE:
<223> OTHER INFORMATION: recombinant peptide

<400> SEQUENCE: 66

```
Ala Ala Tyr Gln Leu Met Val Asp Val Phe Gly Asn Tyr Val Ile Gln
1               5                   10                  15

Lys Ala Phe Glu Phe Gly Ser Leu Glu Gln Lys Leu Ala Leu Ala Glu
                20                  25                  30

Arg Ile Arg Gly
            35
```

<210> SEQ ID NO 67
<211> LENGTH: 36
<212> TYPE: PRT
<213> ORGANISM: Artificial Sequence
<220> FEATURE:
<223> OTHER INFORMATION: recombinant peptide

<400> SEQUENCE: 67

```
Gln Val Phe Ala Leu Ser Thr His Pro Tyr Gly Cys His Val Ile Gln
1               5                   10                  15

Arg Ile Leu Glu His Cys Leu Pro Asp Gln Thr Leu Pro Ile Leu Glu
                20                  25                  30

Glu Leu His Gln
            35
```

<210> SEQ ID NO 68
<211> LENGTH: 36
<212> TYPE: PRT
<213> ORGANISM: Artificial Sequence
<220> FEATURE:
<223> OTHER INFORMATION: recombinant peptide

<400> SEQUENCE: 68

```
His Thr Glu Gln Leu Val Gln Asp Gln Tyr Gly Asn Arg Val Ile Gln
1               5                   10                  15

His Val Leu Glu His Gly Arg Pro Glu Asp Lys Ser Lys Ile Val Ala
                20                  25                  30

Glu Ile Arg Gly
            35
```

<210> SEQ ID NO 69
<211> LENGTH: 36
<212> TYPE: PRT
<213> ORGANISM: Artificial Sequence
<220> FEATURE:
<223> OTHER INFORMATION: recombinant peptide

<400> SEQUENCE: 69

```
Gln Val Phe Ala Leu Ser Thr His Pro Tyr Gly Cys Arg Val Ile Gln
1               5                   10                  15

Arg Ile Leu Glu His Cys Leu Pro Asp Gln Thr Leu Pro Ile Leu Glu
                20                  25                  30

Glu Ile Leu Gln
            35
```

<210> SEQ ID NO 70
<211> LENGTH: 36
<212> TYPE: PRT
<213> ORGANISM: Artificial Sequence
<220> FEATURE:
<223> OTHER INFORMATION: recombinant peptide

<400> SEQUENCE: 70

```
His Thr Glu Gln Leu Val Gln Asp Gln Tyr Gly Asn Tyr Val Ile Gln
1               5                   10                  15
```

His Val Leu Glu His Gly Arg Pro Glu Asp Lys Ser Lys Ile Val Ala
            20                  25                  30

Glu Ile Arg Pro
        35

<210> SEQ ID NO 71
<211> LENGTH: 36
<212> TYPE: PRT
<213> ORGANISM: Artificial Sequence
<220> FEATURE:
<223> OTHER INFORMATION: recombinant peptide

<400> SEQUENCE: 71

Asn Val Leu Val Leu Ser Gln His Lys Phe Ala Ser Asn Val Val Glu
1               5                   10                  15

Lys Cys Val Thr His Ala Ser Arg Thr Glu Arg Ala Val Leu Ile Asp
            20                  25                  30

Glu Ile Leu Gln
        35

<210> SEQ ID NO 72
<211> LENGTH: 36
<212> TYPE: PRT
<213> ORGANISM: Artificial Sequence
<220> FEATURE:
<223> OTHER INFORMATION: recombinant peptide

<400> SEQUENCE: 72

Asn Val Leu Val Leu Ser Gln His Lys Phe Ala Ser Asn Val Val Glu
1               5                   10                  15

Lys Cys Val Thr His Ala Ser Arg Thr Glu Arg Ala Val Leu Ile Asp
            20                  25                  30

Glu Ile Arg Gly
        35

<210> SEQ ID NO 73
<211> LENGTH: 36
<212> TYPE: PRT
<213> ORGANISM: Artificial Sequence
<220> FEATURE:
<223> OTHER INFORMATION: recombinant peptide

<400> SEQUENCE: 73

His Val Leu Gln Leu Ser Gln Asp Gln Tyr Gly Cys Arg Val Ile Gln
1               5                   10                  15

Lys Ile Leu Glu His Ala Thr Pro Glu Gln Arg Gln Leu Ile Val Asp
            20                  25                  30

Glu Ile Arg Gly
        35

<210> SEQ ID NO 74
<211> LENGTH: 36
<212> TYPE: PRT
<213> ORGANISM: Artificial Sequence
<220> FEATURE:
<223> OTHER INFORMATION: recombinant peptide

<400> SEQUENCE: 74

His Val Leu Ala Leu Ser Gln Asp Gln Tyr Gly Cys Arg Val Ile Gln
1               5                   10                  15

Lys Ile Leu Glu His Ala Leu Pro Asp Gln Arg Leu Leu Ile Val Glu
            20                  25                  30

Glu Ile Arg Gly
        35

<210> SEQ ID NO 75
<211> LENGTH: 36
<212> TYPE: PRT
<213> ORGANISM: Artificial Sequence
<220> FEATURE:
<223> OTHER INFORMATION: recombinant peptide

<400> SEQUENCE: 75

Gln Val Phe Ala Leu Ser Thr His Pro Tyr Gly Asn Arg Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 76
<211> LENGTH: 36
<212> TYPE: PRT
<213> ORGANISM: Artificial Sequence
<220> FEATURE:
<223> OTHER INFORMATION: recombinant peptide

<400> SEQUENCE: 76

Gln Val Phe Ala Leu Ser Thr His Pro Tyr Gly Ser Arg Val Ile Glu
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 77
<211> LENGTH: 36
<212> TYPE: PRT
<213> ORGANISM: Artificial Sequence
<220> FEATURE:
<223> OTHER INFORMATION: recombinant peptide

<400> SEQUENCE: 77

Gln Val Phe Ala Leu Ser Thr His Pro Tyr Gly Ser Arg Val Ile Arg
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 78
<211> LENGTH: 36
<212> TYPE: PRT
<213> ORGANISM: Artificial Sequence
<220> FEATURE:
<223> OTHER INFORMATION: recombinant peptide

<400> SEQUENCE: 78

His Thr Glu Gln Leu Val Gln Asp Gln Tyr Gly Cys Tyr Val Ile Gln
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 79
<211> LENGTH: 36
<212> TYPE: PRT
<213> ORGANISM: Artificial Sequence
<220> FEATURE:
<223> OTHER INFORMATION: recombinant peptide

<400> SEQUENCE: 79

```
His Thr Glu Gln Leu Val Gln Asp Gln Tyr Gly Ser Tyr Val Ile Glu
1               5                   10                  15

His Val Leu Glu His Gly Arg Pro Glu Asp Lys Ser Lys Ile Val Ala
            20                  25                  30

Glu Ile Arg Gly
        35
```

<210> SEQ ID NO 80
<211> LENGTH: 36
<212> TYPE: PRT
<213> ORGANISM: Artificial Sequence
<220> FEATURE:
<223> OTHER INFORMATION: recombinant peptide

<400> SEQUENCE: 80

```
His Thr Glu Gln Leu Val Gln Asp Gln Tyr Gly Ser Tyr Val Ile Arg
1               5                   10                  15

His Val Leu Glu His Gly Arg Pro Glu Asp Lys Ser Lys Ile Val Ala
            20                  25                  30

Glu Ile Arg Gly
        35
```

<210> SEQ ID NO 81
<211> LENGTH: 36
<212> TYPE: PRT
<213> ORGANISM: Artificial Sequence
<220> FEATURE:
<223> OTHER INFORMATION: recombinant peptide

<400> SEQUENCE: 81

```
Gln Val Phe Ala Leu Ser Thr His Pro Tyr Gly Cys Lys Val Ile Gln
1               5                   10                  15

Arg Ile Leu Glu His Cys Leu Pro Asp Gln Thr Leu Pro Ile Leu Glu
            20                  25                  30

Glu Leu His Gln
        35
```

<210> SEQ ID NO 82
<211> LENGTH: 36
<212> TYPE: PRT
<213> ORGANISM: Artificial Sequence
<220> FEATURE:
<223> OTHER INFORMATION: recombinant peptide

<400> SEQUENCE: 82

```
His Thr Glu Gln Leu Val Gln Asp Gln Tyr Gly Asn Phe Val Ile Gln
1               5                   10                  15

His Val Leu Glu His Gly Arg Pro Glu Asp Lys Ser Lys Ile Val Ala
            20                  25                  30

Glu Ile Arg Gly
        35
```

<210> SEQ ID NO 83
<211> LENGTH: 36

```
<212> TYPE: PRT
<213> ORGANISM: Artificial Sequence
<220> FEATURE:
<223> OTHER INFORMATION: recombinant peptide

<400> SEQUENCE: 83

His Thr Glu Gln Leu Val Gln Asp Gln Tyr Gly Asn His Val Ile Gln
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 84
<211> LENGTH: 36
<212> TYPE: PRT
<213> ORGANISM: Artificial Sequence
<220> FEATURE:
<223> OTHER INFORMATION: recombinant peptide

<400> SEQUENCE: 84

His Thr Glu Gln Leu Val Gln Asp Gln Tyr Gly Asn Trp Val Ile Gln
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 85
<211> LENGTH: 36
<212> TYPE: PRT
<213> ORGANISM: Artificial Sequence
<220> FEATURE:
<223> OTHER INFORMATION: recombinant peptide

<400> SEQUENCE: 85

Gln Val Phe Ala Leu Ser Thr His Pro Tyr Gly Cys His Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 86
<211> LENGTH: 36
<212> TYPE: PRT
<213> ORGANISM: Artificial Sequence
<220> FEATURE:
<223> OTHER INFORMATION: recombinant peptide

<400> SEQUENCE: 86

Gln Val Phe Ala Leu Ser Thr His Pro Tyr Gly Cys Phe Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 87
<211> LENGTH: 36
<212> TYPE: PRT
<213> ORGANISM: Artificial Sequence
<220> FEATURE:
```

```
<223> OTHER INFORMATION: recombinant peptide

<400> SEQUENCE: 87

Gln Val Phe Ala Leu Ser Thr His Pro Tyr Gly Cys Tyr Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 88
<211> LENGTH: 36
<212> TYPE: PRT
<213> ORGANISM: Artificial Sequence
<220> FEATURE:
<223> OTHER INFORMATION: recombinant peptide

<400> SEQUENCE: 88

Gln Val Phe Ala Leu Ser Thr His Pro Tyr Gly Cys Trp Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 89
<211> LENGTH: 36
<212> TYPE: PRT
<213> ORGANISM: Artificial Sequence
<220> FEATURE:
<223> OTHER INFORMATION: recombinant peptide

<400> SEQUENCE: 89

Gln Val Phe Ala Leu Ser Thr His Pro Tyr Gly Cys Lys Val Ile Gln
1               5                   10                  15

Lys Ile Leu Glu His Cys Leu Pro Asp Gln Thr Leu Pro Ile Leu Glu
            20                  25                  30

Glu Leu His Gln
        35

<210> SEQ ID NO 90
<211> LENGTH: 36
<212> TYPE: PRT
<213> ORGANISM: Artificial Sequence
<220> FEATURE:
<223> OTHER INFORMATION: recombinant peptide

<400> SEQUENCE: 90

Gln Val Phe Ala Leu Ser Thr His Pro Tyr Gly Cys Arg Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 91
<211> LENGTH: 36
<212> TYPE: PRT
<213> ORGANISM: Artificial Sequence
<220> FEATURE:
<223> OTHER INFORMATION: recombinant peptide

<400> SEQUENCE: 91
```

His Thr Glu Gln Leu Val Gln Asp Gln Tyr Gly Ser Tyr Val Ile Arg
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 92
<211> LENGTH: 36
<212> TYPE: PRT
<213> ORGANISM: Artificial Sequence
<220> FEATURE:
<223> OTHER INFORMATION: recombinant peptide

<400> SEQUENCE: 92

His Thr Glu Gln Leu Val Gln Asp Gln Tyr Gly Ser Arg Val Ile Arg
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 93
<211> LENGTH: 36
<212> TYPE: PRT
<213> ORGANISM: Artificial Sequence
<220> FEATURE:
<223> OTHER INFORMATION: recombinant peptide

<400> SEQUENCE: 93

Gln Val Phe Ala Leu Ser Thr His Pro Tyr Gly Cys Tyr Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 94
<211> LENGTH: 36
<212> TYPE: PRT
<213> ORGANISM: Artificial Sequence
<220> FEATURE:
<223> OTHER INFORMATION: recombinant peptide

<400> SEQUENCE: 94

His Thr Glu Gln Leu Val Gln Asp Gln Tyr Gly Ser Tyr Val Ile Glu
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 95
<211> LENGTH: 36
<212> TYPE: PRT
<213> ORGANISM: Artificial Sequence
<220> FEATURE:
<223> OTHER INFORMATION: recombinant peptide

<400> SEQUENCE: 95

His Thr Glu Gln Leu Val Gln Asp Gln Tyr Gly Ser Arg Val Ile Glu
1               5                   10                  15

```
His Val Leu Glu His Gly Arg Pro Glu Asp Lys Ser Lys Ile Val Ala
            20                  25                  30

Glu Ile Arg Gly
        35

<210> SEQ ID NO 96
<211> LENGTH: 36
<212> TYPE: PRT
<213> ORGANISM: Artificial Sequence
<220> FEATURE:
<223> OTHER INFORMATION: recombinant peptide

<400> SEQUENCE: 96

Gln Val Phe Ala Leu Ser Thr His Pro Tyr Gly Ser Arg Val Ile Glu
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 97
<211> LENGTH: 36
<212> TYPE: PRT
<213> ORGANISM: Artificial Sequence
<220> FEATURE:
<223> OTHER INFORMATION: recombinant peptide

<400> SEQUENCE: 97

His Thr Glu Gln Leu Val Gln Asp Gln Tyr Gly Asn Tyr Val Ile Gln
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 98
<211> LENGTH: 36
<212> TYPE: PRT
<213> ORGANISM: Artificial Sequence
<220> FEATURE:
<223> OTHER INFORMATION: recombinant peptide

<400> SEQUENCE: 98

His Thr Glu Gln Leu Val Gln Asp Gln Tyr Gly Asn Arg Val Ile Gln
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 99
<211> LENGTH: 36
<212> TYPE: PRT
<213> ORGANISM: Artificial Sequence
<220> FEATURE:
<223> OTHER INFORMATION: recombinant peptide

<400> SEQUENCE: 99

Glu Leu His Gln His Thr Glu Gln Leu Val Gln Asp Gln Tyr Gly Cys
1               5                   10                  15

Tyr Val Ile Gln His Val Leu Glu His Gly Arg Pro Glu Asp Lys Ser
            20                  25                  30
```

```
Lys Ile Val Ala
        35

<210> SEQ ID NO 100
<211> LENGTH: 40
<212> TYPE: PRT
<213> ORGANISM: Artificial Sequence
<220> FEATURE:
<223> OTHER INFORMATION: recombinant peptide

<400> SEQUENCE: 100

Glu Ile Arg Gly Gln Val Phe Ala Leu Ser Thr His Pro Tyr Gly Cys
1               5                   10                  15

Arg Val Ile Gln Arg Ile Leu Glu His Cys Leu Pro Asp Gln Thr Leu
            20                  25                  30

Pro Ile Leu Glu Glu Leu His Gln
        35                  40

<210> SEQ ID NO 101
<211> LENGTH: 40
<212> TYPE: PRT
<213> ORGANISM: Artificial Sequence
<220> FEATURE:
<223> OTHER INFORMATION: recombinant peptide

<400> SEQUENCE: 101

Ala Phe Lys Gly Gln Val Phe Ala Leu Ser Thr His Pro Tyr Gly Cys
1               5                   10                  15

Arg Val Ile Gln Arg Ile Leu Glu His Cys Leu Pro Asp Gln Thr Leu
            20                  25                  30

Pro Ile Leu Glu Glu Leu His Gln
        35                  40

<210> SEQ ID NO 102
<211> LENGTH: 36
<212> TYPE: PRT
<213> ORGANISM: Artificial Sequence
<220> FEATURE:
<223> OTHER INFORMATION: recombinant peptide

<400> SEQUENCE: 102

His Ile Met Glu Phe Ser Gln Asp Gln His Gly Asn Arg Phe Ile Gln
1               5                   10                  15

Leu Lys Leu Glu Arg Ala Thr Pro Ala Glu Arg Gln Leu Val Phe Asn
            20                  25                  30

Glu Ile Leu Gln
        35

<210> SEQ ID NO 103
<211> LENGTH: 36
<212> TYPE: PRT
<213> ORGANISM: Artificial Sequence
<220> FEATURE:
<223> OTHER INFORMATION: recombinant peptide

<400> SEQUENCE: 103

His Ile Met Glu Phe Ser Gln Asp Gln His Gly Ser Arg Phe Ile Glu
1               5                   10                  15

Leu Lys Leu Glu Arg Ala Thr Pro Ala Glu Arg Gln Leu Val Phe Asn
            20                  25                  30

Glu Ile Leu Gln
        35
```

```
<210> SEQ ID NO 104
<211> LENGTH: 36
<212> TYPE: PRT
<213> ORGANISM: Artificial Sequence
<220> FEATURE:
<223> OTHER INFORMATION: recombinant peptide

<400> SEQUENCE: 104

His Ile Met Glu Phe Ser Gln Asp Gln His Gly Ser Arg Phe Ile Arg
1               5                   10                  15

Leu Lys Leu Glu Arg Ala Thr Pro Ala Glu Arg Gln Leu Val Phe Asn
            20                  25                  30

Glu Ile Leu Gln
        35

<210> SEQ ID NO 105
<211> LENGTH: 36
<212> TYPE: PRT
<213> ORGANISM: Artificial Sequence
<220> FEATURE:
<223> OTHER INFORMATION: recombinant peptide

<400> SEQUENCE: 105

Ala Ala Tyr Gln Leu Met Val Asp Val Phe Gly Cys Tyr Val Ile Gln
1               5                   10                  15

Lys Phe Phe Glu Phe Gly Ser Leu Glu Gln Lys Leu Ala Leu Ala Glu
            20                  25                  30

Arg Ile Arg Gly
        35

<210> SEQ ID NO 106
<211> LENGTH: 36
<212> TYPE: PRT
<213> ORGANISM: Artificial Sequence
<220> FEATURE:
<223> OTHER INFORMATION: recombinant peptide

<400> SEQUENCE: 106

Ala Ala Tyr Gln Leu Met Val Asp Val Phe Gly Ser Tyr Val Ile Gln
1               5                   10                  15

Lys Phe Phe Glu Phe Gly Ser Leu Glu Gln Lys Leu Ala Leu Ala Glu
            20                  25                  30

Arg Ile Arg Gly
        35

<210> SEQ ID NO 107
<211> LENGTH: 36
<212> TYPE: PRT
<213> ORGANISM: Artificial Sequence
<220> FEATURE:
<223> OTHER INFORMATION: recombinant peptide

<400> SEQUENCE: 107

Ala Ala Tyr Gln Leu Met Val Asp Val Phe Gly Ser Tyr Val Ile Glu
1               5                   10                  15

Lys Phe Phe Glu Phe Gly Ser Leu Glu Gln Lys Leu Ala Leu Ala Glu
            20                  25                  30

Arg Ile Arg Gly
        35

<210> SEQ ID NO 108
```

<211> LENGTH: 36
<212> TYPE: PRT
<213> ORGANISM: Artificial Sequence
<220> FEATURE:
<223> OTHER INFORMATION: recombinant peptide

<400> SEQUENCE: 108

```
Ala Ala Tyr Gln Leu Met Val Asp Val Phe Gly Ser Tyr Val Ile Arg
1               5                   10                  15
Lys Phe Phe Glu Phe Gly Ser Leu Glu Gln Lys Leu Ala Leu Ala Glu
            20                  25                  30
Arg Ile Arg Gly
        35
```

<210> SEQ ID NO 109
<211> LENGTH: 36
<212> TYPE: PRT
<213> ORGANISM: Artificial Sequence
<220> FEATURE:
<223> OTHER INFORMATION: recombinant peptide

<400> SEQUENCE: 109

```
Ala Ala Tyr Gln Leu Met Val Asp Val Phe Gly Cys Tyr Val Ile Gln
1               5                   10                  15
Lys Phe Phe Glu Phe Gly Ser Leu Glu Gln Lys Leu Ala Leu Ala Glu
            20                  25                  30
Arg Ile Arg Gly
        35
```

<210> SEQ ID NO 110
<211> LENGTH: 36
<212> TYPE: PRT
<213> ORGANISM: Artificial Sequence
<220> FEATURE:
<223> OTHER INFORMATION: recombinant peptide

<400> SEQUENCE: 110

```
Ala Ala Tyr Gln Leu Met Val Asp Val Phe Gly Ser Tyr Val Ile Glu
1               5                   10                  15
Lys Phe Phe Glu Phe Gly Ser Leu Glu Gln Lys Leu Ala Leu Ala Glu
            20                  25                  30
Arg Ile Arg Gly
        35
```

<210> SEQ ID NO 111
<211> LENGTH: 36
<212> TYPE: PRT
<213> ORGANISM: Artificial Sequence
<220> FEATURE:
<223> OTHER INFORMATION: recombinant peptide

<400> SEQUENCE: 111

```
Ala Ala Tyr Gln Leu Met Val Asp Val Phe Gly Ser Tyr Val Ile Arg
1               5                   10                  15
Lys Phe Phe Glu Phe Gly Ser Leu Glu Gln Lys Leu Ala Leu Ala Glu
            20                  25                  30
Arg Ile Arg Gly
        35
```

<210> SEQ ID NO 112
<211> LENGTH: 43
<212> TYPE: PRT
<213> ORGANISM: Artificial Sequence
<220> FEATURE:
<223> OTHER INFORMATION: recombinant peptide

<400> SEQUENCE: 112

Asn Val Leu Val Leu Ser Gln His Lys Phe Ala Cys Asn Val Val Gln
1               5                   10                  15

Lys Cys Val Thr His Ala Ser Arg Thr Glu Arg Ala Val Leu Ile Asp
            20                  25                  30

Glu Val Cys Thr Met Asn Asp Gly Pro His Ser
        35                  40

<210> SEQ ID NO 113
<211> LENGTH: 43
<212> TYPE: PRT
<213> ORGANISM: Artificial Sequence
<220> FEATURE:
<223> OTHER INFORMATION: recombinant peptide

<400> SEQUENCE: 113

Asn Val Leu Val Leu Ser Gln His Lys Phe Ala Ser Asn Val Val Gln
1               5                   10                  15

Lys Cys Val Thr His Ala Ser Arg Thr Glu Arg Ala Val Leu Ile Asp
            20                  25                  30

Glu Val Cys Thr Met Asn Asp Gly Pro His Ser
        35                  40

<210> SEQ ID NO 114
<211> LENGTH: 43
<212> TYPE: PRT
<213> ORGANISM: Artificial Sequence
<220> FEATURE:
<223> OTHER INFORMATION: recombinant peptide

<400> SEQUENCE: 114

Asn Val Leu Val Leu Ser Gln His Lys Phe Ala Asn Asn Val Val Gln
1               5                   10                  15

Lys Cys Val Thr His Ala Ser Arg Thr Glu Arg Ala Val Leu Ile Asp
            20                  25                  30

Glu Val Cys Thr Met Asn Asp Gly Pro His Ser
        35                  40

<210> SEQ ID NO 115
<211> LENGTH: 43
<212> TYPE: PRT
<213> ORGANISM: Artificial Sequence
<220> FEATURE:
<223> OTHER INFORMATION: recombinant peptide

<400> SEQUENCE: 115

Asn Val Leu Val Leu Ser Gln His Lys Phe Ala Ser Asn Val Val Arg
1               5                   10                  15

Lys Cys Val Thr His Ala Ser Arg Thr Glu Arg Ala Val Leu Ile Asp
            20                  25                  30

Glu Val Cys Thr Met Asn Asp Gly Pro His Ser
        35                  40

<210> SEQ ID NO 116
<211> LENGTH: 43
<212> TYPE: PRT
<213> ORGANISM: Artificial Sequence
<220> FEATURE:
<223> OTHER INFORMATION: recombinant peptide

```
<400> SEQUENCE: 116

Asn Val Leu Val Leu Ser Gln His Lys Phe Ala Cys Asn Val Val Gln
1               5                   10                  15

Lys Cys Val Thr His Ala Ser Arg Thr Glu Arg Ala Val Leu Ile Asp
            20                  25                  30

Glu Val Cys Thr Met Asn Asp Gly Pro His Ser
        35                  40

<210> SEQ ID NO 117
<211> LENGTH: 43
<212> TYPE: PRT
<213> ORGANISM: Artificial Sequence
<220> FEATURE:
<223> OTHER INFORMATION: recombinant peptide

<400> SEQUENCE: 117

Asn Val Leu Val Leu Ser Gln His Lys Phe Ala Asn Asn Val Val Gln
1               5                   10                  15

Lys Cys Val Thr His Ala Ser Arg Thr Glu Arg Ala Val Leu Ile Asp
            20                  25                  30

Glu Val Cys Thr Met Asn Asp Gly Pro His Ser
        35                  40

<210> SEQ ID NO 118
<211> LENGTH: 43
<212> TYPE: PRT
<213> ORGANISM: Artificial Sequence
<220> FEATURE:
<223> OTHER INFORMATION: recombinant peptide

<400> SEQUENCE: 118

Asn Val Leu Val Leu Ser Gln His Lys Phe Ala Ser Asn Val Val Arg
1               5                   10                  15

Lys Cys Val Thr His Ala Ser Arg Thr Glu Arg Ala Val Leu Ile Asp
            20                  25                  30

Glu Val Cys Thr Met Asn Asp Gly Pro His Ser
        35                  40

<210> SEQ ID NO 119
<211> LENGTH: 36
<212> TYPE: PRT
<213> ORGANISM: Artificial Sequence
<220> FEATURE:
<223> OTHER INFORMATION: recombinant peptide

<400> SEQUENCE: 119

Ala Leu Tyr Thr Met Met Lys Asp Gln Tyr Ala Cys Tyr Val Val Gln
1               5                   10                  15

Lys Met Ile Asp Val Ala Glu Pro Gly Gln Arg Lys Ile Val Met His
            20                  25                  30

Lys Ile Arg Pro
        35

<210> SEQ ID NO 120
<211> LENGTH: 36
<212> TYPE: PRT
<213> ORGANISM: Artificial Sequence
<220> FEATURE:
<223> OTHER INFORMATION: recombinant peptide

<400> SEQUENCE: 120

Ala Leu Tyr Thr Met Met Lys Asp Gln Tyr Ala Ser Tyr Val Val Gln
```

```
1               5                   10                  15
Lys Met Ile Asp Val Ala Glu Pro Gly Gln Arg Lys Ile Val Met His
            20                  25                  30

Lys Ile Arg Pro
        35

<210> SEQ ID NO 121
<211> LENGTH: 36
<212> TYPE: PRT
<213> ORGANISM: Artificial Sequence
<220> FEATURE:
<223> OTHER INFORMATION: recombinant peptide

<400> SEQUENCE: 121

Ala Leu Tyr Thr Met Met Lys Asp Gln Tyr Ala Ser Tyr Val Val Glu
1               5                   10                  15

Lys Met Ile Asp Val Ala Glu Pro Gly Gln Arg Lys Ile Val Met His
            20                  25                  30

Lys Ile Arg Pro
        35

<210> SEQ ID NO 122
<211> LENGTH: 36
<212> TYPE: PRT
<213> ORGANISM: Artificial Sequence
<220> FEATURE:
<223> OTHER INFORMATION: recombinant peptide

<400> SEQUENCE: 122

Ala Leu Tyr Thr Met Met Lys Asp Gln Tyr Ala Ser Tyr Val Val Arg
1               5                   10                  15

Lys Met Ile Asp Val Ala Glu Pro Gly Gln Arg Lys Ile Val Met His
            20                  25                  30

Lys Ile Arg Pro
        35

<210> SEQ ID NO 123
<211> LENGTH: 36
<212> TYPE: PRT
<213> ORGANISM: Artificial Sequence
<220> FEATURE:
<223> OTHER INFORMATION: recombinant peptide

<400> SEQUENCE: 123

Ala Leu Tyr Thr Met Met Lys Asp Gln Tyr Ala Cys Tyr Val Val Gln
1               5                   10                  15

Lys Met Ile Asp Val Ala Glu Pro Gly Gln Arg Lys Ile Val Met His
            20                  25                  30

Lys Ile Arg Pro
        35

<210> SEQ ID NO 124
<211> LENGTH: 36
<212> TYPE: PRT
<213> ORGANISM: Artificial Sequence
<220> FEATURE:
<223> OTHER INFORMATION: recombinant peptide

<400> SEQUENCE: 124

Ala Leu Tyr Thr Met Met Lys Asp Gln Tyr Ala Ser Tyr Val Val Glu
1               5                   10                  15

Lys Met Ile Asp Val Ala Glu Pro Gly Gln Arg Lys Ile Val Met His
```

-continued

```
                 20                  25                  30

Lys Ile Arg Pro
        35

<210> SEQ ID NO 125
<211> LENGTH: 36
<212> TYPE: PRT
<213> ORGANISM: Artificial Sequence
<220> FEATURE:
<223> OTHER INFORMATION: recombinant peptide

<400> SEQUENCE: 125

Ala Leu Tyr Thr Met Met Lys Asp Gln Tyr Ala Ser Tyr Val Val Arg
1               5                   10                  15

Lys Met Ile Asp Val Ala Glu Pro Gly Gln Arg Lys Ile Val Met His
            20                  25                  30

Lys Ile Arg Pro
        35

<210> SEQ ID NO 126
<211> LENGTH: 36
<212> TYPE: PRT
<213> ORGANISM: Artificial Sequence
<220> FEATURE:
<223> OTHER INFORMATION: recombinant peptide

<400> SEQUENCE: 126

Gln Val Phe Ala Leu Ser Thr His Pro Tyr Gly Cys Arg Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 127
<211> LENGTH: 36
<212> TYPE: PRT
<213> ORGANISM: Artificial Sequence
<220> FEATURE:
<223> OTHER INFORMATION: recombinant peptide

<400> SEQUENCE: 127

His Thr Glu Gln Leu Val Gln Asp Gln Tyr Gly Asn Tyr Val Ile Gln
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 128
<211> LENGTH: 36
<212> TYPE: PRT
<213> ORGANISM: Artificial Sequence
<220> FEATURE:
<223> OTHER INFORMATION: recombinant peptide

<400> SEQUENCE: 128

Gln Val Phe Ala Leu Ser Thr His Pro Tyr Gly Cys Arg Val Ile Gln
1               5                   10                  15

Arg Ile Leu Glu His Cys Leu Pro Asp Gln Thr Leu Pro Ile Leu Glu
            20                  25                  30

Glu Leu His Gln
```

<210> SEQ ID NO 129
<211> LENGTH: 36
<212> TYPE: PRT
<213> ORGANISM: Artificial Sequence
<220> FEATURE:
<223> OTHER INFORMATION: recombinant peptide

<400> SEQUENCE: 129

His Thr Glu Gln Leu Val Gln Asp Gln Tyr Gly Asn Arg Val Ile Gln
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 130
<211> LENGTH: 36
<212> TYPE: PRT
<213> ORGANISM: Artificial Sequence
<220> FEATURE:
<223> OTHER INFORMATION: recombinant peptide

<400> SEQUENCE: 130

Gln Val Phe Ala Leu Ser Thr His Pro Tyr Gly Cys Arg Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 131
<211> LENGTH: 36
<212> TYPE: PRT
<213> ORGANISM: Artificial Sequence
<220> FEATURE:
<223> OTHER INFORMATION: recombinant peptide

<400> SEQUENCE: 131

His Thr Glu Gln Leu Val Gln Asp Gln Tyr Gly Asn Tyr Val Ile Gln
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 132
<211> LENGTH: 36
<212> TYPE: PRT
<213> ORGANISM: Artificial Sequence
<220> FEATURE:
<223> OTHER INFORMATION: recombinant peptide

<400> SEQUENCE: 132

Gln Val Phe Ala Leu Ser Thr His Pro Tyr Gly Cys Tyr Val Ile Gln
1               5                   10                  15

Arg Ile Leu Glu His Cys Leu Pro Asp Gln Thr Leu Pro Ile Leu Glu
            20                  25                  30

Glu Leu His Gln
        35

```
<210> SEQ ID NO 133
<211> LENGTH: 36
<212> TYPE: PRT
<213> ORGANISM: Artificial Sequence
<220> FEATURE:
<223> OTHER INFORMATION: recombinant peptide

<400> SEQUENCE: 133

Gln Val Phe Ala Leu Ser Thr His Pro Tyr Gly Ser Arg Val Ile Glu
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 134
<211> LENGTH: 36
<212> TYPE: PRT
<213> ORGANISM: Artificial Sequence
<220> FEATURE:
<223> OTHER INFORMATION: recombinant peptide

<400> SEQUENCE: 134

His Thr Glu Gln Leu Val Gln Asp Gln Tyr Gly Ser Tyr Val Ile Arg
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 135
<211> LENGTH: 36
<212> TYPE: PRT
<213> ORGANISM: Artificial Sequence
<220> FEATURE:
<223> OTHER INFORMATION: recombinant peptide

<400> SEQUENCE: 135

Gln Val Phe Ala Leu Ser Thr His Pro Tyr Gly Ser Arg Val Ile Glu
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 136
<211> LENGTH: 36
<212> TYPE: PRT
<213> ORGANISM: Artificial Sequence
<220> FEATURE:
<223> OTHER INFORMATION: recombinant peptide

<400> SEQUENCE: 136

His Thr Glu Gln Leu Val Gln Asp Gln Tyr Gly Ser Arg Val Ile Arg
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 137
<211> LENGTH: 36
<212> TYPE: PRT
```

```
<213> ORGANISM: Artificial Sequence
<220> FEATURE:
<223> OTHER INFORMATION: recombinant peptide

<400> SEQUENCE: 137

Gln Val Phe Ala Leu Ser Thr His Pro Tyr Gly Ser Arg Val Ile Glu
 1               5                  10                  15

Arg Ile Leu Glu His Cys Leu Pro Asp Gln Thr Leu Pro Ile Leu Glu
            20                  25                  30

Glu Leu His Gln
        35

<210> SEQ ID NO 138
<211> LENGTH: 36
<212> TYPE: PRT
<213> ORGANISM: Artificial Sequence
<220> FEATURE:
<223> OTHER INFORMATION: recombinant peptide

<400> SEQUENCE: 138

His Thr Glu Gln Leu Val Gln Asp Gln Tyr Gly Ser Tyr Val Ile Arg
 1               5                  10                  15

His Val Leu Glu His Gly Arg Pro Glu Asp Lys Ser Lys Ile Val Ala
            20                  25                  30

Glu Ile Arg Gly
        35

<210> SEQ ID NO 139
<211> LENGTH: 36
<212> TYPE: PRT
<213> ORGANISM: Artificial Sequence
<220> FEATURE:
<223> OTHER INFORMATION: recombinant peptide

<400> SEQUENCE: 139

Gln Val Phe Ala Leu Ser Thr His Pro Tyr Gly Ser Tyr Val Ile Glu
 1               5                  10                  15

Arg Ile Leu Glu His Cys Leu Pro Asp Gln Thr Leu Pro Ile Leu Glu
            20                  25                  30

Glu Leu His Gln
        35

<210> SEQ ID NO 140
<211> LENGTH: 36
<212> TYPE: PRT
<213> ORGANISM: Artificial Sequence
<220> FEATURE:
<223> OTHER INFORMATION: recombinant peptide

<400> SEQUENCE: 140

Gln Val Phe Ala Leu Ser Thr His Pro Tyr Gly Ser Arg Val Ile Arg
 1               5                  10                  15

Arg Ile Leu Glu His Cys Leu Pro Asp Gln Thr Leu Pro Ile Leu Glu
            20                  25                  30

Glu Leu His Gln
        35

<210> SEQ ID NO 141
<211> LENGTH: 36
<212> TYPE: PRT
<213> ORGANISM: Artificial Sequence
<220> FEATURE:
<223> OTHER INFORMATION: recombinant peptide
```

<400> SEQUENCE: 141

His Thr Glu Gln Leu Val Gln Asp Gln Tyr Gly Asn Tyr Val Ile Gln
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 142
<211> LENGTH: 36
<212> TYPE: PRT
<213> ORGANISM: Artificial Sequence
<220> FEATURE:
<223> OTHER INFORMATION: recombinant peptide

<400> SEQUENCE: 142

Gln Val Phe Ala Leu Ser Thr His Pro Tyr Gly Ser Arg Val Ile Arg
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 143
<211> LENGTH: 36
<212> TYPE: PRT
<213> ORGANISM: Artificial Sequence
<220> FEATURE:
<223> OTHER INFORMATION: recombinant peptide

<400> SEQUENCE: 143

His Thr Glu Gln Leu Val Gln Asp Gln Tyr Gly Asn Arg Val Ile Gln
1               5                   10                  15

His Val Leu Glu His Gly Arg Pro Glu Asp Lys Ser Lys Ile Val Ala
            20                  25                  30

Glu Ile Arg Gly
        35

<210> SEQ ID NO 144
<211> LENGTH: 36
<212> TYPE: PRT
<213> ORGANISM: Artificial Sequence
<220> FEATURE:
<223> OTHER INFORMATION: recombinant peptide

<400> SEQUENCE: 144

Gln Val Phe Ala Leu Ser Thr His Pro Tyr Gly Ser Arg Val Ile Arg
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 145
<211> LENGTH: 36
<212> TYPE: PRT
<213> ORGANISM: Artificial Sequence
<220> FEATURE:
<223> OTHER INFORMATION: recombinant peptide

<400> SEQUENCE: 145

His Thr Glu Gln Leu Val Gln Asp Gln Tyr Gly Asn Tyr Val Ile Gln
1               5                   10                  15

His Val Leu Glu His Gly Arg Pro Glu Asp Lys Ser Lys Ile Val Ala
                20                  25                  30

Glu Ile Arg Gly
        35

<210> SEQ ID NO 146
<211> LENGTH: 36
<212> TYPE: PRT
<213> ORGANISM: Artificial Sequence
<220> FEATURE:
<223> OTHER INFORMATION: recombinant peptide

<400> SEQUENCE: 146

Gln Val Phe Ala Leu Ser Thr His Pro Tyr Gly Ser Tyr Val Ile Arg
1               5                   10                  15

Arg Ile Leu Glu His Cys Leu Pro Asp Gln Thr Leu Pro Ile Leu Glu
                20                  25                  30

Glu Leu His Gln
        35

<210> SEQ ID NO 147
<211> LENGTH: 36
<212> TYPE: PRT
<213> ORGANISM: Artificial Sequence
<220> FEATURE:
<223> OTHER INFORMATION: recombinant peptide

<400> SEQUENCE: 147

Gln Val Phe Ala Leu Ser Thr His Pro Tyr Gly Cys Phe Val Ile Gln
1               5                   10                  15

Arg Ile Leu Glu His Cys Leu Pro Asp Gln Thr Leu Pro Ile Leu Glu
                20                  25                  30

Glu Leu His Gln
        35

<210> SEQ ID NO 148
<211> LENGTH: 36
<212> TYPE: PRT
<213> ORGANISM: Artificial Sequence
<220> FEATURE:
<223> OTHER INFORMATION: recombinant peptide

<400> SEQUENCE: 148

Gln Val Phe Ala Leu Ser Thr His Pro Tyr Gly Cys His Val Ile Gln
1               5                   10                  15

Arg Ile Leu Glu His Cys Leu Pro Asp Gln Thr Leu Pro Ile Leu Glu
                20                  25                  30

Glu Leu His Gln
        35

<210> SEQ ID NO 149
<211> LENGTH: 36
<212> TYPE: PRT
<213> ORGANISM: Artificial Sequence
<220> FEATURE:
<223> OTHER INFORMATION: recombinant peptide

<400> SEQUENCE: 149

Gln Val Phe Ala Leu Ser Thr His Pro Tyr Gly Cys His Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 150
<211> LENGTH: 36
<212> TYPE: PRT
<213> ORGANISM: Artificial Sequence
<220> FEATURE:
<223> OTHER INFORMATION: recombinant peptide

<400> SEQUENCE: 150

Gln Val Phe Ala Leu Ser Thr His Pro Tyr Gly Cys Trp Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 151
<211> LENGTH: 36
<212> TYPE: PRT
<213> ORGANISM: Artificial Sequence
<220> FEATURE:
<223> OTHER INFORMATION: recombinant peptide

<400> SEQUENCE: 151

Gln Val Phe Ala Leu Ser Thr His Pro Tyr Gly Cys Tyr Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 152
<211> LENGTH: 36
<212> TYPE: PRT
<213> ORGANISM: Artificial Sequence
<220> FEATURE:
<223> OTHER INFORMATION: recombinant peptide

<400> SEQUENCE: 152

Gln Val Phe Ala Leu Ser Thr His Pro Tyr Gly Ser Arg Val Ile Glu
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 153
<211> LENGTH: 36
<212> TYPE: PRT
<213> ORGANISM: Artificial Sequence
<220> FEATURE:
<223> OTHER INFORMATION: recombinant peptide

<400> SEQUENCE: 153

Gln Val Phe Ala Leu Ser Thr His Pro Tyr Gly Ser Lys Val Ile Glu
1               5                   10                  15

Arg Ile Leu Glu His Cys Leu Pro Asp Gln Thr Leu Pro Ile Leu Glu
            20                  25                  30

-continued

Glu Leu His Gln
        35

<210> SEQ ID NO 154
<211> LENGTH: 36
<212> TYPE: PRT
<213> ORGANISM: Artificial Sequence
<220> FEATURE:
<223> OTHER INFORMATION: recombinant peptide

<400> SEQUENCE: 154

Gln Val Phe Ala Leu Ser Thr His Pro Tyr Gly Ser Phe Val Ile Glu
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 155
<211> LENGTH: 36
<212> TYPE: PRT
<213> ORGANISM: Artificial Sequence
<220> FEATURE:
<223> OTHER INFORMATION: recombinant peptide

<400> SEQUENCE: 155

Gln Val Phe Ala Leu Ser Thr His Pro Tyr Gly Ser His Val Ile Glu
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 156
<211> LENGTH: 36
<212> TYPE: PRT
<213> ORGANISM: Artificial Sequence
<220> FEATURE:
<223> OTHER INFORMATION: recombinant peptide

<400> SEQUENCE: 156

Gln Val Phe Ala Leu Ser Thr His Pro Tyr Gly Ser Trp Val Ile Glu
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 157
<211> LENGTH: 36
<212> TYPE: PRT
<213> ORGANISM: Artificial Sequence
<220> FEATURE:
<223> OTHER INFORMATION: recombinant peptide

<400> SEQUENCE: 157

Gln Val Phe Ala Leu Ser Thr His Pro Tyr Gly Ser Tyr Val Ile Glu
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 158
<211> LENGTH: 36
<212> TYPE: PRT
<213> ORGANISM: Artificial Sequence
<220> FEATURE:
<223> OTHER INFORMATION: recombinant peptide

<400> SEQUENCE: 158

Gln Val Phe Ala Leu Ser Thr His Pro Tyr Gly Asn Arg Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 159
<211> LENGTH: 36
<212> TYPE: PRT
<213> ORGANISM: Artificial Sequence
<220> FEATURE:
<223> OTHER INFORMATION: recombinant peptide

<400> SEQUENCE: 159

Gln Val Phe Ala Leu Ser Thr His Pro Tyr Gly Asn Lys Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 160
<211> LENGTH: 36
<212> TYPE: PRT
<213> ORGANISM: Artificial Sequence
<220> FEATURE:
<223> OTHER INFORMATION: recombinant peptide

<400> SEQUENCE: 160

Gln Val Phe Ala Leu Ser Thr His Pro Tyr Gly Asn Phe Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 161
<211> LENGTH: 36
<212> TYPE: PRT
<213> ORGANISM: Artificial Sequence
<220> FEATURE:
<223> OTHER INFORMATION: recombinant peptide

<400> SEQUENCE: 161

Gln Val Phe Ala Leu Ser Thr His Pro Tyr Gly Asn His Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 162
<211> LENGTH: 36

```
<212> TYPE: PRT
<213> ORGANISM: Artificial Sequence
<220> FEATURE:
<223> OTHER INFORMATION: recombinant peptide

<400> SEQUENCE: 162

Gln Val Phe Ala Leu Ser Thr His Pro Tyr Gly Asn Trp Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 163
<211> LENGTH: 36
<212> TYPE: PRT
<213> ORGANISM: Artificial Sequence
<220> FEATURE:
<223> OTHER INFORMATION: recombinant peptide

<400> SEQUENCE: 163

Gln Val Phe Ala Leu Ser Thr His Pro Tyr Gly Asn Tyr Val Ile Gln
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 164
<211> LENGTH: 36
<212> TYPE: PRT
<213> ORGANISM: Artificial Sequence
<220> FEATURE:
<223> OTHER INFORMATION: recombinant peptide

<400> SEQUENCE: 164

Gln Val Phe Ala Leu Ser Thr His Pro Tyr Gly Ser Arg Val Ile Arg
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 165
<211> LENGTH: 36
<212> TYPE: PRT
<213> ORGANISM: Artificial Sequence
<220> FEATURE:
<223> OTHER INFORMATION: recombinant peptide

<400> SEQUENCE: 165

Gln Val Phe Ala Leu Ser Thr His Pro Tyr Gly Ser Lys Val Ile Arg
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 166
<211> LENGTH: 36
<212> TYPE: PRT
<213> ORGANISM: Artificial Sequence
<220> FEATURE:
```

<223> OTHER INFORMATION: recombinant peptide

<400> SEQUENCE: 166

Gln Val Phe Ala Leu Ser Thr His Pro Tyr Gly Ser Phe Val Ile Arg
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 167
<211> LENGTH: 36
<212> TYPE: PRT
<213> ORGANISM: Artificial Sequence
<220> FEATURE:
<223> OTHER INFORMATION: recombinant peptide

<400> SEQUENCE: 167

Gln Val Phe Ala Leu Ser Thr His Pro Tyr Gly Ser His Val Ile Arg
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 168
<211> LENGTH: 36
<212> TYPE: PRT
<213> ORGANISM: Artificial Sequence
<220> FEATURE:
<223> OTHER INFORMATION: recombinant peptide

<400> SEQUENCE: 168

Gln Val Phe Ala Leu Ser Thr His Pro Tyr Gly Ser Trp Val Ile Arg
1               5                   10                  15

Arg Ile Leu Glu His Cys Leu Pro Asp Gln Thr Leu Pro Ile Leu Glu
            20                  25                  30

Glu Leu His Gln
        35

<210> SEQ ID NO 169
<211> LENGTH: 36
<212> TYPE: PRT
<213> ORGANISM: Artificial Sequence
<220> FEATURE:
<223> OTHER INFORMATION: recombinant peptide

<400> SEQUENCE: 169

Gln Val Phe Ala Leu Ser Thr His Pro Tyr Gly Ser Tyr Val Ile Arg
1               5                   10                  15

Arg Ile Leu Glu His Cys Leu Pro Asp Gln Thr Leu Pro Ile Leu Glu
            20                  25                  30

Glu Leu His Gln
        35

RNA-BINDING PROTEIN

CROSS-REFERENCE TO RELAYED APPLICATION

This application is a Section 371 of International Application No. PCT/EP2018/010489, filed Mar. 16, 2018, which was published in the Japanese language on Sep. 20, 2018 under International Publication No. WO 2018/169058 A1, and claims priority under 35 U.S.C. § 119(b) to Japanese Application No. 2017-053093, filed Mar. 17, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Updated Sequence Listing 688461-23US", creation date of Nov. 18, 2021, and having a size of 64,094 bytes. The sequence listing submitted via EFS-Web is part of the specification and is herein incorporated by reference in its entirety.

TECHNICAL FIELD

The present invention relates to an RNA-binding protein.

BACKGROUND ART

A human Pumilio and FBF homology (hPUF) protein is known as an RNA-binding protein having high binding ability and selectivity (see, for example, Non-Patent Document 1). It is known that the hPUF protein has eight repeat motifs that are different in amino acid sequence and length, and three amino acid residues in a single repeat recognize one base. The eight repeat motifs are herein referred to as R1, R2, R3, R4, R5, R6, R7, and R8 from the N-terminal side. The amino acid sequences of the respective repeat motifs are as follows. FIG. 163 shows the regularity of wild-type stacking amino acids by the molecular model.

R1:
(SEQ ID NO: 1)
HIMEFSQDQHGSRFIQLKLERATPAERQLVFNEILQ

R2:
(SEQ ID NO: 2)
AAYQLMVDVFGNYVIQKFFEFGSLEQKLALAERIRG

R3:
(SEQ ID NO: 3)
HVLSLALQMYGCRVIQKALEFIPSDQQNEMVRELDG

R4:
(SEQ ID NO: 4)
HVLKCVKDQNGNHVVQKCIECVQPQSLQFIIDAFKG

R5:
(SEQ ID NO: 5)
QVFALSTHPYGCRVIQRILEHCLPDQTLPILEELHQ

R6:
(SEQ ID NO: 6)
HTEQLVQDQYGNYVIQHVLEHGRPEDKSKIVAEIRG

R7:
(SEQ ID NO: 7)
NVLVLSQHKFASNVVEKCVTHASRTERAVLIDEVCTMNDGPHS

R8:
(SEQ ID NO: 8)
ALYTMMKDQYANYVVQKMIDVAEPGQRKIVMHKIRP

PRIOR ART DOCUMENTS

Non-Patent Documents

Non-Patent Document 1: X. Wang, et. al. Cell, Vol. 110, 501-512, Aug. 23, 2002

SUMMARY OF INVENTION

Object to be Solved by the Invention

An object of the present invention is to provide a soluble RNA-binding protein having high binding ability.

Means for Solving the Object

As a result of intensive studies in order to achieve the above objects, the present inventors found that a soluble RNA-binding protein having high binding ability can be designed in accordance with a target RNA sequence by modifying the configuration of eight repeat motifs R1 to R8 or amino acid residues of the motifs. This has led to the completion of the present invention. According to the present invention, the following inventions are provided.

<1> An RNA-binding protein having an amino acid sequence represented by R1'—R1X—R2X—(R5X or R6Y)L-(R5X—R6Y)$_M$—(R5X or R6Y)$_N$—R7X—R8X—R8':
wherein
R1X represents R1, R1(S12N), R1(S12C), R1(Q16E), or R1(Q16R),
R2X represents R2, R2(N12C), R2(N12S), R2(N12S, Q16E), or R2(N12S, Q16R),
R5X represents any one of R5, R5(C12S), R5(C12N), R5(C12S, Q16E), or R5(C12S, Q16R),
R6Y represents any one of R6, R6(N12C), R6(N12S), R6(N12S, Q16E), or R6(N12S, Q16R),
R7X represents R7, R7(S12C, E16Q), R7(E16Q), R7(S12N, E16Q), or R7(E16R),
R8X represents R8, R8(N12C), R8(N12S), R8(N12S, Q16E), or R8(N12S, Q16R).
S12N represents a substitution of a 12th amino acid S with N,
S12C represents a substitution of a 12th amino acid S with C,
N12C represents a substitution of a 12th amino acid N with C,
N12S represents a substitution of a 12th amino acid N with S,
C12N represents a substitution of a 12th amino acid C with N,
C12S represents a substitution of a 12th amino acid C with S,
Q16E represents a substitution of a 16th amino acid Q with E,
Q16R represents a substitution of a 16th amino acid Q with R,
L and N each independently represent 0 or 1, and M represents an integer of 2 or more, M preferably represents an integer of 2 to 20, more preferably an integer of 2 to 10, and even more preferably an integer of 2 to 5, and each repeat corresponds to the following relevant amino acid sequence:

```
R1':
                                          (SEQ ID NO: 9)
GRSRLLEDFRNNRYPNLQLREIAG;

R1:
                                          (SEQ ID NO: 1)
HIMEFSQDQHGSRFIQLKLERATPAERQLVFNEILQ;

R2:
                                          (SEQ ID NO: 2)
AAYQLMVDVFGNYVIQKFFEFGSLEQKLALAERIRG;

R5:
                                          (SEQ ID NO: 5)
QVFALSTHPYGCRVIQRILEHCLPDQTLPILEELHQ;

R6:
                                          (SEQ ID NO: 6)
HTEQLVQDQYGNYVIQHVLEHGRPEDKSKIVAEIRG;

R7:
                                          (SEQ ID NO: 7)
NVLVLSQHKFASNVVEKCVTHASRTERAVLIDEVCTMNDGPHS;

R8:
                                          (SEQ ID NO: 8)
ALYTMMKDQYANYVVQKMIDVAEPGQRKIVMHKIRP;

R8':
                                          (SEQ ID NO: 10)
HIATLRKYTYGKHILAKLEKYYMKNGVDLG.
```

<2> The protein according to <1>, wherein for at least one of the repeats R1X, R2X, R5X, R6Y, R7X, and R8X,
in a case in which a combination of a base recognized by the repeat and a downstream base adjacent thereto is A-A, the 13th amino acid of the corresponding repeat (i.e., an amino acid stacking between the two bases) is Tyr or His,
in a case in which the combination is G-A, U-A, C-A, U—C, or C—U, the 13th amino acid of the corresponding repeat (i.e., an amino acid stacking between the two bases) is Tyr,
in a case in which the combination is A-G, A-C, G-U, U-G, C-G, or G-C, the 13th amino acid of the corresponding repeat (i.e., an amino acid stacking between the two bases) is Arg,
in a case in which the combination is A-U or G-G, the 13th amino acid of the corresponding repeat (i.e., an amino acid stacking between the two bases) is Arg or His, in a case in which the combination is U—U, the 13th amino acid of the corresponding repeat (i.e., an amino acid stacking between the two bases) is Trp or Arg, and/or
in a case in which the combination is C—C, the 13th amino acid of the corresponding repeat (i.e., an amino acid stacking between the two bases) is Phe.

<3> An RNA-binding protein having an amino acid sequence represented by EIRG-(R5X—R6Y)n: wherein n R5Xs each independently represent R5, R5(C12N), R5(C12S, Q16E), or R5(C12S, Q16E), n R6Ys each independently represent R6, R6(N12C), R6(N12S, Q16E), or R6(N12S, Q16R), and n represents an integer of 4 to 15:

```
    R5:
                                          (SEQ ID NO: 5)
QVFALSTHPYGCRVIQRILEHCLPDQTLPILEELHQ;

R5(C12N):
                                          (SEQ ID NO: 11)
QVFALSTHPYGNRVIQRILEHCLPDQTLPILEELHQ;

R5(C12S, Q16E):
                                          (SEQ ID NO: 12)
QVFALSTHPYGSRVIERILEHCLPDQTLPILEELHQ;

R5(C12S, Q16R):
                                          (SEQ ID NO: 13)
QVFALSTHPYGSRVIRRILEHCLPDQTLPILEELHQ;

R6:
                                          (SEQ ID NO: 6)
HTEQLVQDQYGNYVIQHVLEHGRPEDKSKIVAEIRG;

R6(N12C):
                                          (SEQ ID NO: 14)
HTEQLVQDQYGCYVIQHVLEHGRPEDKSKIVAEIRG;

R6(N12S, Q16E):
                                          (SEQ ID NO: 15)
HTEQLVQDQYGSYVIEHVLEHGRPEDKSKIVAEIRG;

R6(N12S, Q16R):
                                          (SEQ ID NO: 16)
HTEQLVQDQYGSYVIRHVLEHGRPEDKSKIVAEIRG.
```

<4> An RNA-binding protein having an amino acid sequence represented by AFKG-(R5X—R6YZ)$_{n-1}$ R5X—R6Y, wherein n R5Xs each independently represent R5, R5(C12N), R5(C12S, Q16E), or R5(C12S, Q16E), (n−1) R6YZs each independently represent R6 (AFKG), R6(N12C) (AFKG), R6(N12S, Q16E) (AFKG), or R6(N12S, Q16R) (AFKG), R6Y represents R6, R6(N12C), R6(N12S, Q16E), or R6(N12S, Q16R), and n represents an integer of 4 to 15:

```
    R5:
                                          (SEQ ID NO: 5)
QVFALSTHPYGCRVIQRILEHCLPDQTLPILEELHQ;

R5(C12N):
                                          (SEQ ID NO: 11)
QVFALSTHPYGNRVIQRILEHCLPDQTLPILEELHQ;

R5(C12S, Q16E):
                                          (SEQ ID NO: 12)
QVFALSTHPYGSRVIERILEHCLPDQTLPILEELHQ;

R5(C12S, Q16R):
                                          (SEQ ID NO: 13)
QVFALSTHPYGSRVIRRILEHCLPDQTLPILEELHQ;

R6 (AFKG):
                                          (SEQ ID NO: 17)
HTEQLVQDQYGNYVIQHVLEHGRPEDKSKIVAAFKG;

R6(N12C) (AFKG):
                                          (SEQ ID NO: 18)
HTEQLVQDQYGCYVIQHVLEHGRPEDKSKIVAAFKG;

R6(N12S, Q16E) (AFKG):
                                          (SEQ ID NO: 19)
HTEQLVQDQYGSYVIEHVLEHGRPEDKSKIVAAFKG;

R6(N12S, Q16R) (AFKG):
                                          (SEQ ID NO: 20)
HTEQLVQDQYGSYVIEHVLEHGRPEDKSKIVAAFKG;

R6:
                                          (SEQ ID NO: 6)
HTEQLVQDQYGNYVIQHVLEHGRPEDKSKIVAEIRG;

R6(N12C):
                                          (SEQ ID NO: 14)
HTEQLVQDQYGCYVIQHVLEHGRPEDKSKIVAEIRG;
```

```
R6(N12S, Q16E):
                                        (SEQ ID NO: 15)
HTEQLVQDQYGSYVIEHVLEHGRPEDKSKIVAEIRG;

R6(N12S, Q16R):
                                        (SEQ ID NO: 16)
HTEQLVQDQYGSYVIRHVLEHGRPEDKSKIVAEIRG.
```

<5> The protein according to <3> or <4>, which further has R1' at the N terminus and/or R8' at the C terminus:

```
R1':
                                         (SEQ ID NO: 9)
GRSRLLEDFRNNRYPNLQLREIAG;

R8':
                                        (SEQ ID NO: 10)
HIATLRKYTYGKHILAKLEKYYMKNGVDLG.
```

<6> The protein according to <3> or <4>, which further has R1'-R1-R2 at the N terminus and/or R8-R8' at the C terminus.

```
R1':
                                         (SEQ ID NO: 9)
GRSRLLEDFRNNRYPNLQLREIAG;

R8':
                                        (SEQ ID NO: 10)
HIATLRKYTYGKHILAKLEKYYMKNGVDLG.

R1:
                                         (SEQ ID NO: 1)
HIMEFSQDQHGSRFIQLKLERATPAERQLVFNEILQ;

R2:
                                         (SEQ ID NO: 2)
AAYQLMVDVFGNYVIQKFFEFGSLEQKLALAERIRG;

R8:
                                         (SEQ ID NO: 8)
ALYTMMKDQYANYVVQKMIDVAEPGQRKIVMHKIRP.
```

<A> An RNA-binding protein having an amino acid sequence represented by
R1'-R1-R2-R5X—R4-R5X—R6Y—R7-R8-R8',
R1'-R1-R2-R3-R6Y—R5X—R6Y—R7-R8-R8',
R1'-R1-R2-R5X—R5X—R5X—R6Y—R7-R8-R8',
R1'-R1-R2-R5X—R5(R13H)—R5X—R6Y—R7-R8-R8',
R1'-R1-R2-R5X—R6Y—R5X—R6Y—R7-R8-R8',
R1'-R1-R2-R5X—R6Y—R5X—R6Y—R5X—R6Y—R7-R8-R8',
R1'-R1-R2-R3-R4-R5X—R6Y—R7(ILQ)-R8-R8',
R1'-R1-R2-R3-R4-R5X—R6Y—R7(IRG)-R8-R8',
R1'-R1-R2-R5X—R6Y—R5X—R6Y—R5X—R6Y—R5X—R6Y—R7-R8-R8',
R1'-R1-R2-R5X—R6Y—R5X—R6Y—R5X—R6Y—R5X—R6Y—R5X—R6Y—R7-R8-R8',
R1'-R1-R2-R5X—R6Y—R5X—R6Y—R5X—R6Y—R5X—R6Y—R5X—R6Y—R5X—R6Y—R7-R8-R8',
R1'-R1-R2-R5X—R5X—R5X—R6-R7-R8-R8',
R1'-R1-R2-R3-R6Y—R5X—R6Y—R7-R8-R8',
R1'-R1-R2-R3-R4-R5 (R13K)—R6Y—R7-R8-R8',
R1'-R1-R2-R3-R4-R5X—R6(Y13W)—R7-R8-R8',
R1'-R1-R2-R5X—R5(R13H)—R5(R13H)—R6Y—R7-R8-R8',
R1'-R1-R2-R5X—R5(R13F)—R5(R13F)—R6Y—R7-R8-R8',
R1'-R1-R2-R5X—R5(R13Y)—R5(R13Y)—R6Y—R7-R8-R8',
R1'-R1-R2-R5X—R5(R13W)—R5(R13W)—R6Y—R7-R8-R8',
R1'-R1-R2-R6Y—R5X—R6Y—R5X—R6Y—R7-R8-R8',
R1'-R1-R2-R5X—R5X—R6Y—R5X—R6Y—R7-R8-R8',
R1'-R1-R2-R5X—R6Y—R5X—R6Y—R6Y—R7-R8-R8',
R1'-R1-R2-R5X—R5X—R6Y—R5X—R6Y—R5X—R6Y—R7-R8-R8',
R1'-R1-R2-R5X—R5X—R6Y—R5X—R6Y—R5X—R6Y—R5X—R6Y—R7-R8-R8', or
R1'-R1-R2-R5X—R5X—R6Y—R5X—R6Y—R5X—R6Y—R5X—R6Y—R5X—R6Y—R7-R8-R8'
(wherein R5X represents R5, R5(C12N), R5(C12S, Q16E), or R5(C12S, Q16R), R6Y represents R6, R6(N12C), R6(N12S, Q16E) or R6(N12S, Q16R), and each repeat corresponds to the following relevant amino acid sequence):

R1':
(SEQ ID NO: 9)
GRSRLLEDFRNNRYPNLQLREIAG;

R1:
(SEQ ID NO: 1)
HIMEFSQDQHGSRFIQLKLERATPAERQLVFNEILQ;

R2:
(SEQ ID NO: 2)
AAYQLMVDVFGNYVIQKFFEFGSLEQKLALAERIRG;

R3:
(SEQ ID NO: 3)
HVLSLALQMYGCRVIQKALEFIPSDQQNEMVRELDG;

R4:
(SEQ ID NO: 4)
HVLKCVKDQNGNHVVQKCIECVQPQSLQFIIDAFKG;

R5:
(SEQ ID NO: 5)
QVFALSTHPYGCRVIQRILEHCLPDQTLPILEELHQ;

R5(R13H):
(SEQ ID NO: 21)
QVFALSTHPYGCHVIQRILEHCLPDQTLPILEELHQ;

R5(C12N):
(SEQ ID NO: 22)
QVFALSTHPYGNRVIQRILEHCLPDQTLPILEELHQ;

R5(R13K):
(SEQ ID NO: 23)
QVFALSTHPYGCKVIQRILEHCLPDQTLPILEELHQ;

R5(R13F):
(SEQ ID NO: 24)
QVFALSTHPYGCFVIQRILEHCLPDQTLPILEELHQ;

R5(R13Y):
(SEQ ID NO: 25)
QVFALSTHPYGCYVIQRILEHCLPDQTLPILEELHQ;

R5(R13W):
(SEQ ID NO: 26)
QVFALSTHPYGCWVIQRILEHCLPDQTLPILEELHQ;

R5(C12S, Q16E):
(SEQ ID NO: 12)
QVFALSTHPYGSRVIERILEHCLPDQTLPILEELHQ;

R5(C12S, Q16R):
(SEQ ID NO: 13)
QVFALSTHPYGSRVIRRILEHCLPDQTLPILEELHQ;

R6:
(SEQ ID NO: 6)
HTEQLVQDQYGNYVIQHVLEHGRPEDKSKIVAEIRG;

R6(N12C):
(SEQ ID NO: 14)
HTEQLVQDQYGCYVIQHVLEHGRPEDKSKIVAEIRG;

R6(N12S, Q16E):
(SEQ ID NO: 15)
HTEQLVQDQYGSYVIEHVLEHGRPEDKSKIVAEIRG;

R6(N12S, Q16R):
(SEQ ID NO: 16)
HTEQLVQDQYGSYVIRHVLEHGRPEDKSKIVAEIRG;

R6(Y13W):
(SEQ ID NO: 27)
HTEQLVQDQYGNWVIQHVLEHGRPEDKSKIVAEIRG;

R7:
(SEQ ID NO: 7)
NVLVLSQHKFASNVVEKCVTHASRTERAVLIDEVCTMNDGPHS;

R7(ILQ):
(SEQ ID NO: 28)
NVLVLSQHKFASNVVEKCVTHASRTERAVLIDEILQ;

R7(IRG):
(SEQ ID NO: 29)
NVLVLSQHKFASNVVEKCVTHASRTERAVLIDEIRG;

R8:
(SEQ ID NO: 8)
ALYTMMKDQYANYVVQKMIDVAEPGQRKIVMHKIRP;

R8':
(SEQ ID NO: 10)
HIATLRKYTYGKHILAKLEKYYMKNGVDLG.

<B> An RNA-binding protein having an amino acid sequence represented by R1'-(Rx)$_n$-R8' (wherein n represents an integer of 8 to 30, Rx independently represents any repeat of R1, R2, R3, R4, R5X, R6X, R7 or R8, the definitions of R1', R1, R2, R3, R4, R5X, R6X, R7, R8, and R8', are as described in <A>), wherein for at least one of the repeats, in a case in which a combination of a base recognized by the repeat and a downstream base adjacent thereto is A-A, the 13th amino acid of at least one of the repeats is Tyr or His, in a case in which the combination is G-A, U-A, C-A, U—C, or C—U, the 13th amino acid of at least one of the repeats is Tyr, in a case in which the combination is A-G, A-C, G-U, U-G, C-G, or G-C, the 13th amino acid of at least one of the repeats is Arg, in a case in which the combination is A-U or G-G, the 13th amino acid of at least one of the repeats is Arg or His, in a case in which the combination is U—U, the 13th amino acid of at least one of the repeats is Trp or Arg, and/or in a case in which the combination is C—C, the 13th amino acid of at least one of the repeats is Phe.

<C> An RNA-binding protein having an amino acid sequence represented by R1'-R1-R2-R5-R6-R5-R6-R5-R6-R7-R8-R8' (wherein R1' represents GRSRLLEDFRNNRYPNLQLREIAG (SEQ ID NO:9), R8' represents HIATLRKYTYGKHILAKLEKYYMKNGVDLG (SEQ ID NO:10), and R1, R2, R5 to R8, R1', and R8' each represent any of the following (1) to (9)):

(1)
R1:
(SEQ ID NO: 1)
HIMEFSQDQHGSRFIQLKLERATPAERQLVFNEILQ

R2:
(SEQ ID NO: 2)
AAYQLMVDVFGNYVIQKFFEFGSLEQKLALAERIRG

R5:
(SEQ ID NO: 5)
QVFALSTHPYGCRVIQRILEHCLPDQTLPILEELHQ

R6:
(SEQ ID NO: 6)
HTEQLVQDQYGSYVIRHVLEHGRPEDKSKIVAEIRG

R5:
(SEQ ID NO: 5)
QVFALSTHPYGCRVIQRILEHCLPDQTLPILEELHQ

R6:
(SEQ ID NO: 6)
HTEQLVQDQYGSYVIRHVLEHGRPEDKSKIVAEIRG

R5:
(SEQ ID NO: 5)
QVFALSTHPYGCRVIQRILEHCLPDQTLPILEELHQ

R6:
(SEQ ID NO: 6)
HTEQLVQDQYGSYVIRHVLEHGRPEDKSKIVAEIRG

R7:
(SEQ ID NO: 7)
NVLVLSQHKFASNVVEKCVTHASRTERAVLIDEVCTMNDGPHS

R8:
(SEQ ID NO: 8)
ALYTMMKDQYANYVVQKMIDVAEPGQRKIVMHKIRP (2)
R1:
(SEQ ID NO: 1)
HIMEFSQDQHGSRFIQLKLERATPAERQLVFNEILQ

R2:
(SEQ ID NO: 2)
AAYQLMVDVFGNYVIQKFFEFGSLEQKLALAERIRG

R5:
(SEQ ID NO: 5)
QVFALSTHPYGCRVIQRILEHCLPDQTLPILEELHQ

R6:
(SEQ ID NO: 6)
HTEQLVQDQYGSVIRHVLEHGRPEDKSKIVAEIRG

R5:
(SEQ ID NO: 5)
QVFALSTHPYGCRVIQRILEHCLPDQTLPILEELHQ

R6:
(SEQ ID NO: 6)
HTEQLVQDQYGSVIRHVLEHGRPEDKSKIVAEIRG

R5:
(SEQ ID NO: 5)
QVFALSTHPYGCRVIQRILEHCLPDQTLPILEELHQ

R6:
(SEQ ID NO: 6)
HTEQLVQDQYGSVIRHVLEHGRPEDKSKIVAEIRG

R7:
(SEQ ID NO: 7)
NVLVLSQHKFASNVVEKCVTHASRTERAVLIDEVCTMNDGPHS

R8:
(SEQ ID NO: 8)
ALYTMMKDQYANYVVQKMIDVAEPGQRKIVMHKIRP (3)
R1:
(SEQ ID NO: 1)
HIMEFSQDQHGSRFIQLKLERATPAERQLVFNEILQ

R2:
(SEQ ID NO: 2)
AAYQLMVDVFGNYVIQKFFEFGSLEQKLALAERIRG

R5:
(SEQ ID NO: 5)
QVFALSTHPYGCRVIQRILEHCLPDQTLPILEELHQ

R6:
(SEQ ID NO: 6)
HTEQLVQDQYGSYVIRHVLEHGRPEDKSIVAEIRG

R5:
(SEQ ID NO: 5)
QVFALSTHPYGCYVIQRILEHCLPDQTLPILEELHQ

R6:
(SEQ ID NO: 6)
HTEQLVQDQYGSYVIRHVLEHGRPEDKSIVAEIRG

R5:
(SEQ ID NO: 5)
QVFALSTHPYGCYVIQRILEHCLPDQTLPILEELHQ

R6:
(SEQ ID NO: 6)
HTEQLVQDQYGSYVIRHVLEHGRPEDKSIVAEIRG

R7:
(SEQ ID NO: 7)
NVLVLSQHKFASNVVEKCVTHASRTERAVLIDEVCTMNDGPHS

R8:
(SEQ ID NO: 8)
ALYTMMKDQYANYVVQKMIDVAEPGQRKIVMHKIRP (4)
R1:
(SEQ ID NO: 1)
HIMEFSQDQHGSRFIQLKLERATPAERQLVFNEILQ

R2:
(SEQ ID NO: 2)
AAYQLMVDVFGNYVIQKFFEFGSLEQKLALAERIRG

R5:
(SEQ ID NO: 5)
QVFALSTHPYGCRVIQRILEHCLPDQTLPILEELHQ

R6:
(SEQ ID NO: 6)
HTEQLVQDQYGSYVIEHVLEHGRPEDKSIVAEIRG

R5:
(SEQ ID NO: 5)
QVFALSTHPYGCRVIQRILEHCLPDQTLPILEELHQ

R6:
(SEQ ID NO: 6)
HTEQLVQDQYGSYVIEHVLEHGRPEDKSIVAEIRG

R5:
(SEQ ID NO: 5)
QVFALSTHPYGCRVIQRILEHCLPDQTLPILEELHQ

R6:
(SEQ ID NO: 6)
HTEQLVQDQYGSYVIEHVLEHGRPEDKSIVAEIRG

R7:
(SEQ ID NO: 7)
NVLVLSQHKFASNVVEKCVTHASRTERAVLIDEVCTMNDGPHS

R8:
(SEQ ID NO: 8)
ALYTMMKDQYANYVVQKMIDVAEPGQRKIVMHKIRP (5)
R1:
(SEQ ID NO: 1)
HIMEFSQDQHGSRFIQLKLERATPAERQLVFNEILQ

R2:
(SEQ ID NO: 2)
AAYQLMVDVFGNYVIQKFFEFGSLEQKLALAERIRG

R5:
(SEQ ID NO: 5)
QVFALSTHPYGCRVIQRILEHCLPDQTLPILEELHQ

R6:
(SEQ ID NO: 6)
HTEQLVQDQYGSRVIEHVLEHGRPEDKSIVAEIRG

R5:
(SEQ ID NO: 5)
QVFALSTHPYGCRVIQRILEHCLPDQTLPILEELHQ

R6:
(SEQ ID NO: 6)
HTEQLVQDQYGSRVIEHVLEHGRPEDKSIVAEIRG

R5:
(SEQ ID NO: 5)
QVFALSTHPYGCRVIQRILEHCLPDQTLPILEELHQ

R6:
(SEQ ID NO: 6)
HTEQLVQDQYGSRVIEHVLEHGRPEDKSIVAEIRG

R7:
(SEQ ID NO: 7)
NVLVLSQHKFASNVVEKCVTHASRTERAVLIDEVCTMNDGPHS

R8:
(SEQ ID NO: 8)
ALYTMMKDQYANYVVQKMIDVAEPGQRKIVMHKIRP (6)
R1:
(SEQ ID NO: 1)
HIMEFSQDQHGSRFIQLKLERATPAERQLVFNEILQ

R2:
(SEQ ID NO: 2)
AAYQLMVDVFGNYVIQKFFEFGSLEQKLALAERIRG

R5:
(SEQ ID NO: 5)
QVFALSTHPYGCRVIQRILEHCLPDQTLPILEELHQ

R6:
(SEQ ID NO: 6)
HTEQLVQDQYGSYVIEHVLEHGRPEDKSIVAEIRG

R5:
(SEQ ID NO: 5)
QVFALSTHPYGCYVIQRILEHCLPDQTLPILEELHQ

R6:
(SEQ ID NO: 6)
HTEQLVQDQYGSYVIEHVLEHGRPEDKSIVAEIRG

R5:
(SEQ ID NO: 5)
QVFALSTHPYGCYVIQRILEHCLPDQTLPILEELHQ

R6:
(SEQ ID NO: 6)
HTEQLVQDQYGSYVIEHVLEHGRPEDKSIVAEIRG

R7:
(SEQ ID NO: 7)
NVLVLSQHKFASNVVEKCVTHASRTERAVLIDEVCTMNDGPHS

R8:
(SEQ ID NO: 8)
ALYTMMKDQYANYVVQKMIDVAEPGQRKIVMHKIRP (7)
R1:
(SEQ ID NO: 1)
HIMEFSQDQHGSRFIQLKLERATPAERQLVFNEILQ

R2:
(SEQ ID NO: 2)
AAYQLMVDVFGNYVIQKFFEFGSLEQKLALAERIRG

R5:
(SEQ ID NO: 5)
QVFALSTHPYGSRVIERILEHCLPDQTLPILEELHQ

R6:
(SEQ ID NO: 6)
HTEQLVQDQYGNYVIQHVLEHGRPEDKSIVAEIRG

R5:
(SEQ ID NO: 5)
QVFALSTHPYGSRVIERILEHCLPDQTLPILEELHQ

R6:
(SEQ ID NO: 6)
HTEQLVQDQYGNYVIQHVLEHGRPEDKSIVAEIRG

R5:
(SEQ ID NO: 5)
QVFALSTHPYGSRVIERILEHCLPDQTLPILEELHQ

R6:
(SEQ ID NO: 6)
HTEQLVQDQYGNYVIQHVLEHGRPEDKSIVAEIRG

R7:
(SEQ ID NO: 7)
NVLVLSQHKFASNVVEKCVTHASRTERAVLIDEVCTMNDGPHS

R8:
(SEQ ID NO: 8)
ALYTMMKDQYANYVVQKMIDVAEPGQRKIVMHKIRP (8)
R1:
(SEQ ID NO: 1)
HIMEFSQDQHGSRFIQLKLERATPAERQLVFNEILQ

R2:
(SEQ ID NO: 2)
AAYQLMVDVFGNYVIQKFFEFGSLEQKLALAERIRG

R5:
(SEQ ID NO: 5)
QVFALSTHPYGSRVIERILEHCLPDQTLPILEELHQ

R6:
(SEQ ID NO: 6)
HTEQLVQDQYGNRVIQHVLEHGRPEDKSIVAEIRG

R5:
(SEQ ID NO: 5)
QVFALSTHPYGSRVIERILEHCLPDQTLPILEELHQ

R6:
(SEQ ID NO: 6)
HTEQLVQDQYGNRVIQHVLEHGRPEDKSIVAEIRG

R5:
(SEQ ID NO: 5)
QVFALSTHPYGSRVIERILEHCLPDQTLPILEELHQ

R6:
(SEQ ID NO: 6)
HTEQLVQDQYGNRVIQHVLEHGRPEDKSIVAEIRG

R7:
(SEQ ID NO: 7)
NVLVLSQHKFASNVVEKCVTHASRTERAVLIDEVCTMNDGPHS

R8:
(SEQ ID NO: 8)
ALYTMMKDQYANYVVQKMIDVAEPGQRKIVMHKIRP (9)
R1:
(SEQ ID NO: 1)
HIMEFSQDQHGSRFIQLKLERATPAERQLVFNEILQ

R2:
(SEQ ID NO: 2)
AAYQLMVDVFGNYVIQKFFEFGSLEQKLALAERIRG

R5:
(SEQ ID NO: 5)
QVFALSTHPYGSYVIERILEHCLPDQTLPILEELHQ

R6:
(SEQ ID NO: 6)
HTEQLVQDQYGNYVIQHVLEHGRPEDKSIVAEIRG

R5:
(SEQ ID NO: 5)
QVFALSTHPYGSYVIERILEHCLPDQTLPILEELHQ

R6:
(SEQ ID NO: 6)
HTEQLVQDQYGNYVIQHVLEHGRPEDKSIVAEIRG

R5:
(SEQ ID NO: 5)
QVFALSTHPYGSYVIERILEHCLPDQTLPILEELHQ

R6:
(SEQ ID NO: 6)
HTEQLVQDQYGNYVIQHVLEHGRPEDKSIVAEIRG

R7:
(SEQ ID NO: 7)
NVLVLSQHKFASNVVEKCVTHASRTERAVLIDEVCTMNDGPHS

R8:
(SEQ ID NO: 8)
ALYTMMKDQYANYVVQKMIDVAEPGQRKIVMHKIRP

\<D\> An RNA-binding protein having an amino acid sequence represented by R1'-R1-R2-R5-R6-R5-R6-R7-R8-R8' (wherein R1', R8', and R1 to R8 are the amino acid sequences described below), wherein the protein has any of R1(S12N), R1(Q16E), R1(Q16R), R2(N12C), R2(N12S), R2(N12S, Q16E), R2(N12S, Q16R), R7(S12C, E16Q), R7(E16Q), R7(S12N, E16Q), R7(E16R), R8(N12C), R8(N12S), R8(N12S, Q16E), and R8(N12S, Q16R) as a substitution:

R1':
(SEQ ID NO: 9)
GRSRLLEDFRNNRYPNLQLREIAG;

R8':
(SEQ ID NO: 10)
HIATLRKYTYGKHILAKLEKYYMKNGVDLG;

R1:
(SEQ ID NO: 1)
HIMEFSQDQHGSRFIQLKLERATPAERQLVFNEILQ;

R2:
(SEQ ID NO: 2)
AAYQLMVDVFGNYVIQKFFEFGSLEQKLALAERIRG;

R5:
(SEQ ID NO: 5)
QVFALSTHPYGCRVIQRILEHCLPDQTLPILEELHQ;

R6:
(SEQ ID NO: 6)
HTEQLVQDQYGNYVIQHVLEHGRPEDKSIVAEIRG;

R7:
(SEQ ID NO: 7)
NVLVLSQHKFASNVVEKCVTHASRTERAVLIDEVCTMNDGPHS;

R8:
(SEQ ID NO: 8)
ALYTMMKDQYANYVVQKMIDVAEPGQRKIVMHKIRP.

<7> A nucleic acid encoding the RNA-binding protein according to any one of <1> to <6> and <A> to <D>.
<8> A recombinant expression vector including the nucleic acid according to <7>.
<9> A host cell including the recombinant expression vector according to <8>.

Advantageous Effects of Invention

According to the present invention, a soluble RNA-binding protein having high binding ability can be provided.

BRIEF DESCRIPTION OF THE DRAWINGS

FIG. 1 shows an amino acid sequence of RNA-binding protein. (SEQ ID NOS:2-8, 63,64)
FIG. 2 shows an amino acid sequence of RNA-binding protein. (SEQ ID NOS:1-8, 65,66)
FIG. 3 shows a result of gel shift assay.
FIG. 4 shows an amino acid sequence of RNA-binding protein. (SEQ ID NOS:1-8)
FIG. 5 shows a result of measurement of solubility of RNA-binding protein.
FIG. 6 shows a result of measurement of solubility of RNA-binding protein.
FIG. 7 shows a result of gel shift assay.
FIG. 8 shows an amino acid sequence of RNA-binding protein. (SEQ ID NOS:1,2, 5-8, 67)
FIG. 9 shows an amino acid sequence of RNA-binding protein. (SEQ ID NOS:1-3, 6-8, 68)
FIG. 10 shows a result of measurement of solubility of RNA-binding protein.
FIG. 11 shows a result of gel shift assay.
FIG. 12 shows an amino acid sequence of RNA-binding protein. (SEQ ID NOS:1,2, 5-8)
FIG. 13 shows a result of measurement of solubility of RNA-binding protein.
FIG. 14 shows a result of gel shift assay.
FIG. 15 shows an amino acid sequence of RNA-binding protein. (SEQ ID NOS:1,2, 5-8, 69,70)
FIG. 16 shows a result of gel shift assay.
FIG. 17 shows an amino acid sequence of RNA-binding protein. (SEQ ID NOS:1,2, 5-8)
FIG. 18 shows an amino acid sequence of RNA-binding protein. (SEQ ID NOS:1,5, 7, 8)
FIG. 19 shows a result of measurement of solubility of RNA-binding protein.
FIG. 20 shows a result of measurement of solubility of RNA-binding protein.
FIG. 21 shows a result of gel shift assay.
FIG. 22 shows an amino acid sequence of RNA-binding protein. (SEQ ID NOS:1-8,71)
FIG. 23 shows an amino acid sequence of RNA-binding protein. (SEQ ID NOS:1-6, 8, 72)
FIG. 24 shows a result of gel shift assay.
FIG. 25 shows a result of gel shift assay.
FIG. 26 shows an amino acid sequence of RNA-binding protein. (SEQ ID NOS:1-8)
FIG. 27 shows a result of gel shift assay.
FIG. 28 shows an amino acid sequence of RNA-binding protein. (SEQ ID NOS:1,2, 6-8, 73,74)
FIG. 29 shows a result of gel shift assay.
FIG. 30 shows a result of gel shift assay.
FIG. 31 shows an amino acid sequence of RNA-binding protein. (SEQ ID NOS:1,2, 5-8)
FIG. 32 shows a result of gel shift assay.
FIG. 33 shows an amino acid sequence of RNA-binding protein. (SEQ ID NOS:1,2, 5-8)
FIG. 34 shows an amino acid sequence of RNA-binding protein. (SEQ ID NOS:1,2, 5-8)
FIG. 35 shows a result of gel shift assay.
FIG. 36 shows an amino acid sequence of RNA-binding protein. (SEQ ID NOS:1,2, 5-8,75)
FIG. 37 shows an amino acid sequence of RNA-binding protein. (SEQ ID NOS:1,2, 6-8, 76,77)
FIG. 38 shows a result of gel shift assay.
FIG. 39 shows a result of gel shift assay.
FIG. 40 shows an amino acid sequence of RNA-binding protein. (SEQ ID NOS:1-3, 5-8,78)
FIG. 41 shows an amino acid sequence of RNA-binding protein. (SEQ ID NOS:1-3, 5, 7, 8,79, 80)
FIG. 42 shows a result of gel shift assay.
FIG. 43 shows a result of gel shift assay.
FIG. 44 shows an amino acid sequence of RNA-binding protein. (SEQ ID NOS:1-8, 81, 82)
FIG. 45 shows an amino acid sequence of RNA-binding protein. (SEQ ID NOS:1-8, 83, 84)
FIG. 46 shows a result of gel shift assay.
FIG. 47 shows an amino acid sequence of RNA-binding protein. (SEQ ID NOS:1,2,5-8, 85)
FIG. 48 shows an amino acid sequence of RNA-binding protein. (SEQ ID NOS:1,2,5-8, 86,87)
FIG. 49 shows an amino acid sequence of RNA-binding protein. (SEQ ID NOS:1,2,5-8, 88)
FIG. 50 shows a result of gel shift assay.
FIG. 51 shows an amino acid sequence of RNA-binding protein. (SEQ ID NOS:1,2,5-8, 89)
FIG. 52 shows a result of gel shift assay.
FIG. 53 shows an amino acid sequence of RNA-binding protein. (SEQ ID NOS:1,2,7,8, 90-92)
FIG. 54 shows an amino acid sequence of RNA-binding protein. (SEQ ID NOS:1,2,7,8, 90,91,93)
FIG. 55 shows a result of gel shift assay.
FIG. 56 shows an amino acid sequence of RNA-binding protein. (SEQ ID NOS:1,2,7,8, 90,94,95)
FIG. 57 shows an amino acid sequence of RNA-binding protein. (SEQ ID NOS:1,2,7,8, 90,93, 94)
FIG. 58 shows a result of gel shift assay.
FIG. 59 shows an amino acid sequence of RNA-binding protein. (SEQ ID NOS:1,2,7,8, 96-98)
FIG. 60 shows an amino acid sequence of RNA-binding protein. (SEQ ID NOS:1,2,7,8, 90,93,94)
FIG. 61 shows a result of gel shift assay.
FIG. 62 shows an amino acid sequence of RNA-binding protein. (SEQ ID NO:5, 6, 99,100)
FIG. 63 shows an amino acid sequence of RNA-binding protein. (SEQ ID NO:5, 6, 101)
FIG. 64 shows a result of gel shift assay.
FIG. 65 shows an amino acid sequence of RNA-binding protein. (SEQ ID NO:1,2,5-8)
FIG. 66 shows an amino acid sequence of RNA-binding protein. (SEQ ID NO:1,2,5-8)
FIG. 67 shows an amino acid sequence of RNA-binding protein. (SEQ ID NO:1,2,5-8)
FIG. 68 shows a result of gel shift assay.
FIG. 69 shows an amino acid sequence of RNA-binding protein. (SEQ ID NO:1,2,5-8)
FIG. 70 shows an amino acid sequence of RNA-binding protein. (SEQ ID NO:1,2,5-8)
FIG. 71 shows an amino acid sequence of RNA-binding protein. (SEQ ID NO:1,2,5-8)
FIG. 72 shows a result of gel shift assay.

FIG. 73 shows an amino acid sequence of RNA-binding protein. (SEQ ID NO:1,2,5-8)

FIG. 74 shows an amino acid sequence of RNA-binding protein. (SEQ ID NO:2,5-8, 102)

FIG. 75 shows an amino acid sequence of RNA-binding protein. (SEQ ID NO:2,5-8, 103)

FIG. 76 shows an amino acid sequence of RNA-binding protein. (SEQ ID NO:2,5-8, 104)

FIG. 77 shows a result of gel shift assay.

FIG. 78 shows a result of gel shift assay.

FIG. 79 shows an amino acid sequence of RNA-binding protein. (SEQ ID NO:1,2,5-8)

FIG. 80 shows a result of gel shift assay.

FIG. 81 shows an amino acid sequence of RNA-binding protein. (SEQ ID NO:1,2,5-8)

FIG. 82 shows an amino acid sequence of RNA-binding protein. (SEQ ID NO:1,5-8,105)

FIG. 83 shows an amino acid sequence of RNA-binding protein. (SEQ ID NO:1,5-8,106)

FIG. 84 shows an amino acid sequence of RNA-binding protein. (SEQ ID NO:1,5-8,107)

FIG. 85 shows an amino acid sequence of RNA-binding protein. (SEQ ID NO:1,5-8,108)

FIG. 86 shows a result of gel shift assay.

FIG. 87 shows an amino acid sequence of RNA-binding protein. (SEQ ID NO:1,2,5-8)

FIG. 88 shows an amino acid sequence of RNA-binding protein. (SEQ ID NO:1,5-8,109)

FIG. 89 shows an amino acid sequence of RNA-binding protein. (SEQ ID NO:1,5-8,110)

FIG. 90 shows an amino acid sequence of RNA-binding protein. (SEQ ID NO:1,5-8,111)

FIG. 91 shows a result of gel shift assay.

FIG. 92 shows an amino acid sequence of RNA-binding protein. (SEQ ID NO:1,2, 5-8)

FIG. 93 shows an amino acid sequence of RNA-binding protein. (SEQ ID NO:1,2,5,6,8,112)

FIG. 94 shows an amino acid sequence of RNA-binding protein. (SEQ ID NO:1,2,5,6,8,113)

FIG. 95 shows an amino acid sequence of RNA-binding protein. (SEQ ID NO:1,2,5,6,8,114)

FIG. 96 shows an amino acid sequence of RNA-binding protein. (SEQ ID NO:1,2,5,6,8,115)

FIG. 97 shows a result of gel shift assay.

FIG. 98 shows an amino acid sequence of RNA-binding protein. (SEQ ID NO:1,2, 5-8)

FIG. 99 shows an amino acid sequence of RNA-binding protein. (SEQ ID NO:1,2,5,6,8,116)

FIG. 100 shows an amino acid sequence of RNA-binding protein. (SEQ ID NO:1,2,5,6,8,117)

FIG. 101 shows an amino acid sequence of RNA-binding protein. (SEQ ID NO:1,2,5,6,8,118)

FIG. 102 shows a result of gel shift assay.

FIG. 103 shows an amino acid sequence of RNA-binding protein. (SEQ ID NO:1,2, 5-8)

FIG. 104 shows an amino acid sequence of RNA-binding protein. (SEQ ID NO:1,2,5-7,119)

FIG. 105 shows an amino acid sequence of RNA-binding protein. (SEQ ID NO:1,2,5-7,120)

FIG. 106 shows an amino acid sequence of RNA-binding protein. (SEQ ID NO:1,2,5-7,121)

FIG. 107 shows an amino acid sequence of RNA-binding protein. (SEQ ID NO:1,2,5-7,122)

FIG. 108 shows a result of gel shift assay.

FIG. 109 shows an amino acid sequence of RNA-binding protein. (SEQ ID NO:1,2, 5-8)

FIG. 110 shows an amino acid sequence of RNA-binding protein. (SEQ ID NO:1,2,5-7,123)

FIG. 111 shows an amino acid sequence of RNA-binding protein. (SEQ ID NO:1,2,5-7,124)

FIG. 112 shows an amino acid sequence of RNA-binding protein. (SEQ ID NO:1,2,5-7,125)

FIG. 113 shows a result of gel shift assay.

FIG. 114 shows explanation regarding verification of stacking amino acids.

FIG. 115 shows explanation regarding optimization of amino acids.

FIG. 116 shows an amino acid sequence of RNA-binding protein. (SEQ ID NO:1,2,7,8,126,127)

FIG. 117 shows an amino acid sequence of RNA-binding protein. (SEQ ID NO:1,2,7,8,128,129)

FIG. 118 shows an amino acid sequence of RNA-binding protein. (SEQ ID NO:1,2,7,8,130,131,132)

FIG. 119 shows a result of gel shift assay.

FIG. 120 shows explanation regarding optimization of amino acids.

FIG. 121 shows an amino acid sequence of RNA-binding protein. (SEQ ID NO:1,2,7,8,133,134)

FIG. 122 shows an amino acid sequence of RNA-binding protein. (SEQ ID NO:1,2,7,8,135,136)

FIG. 123 shows an amino acid sequence of RNA-binding protein. (SEQ ID NO:1,2,7,8,137-139)

FIG. 124 shows a result of gel shift assay.

FIG. 125 shows explanation regarding optimization of amino acids.

FIG. 126 shows an amino acid sequence of RNA-binding protein. (SEQ ID NO:1,2,7,8,140,141)

FIG. 127 shows an amino acid sequence of RNA-binding protein. (SEQ ID NO:1,2,7,8,142,143)

FIG. 128 shows an amino acid sequence of RNA-binding protein. (SEQ ID NO:1,2,7,8,144-146)

FIG. 129 shows a result of gel shift assay.

FIG. 130 shows explanation regarding verification of stacking amino acids.

FIG. 131 shows explanation regarding optimization of amino acids.

FIG. 132 shows an amino acid sequence of RNA-binding protein. (SEQ ID NO:1,2,5-8)

FIG. 133 shows an amino acid sequence of RNA-binding protein. (SEQ ID NO:1,2,5-8,147)

FIG. 134 shows an amino acid sequence of RNA-binding protein. (SEQ ID NO:1,2,5-8,148)

FIG. 135 shows an amino acid sequence of RNA-binding protein. (SEQ ID NO:1,2,5-8,149)

FIG. 136 shows an amino acid sequence of RNA-binding protein. (SEQ ID NO:1,2,5-8,150)

FIG. 137 shows an amino acid sequence of RNA-binding protein. (SEQ ID NO:1,2,5-8,151)

FIG. 138 shows a result of gel shift assay.

FIG. 139 shows explanation regarding optimization of amino acids.

FIG. 140 shows an amino acid sequence of RNA-binding protein. (SEQ ID NO:1,2,6-8,152)

FIG. 141 shows an amino acid sequence of RNA-binding protein. (SEQ ID NO:1,2,6-8,152,153)

FIG. 142 shows an amino acid sequence of RNA-binding protein. (SEQ ID NO:1,2,6-8,152,154)

FIG. 143 shows an amino acid sequence of RNA-binding protein. (SEQ ID NO:1,2,6-8,152,155)

FIG. 144 shows an amino acid sequence of RNA-binding protein. (SEQ ID NO:1,2,6-8,152,156)

FIG. 145 shows an amino acid sequence of RNA-binding protein. (SEQ ID NO:1,2,6-8,152,157)

FIG. 146 shows a result of gel shift assay.

FIG. 147 shows explanation regarding optimization of amino acids.

FIG. 148 shows an amino acid sequence of RNA-binding protein. (SEQ ID NO:1,2,6-8,158)

FIG. 149 shows an amino acid sequence of RNA-binding protein. (SEQ ID NO:1,2,6-8,158,159)

FIG. 150 shows an amino acid sequence of RNA-binding protein. (SEQ ID NO:1,2,6-8,160)

FIG. 151 shows an amino acid sequence of RNA-binding protein. (SEQ ID NO:1,2,6-8,158,161)

FIG. 152 shows an amino acid sequence of RNA-binding protein. (SEQ ID NO:1,2,6-8,158,162)

FIG. 153 shows an amino acid sequence of RNA-binding protein. (SEQ ID NO:1,2,6-8,163)

FIG. 154 shows a result of gel shift assay.

FIG. 155 shows explanation regarding optimization of amino acids.

FIG. 156 shows an amino acid sequence of RNA-binding protein. (SEQ ID NO:1,2,6-8,164)

FIG. 157 shows an amino acid sequence of RNA-binding protein. (SEQ ID NO:1,2,6-8,165)

FIG. 158 shows an amino acid sequence of RNA-binding protein. (SEQ ID NO:1,2,6-8,166)

FIG. 159 shows an amino acid sequence of RNA-binding protein. (SEQ ID NO:1,2,6-8,167)

FIG. 160 shows an amino acid sequence of RNA-binding protein. (SEQ ID NO:1,2,6-8,168)

FIG. 161 shows an amino acid sequence of RNA-binding protein. (SEQ ID NO:1,2,6-8,169)

FIG. 162 shows a result of gel shift assay.

FIG. 163 shows the regularity of wild-type stacking amino acids.

EMBODIMENT OF CARRYING OUT THE INVENTION

The RNA-binding protein of the present invention is an RNA-binding protein comprising a plurality of repeat motifs, which has an N-terminal domain bound to the N terminus of the plurality of repeat motifs and a C-terminal domain bound to the C terminus thereof.

The N-terminal domain is referred to as "R1' domain" and the C-terminal domain is referred to as "R8' domain." The amino acid sequence of the R1' domain and the amino acid sequence of the R8' domain are as follows.

```
R1':
                                      (SEQ ID NO: 9)
GRSRLLEDFRNNRYPNLQLREIAG

R8':
                                      (SEQ ID NO: 10)
HIATLRKYTYGKHILAKLEKYYMKNGVDLG;
```

The following findings were obtained in the Examples of the present invention.

It was found in Example 1 that when Phe, the 5th or 14th amino acid residue of R1, is substituted with Ala, the binding force decreases, and even when Phe, the 18th amino acid residue of R2, is substituted with Ala does not affect the binding force. In other words, it was suggested that Phe, the 5th or 14th amino acid residue of R1, is involved in the interaction between RNA and a protein.

Solubility and binding ability of an RNA-binding protein with a recognition repeat substitution were examined in Example 2.

As a result, an RNA-binding protein having a substitution of R3 with R5 was soluble, and an RNA-binding protein having a substitution of R4 with R6 was also soluble, both of which had binding ability comparable to that of the wild-type protein.

In addition, an RNA-binding protein having a substitution of R3 with R5 and a substitution of R4 with R5 was soluble and had binding ability. An RNA-binding protein having a substitution of R3 with R5 and a substitution of R4 with R5, which was modified to have a substitution of the 13th amino acid residue, Arg, with His, was also found to have binding ability comparable to the above level.

In addition, an RNA-binding protein having a substitution of R3 with R5 and a substitution of R4 with R6 was soluble and had binding ability comparable to that of the wild-type protein.

It was indicated that for R7-R8 binding, the terminal sequence of R7 is preferably ILQ or IRG, and more preferably ILQ.

Binding ability of an RNA-binding protein having extended recognition repeat(s) was examined in Example 3. As a result, it was suggested that high binding ability can be achieved with a plurality of R5-R6 repeats.

An RNA-binding protein with modified recognition specificity for R5 was prepared and the binding ability was examined in Example 4. As a result, it was found that the degree of the binding ability is in the following order: C12N (recognition of U (hereinafter "U recognition"))>C12S, Q16E (recognition of G (hereinafter "G recognition")) >C12S, Q16R (recognition of C (hereinafter "C recognition"))>MT (R3→R5, R4→R5) (recognition of A (hereinafter "A recognition")).

In addition, an RNA-binding protein with modified recognition specificity for R6 was prepared and the binding ability was examined. As a result, it was indicated that in the cases of G recognition and C recognition, the protein has binding ability comparable to that of the wild-type protein in the case of U recognition.

The optimal amino acid was examined by modifying U-A and A-U stacking amino acids in Example 5. As a result, it was indicated that Arg can be used as a cationic amino acid between A and U (A-U), and Trp, Tyr, Phe, and His can be used as an aromatic amino acid between U and A (U-A).

The optimal amino acid was examined by modifying A-C and C-A stacking amino acids in Example 5. As a result, it was indicated that Tyr is suitable as an aromatic amino acid between C and A (C-A), and Arg is suitable as a cationic amino acid between A and C (A-C).

In addition, it was indicated that Tyr is suitable as an aromatic amino acid between G and A (G-A), and Arg is suitable as a cationic amino acid between A and G (A-G).

In addition, it was indicated that Arg is suitable as a cationic amino acid between U and G (U-G), and Arg is suitable as a cationic amino acid between G and U (G-U).

Between A and A (A-A), binding ability of an aromatic amino acid was stronger than that of an cationic amino acid. Among aromatic amino acids, Tyr and His had high binding ability.

TABLE 1

| 13th Stacking Amino Acid | | | | | |
|---|---|---|---|---|---|
| Between purine and purine | | | Between Pyrimidine and purine | | |
| A-A | A-G | G-A | U-A | U-G | C-A |
| Tyr | Arg | Tyr | Tyr | Arg | Tyr |
| His | | | | | |

| Between purine and pyrimidine | | |
|---|---|---|
| A-U | A-C | G-U |
| Arg | Arg | Arg |

The binding ability of an RNA-binding protein with further extended recognition repeats was examined in Example 7. Considering the superiority and inferiority of the binding ability together with the results of Example 3, it was found that the binding force decreases in the following order from (1) to (4).
  (1) 12, 13 repeats,
  (2) 10, 11, 14 repeats,
  (3) 9, 15 repeats, and
  (4) WT, 8, 16 repeats.

The binding ability of each RNA-binding protein was examined by changing recognition specificity in Example 8 in the same manner as in Example 4. In particular, the recognition specificity was changed for R1, R2, R7, and R8, and the effects were confirmed by experiments. Based on the experimental results, the RNA recognition specificity of each protein having the corresponding amino acid sequence was clarified, and the order of binding strength was elucidated.

In Example 9, the optimal amino acid was confirmed by modifying each stacking amino acid as in Example 5. Table 2 below shows the results together with the results obtained in Example 5.

TABLE 2

| RNA Recognition Code Table | | | |
|---|---|---|---|
| 12th & 16th Base Recognition Amino Acids | | | |
| Recognition of A | Recognition of U | Recognition of G | Recognition of C |
| 12C 16Q | 12N 16Q | 12S 16E | 12S 16R |
| 12S 16Q | | | |

| 13th Stacking Amino Acid | | | | | | | |
|---|---|---|---|---|---|---|---|
| Between purine and purine | | | | Between Pyrimidine and purine | | | |
| A-A | A-G | G-A | G-G | U-A | U-G | C-A | C-G |
| Tyr | Arg | Tyr | Arg | Tyr | Arg | Tyr | Arg |
| His | | | His | | | | |

| Between purine and pyrimidine | | | | Between purine and pyrimidine | | | |
|---|---|---|---|---|---|---|---|
| A-U | A-C | G-U | G-C | U-U | U-C | C-U | C-C |
| Arg | Arg | Arg | Arg | Trp | Tyr | Tyr | Phe |
| His | | | | Arg | | | |

By utilizing the knowledge of the present invention, it is possible to design an artificial RNA-binding protein that specifically recognizes the RNA virus genome sequence with high affinity.

<Gene Encoding RNA-Binding Protein>

A method for preparing a gene encoding the RNA-binding protein of the present invention is not particularly limited. However, the gene can be prepared by chemical synthesis of a nucleic acid based on the amino acid sequences disclosed herein.

<Solubilization of RNA-Binding Protein>

In order to improve solubilization of an RNA-binding protein, it is possible to fuse a tag protein that is known to promote solubilization. A maltose-binding protein (MBP) or the like can be used as a tag protein.

<Purification of RNA-Binding Protein>

A recombinant expression vector can be prepared by incorporating a nucleic acid encoding an MBP-tagged RNA-binding protein into an expression vector. A recombinant expression vector can be introduced into a host for expression, thereby allowing each protein to be expressed in the host.

(1) Production of Recombinant Expression Vector

A vector into which the nucleic acid encoding the RNA-binding protein of the present invention is inserted is not particularly limited as long as it can be replicated in a host. Examples thereof include plasmid DNA and phage DNA.

Examples of plasmid DNA include *Escherichia coli*-derived plasmids (e.g., pET System, pRSET, pBR322, pBR325, pUC118, pUC119, pUC18, and pUC19), *Bacillus subtilis*-derived plasmids (e.g., pUB110 and pTP5), yeast-derived plasmids (e.g., YEp13, YEp24, and YCp50). Examples of phage DNA include λ, phages (e.g., Charon4A, Charon21A, EMBL3, EMBL4, λgt10, λgt11, and λZAP). In addition, animal viruses such as retrovirus and vaccinia virus, and insect virus vectors such as baculovirus can be used.

The nucleic acid (DNA) encoding the RNA binding protein can be inserted into a vector by cleaving the nucleic acid encoding the RNA-binding protein with an appropriate restriction enzyme and inserting it into the restriction enzyme site or multicloning site in the vector.

The nucleic acid encoding the RNA-binding protein must be incorporated into a vector so that the function of the gene can be exerted. In other words, the vector of the present invention may optionally include a cis-element such as an enhancer, a splicing signal, a poly A addition signal, a selection marker, a ribosome-binding sequence (SD sequence), and the like, in addition to a promoter and the nucleic acid encoding the RNA-binding protein. Examples of a selection marker include a dihydrofolate reductase gene, an ampicillin resistance gene, and a neomycin resistance gene.

(2) Production of Transformant

The present invention also relates to a host cell (transformant) including the above-described expression vector. A transformant can be obtained by introducing a recombinant expression vector into a host such that a desired gene (i.e., a nucleic acid encoding an RNA-binding protein) can be expressed. The host is not particularly limited as long as the nucleic acid of the present invention can be expressed.

Examples of the host include bacteria belonging to the genus *Escherichia* (e.g., *Escherichia coli*), the Genus *Bacillus* (*Bacillus subtilis*), the genus *Pseudomonas* (e.g., *Pseudomonas putida*), and the genus *Rhizobium* (e.g., *Rhizobium meliloti*). The host may be a yeast such as *Saccharomyces cerevisiae* or *Schizosaccharomyces pombe*. Further, the host may be an animal cell such as a COS cell or CHO cell or an insect cell of Sf9, Sf21, or the like.

In a case in which a bacterium such as *Escherichia coli* is designated as a host, it is preferable that the recombinant expression vector of the present invention can replicate autonomously in a bacterium, and at the same time, it is composed of a promoter, a ribosome-binding sequence, a nucleic acid encoding an RNA-binding protein, and a transcription termination sequence. The vector may also include a gene regulating a promoter.

Examples of *Escherichia coli* include *Escherichia coli* K12 and DH1, and *Bacillus subtilis* or the like can be exemplified. Any promoter may be used as long as it can be expressed in a host such as *Escherichia coli*. For example, *Escherichia coli*-derived promoters and phage-derived promoters such as a trp promoter, a lac promoter, a PL promoter, and a PR promoter can be used. An artificially designed and modified promoter such as a tac promoter may be used. A method for introducing the recombinant vector into a bacterium is not particularly limited as long as it is a method for introducing DNA into a bacterium. For example, a method using calcium ions, an electroporation method, and the like can be mentioned.

In a case in which a yeast is used as a host, for example, *Saccharomyces cerevisiae, Schizosaccharomyces pombe, Pichia pastoris*, or the like can be used. In such case, a promoter is not particularly limited as long as it can be expressed in a yeast. Examples thereof include a gal1 promoter, a gal10 promoter, a heat-shock protein promoter, an MFα1 promoter, a PHO5 promoter, a PGK promoter, a GAP promoter, a ADH promoter, and an AOX1 promoter. A method for introducing the recombinant vector into a yeast is not particularly limited as long as it is a method for introducing DNA into a yeast. For example, an electroporation method, a spheroplast method, a lithium acetate method, and the like can be mentioned.

In a case in which animal cells are used as a host, monkey cells such as COS-7 cells and Vero cells, Chinese hamster ovary cells (CHO cells), mouse L cells, rat GH3 cells, human FL cells, and the like are used. An SRα promoter, SV40 promoter, LTR promoter, CMV promoter, or the like may be used as a promoter. In addition, an early gene promoter of human cytomegalovirus or the like may also be used. Examples of a method for introducing the recombinant vector into animal cells include an electroporation method, a calcium phosphate method, and a lipofection method.

In a case in which insect cells are used as a host, SD cells, Sf21 cells, and the like are used. Examples of a method for introducing the recombinant vector into insect cells include a calcium phosphate method, a lipofection method, and an electroporation method.

(3) Production of RNA-Binding Protein

The RNA-binding protein of the present invention can be obtained by culturing the above-described transformant and collecting the protein from the culture product. The term "culture product" means any of cultured cells/cultured bacterial cells or disrupted cells/bacterial cells, in addition to a culture supernatant. A method for culturing the transformant is carried out in accordance with an ordinary method applied for culturing a host.

Each of a natural medium and a synthetic medium may be used as a medium for culturing a transformant obtained using a microorganism such as *E. coli* or yeast as a host as long as it is a medium which contains a carbon source, a nitrogen source, an inorganic salt, and the like that can be assimilated by the microorganism such that the transformant can be cultured efficiently. Carbohydrates such as glucose, fructose, sucrose, and starch, organic acids such as acetic acid and propionic acid, and alcohols such as ethanol and propanol are used as carbon sources. Ammonium salts of inorganic acids or organic acids such as ammonia, ammonium chloride, ammonium sulfate, ammonium acetate, and ammonium phosphate or other nitrogen-containing compounds, peptone, meat extract, corn steep liquor, and the like are used as nitrogen sources. Potassium phosphate, dipotassium phosphate, magnesium phosphate, magnesium sulfate, sodium chloride, ferrous sulfate, manganese sulfate, copper sulfate, and calcium carbonate are used as inorganic substances.

Culture is usually carried out at 37° C. for 6 to 24 hours under aerobic conditions such as shake culture or aeration and agitation culture. The pH is maintained at 7.0 to 7.5 during the culture period. The pH is adjusted using an inorganic or organic acid, an alkaline solution, or the like. Antibiotics such as ampicillin and tetracycline may be added to the medium as necessary during culture.

When culturing a microorganism transformed with an expression vector using an inducible promoter as a promoter, an inducer may be added to the medium as necessary. For example, when culturing a microorganism transformed with an expression vector using a Lac promoter, isopropyl-3-D-thiogalactopyranoside (IPTG) or the like may be added to the medium, and when culturing a microorganism transformed with an expression vector using a trp promoter, indoleacrylic acid (IAA) or the like may be added to the medium.

A generally used RPMI 1640 medium or DMEM medium, a medium obtained by adding fetal bovine serum or the like to any of these media, or the like is used as a medium for culturing a transformant obtained using animal cells as a host. Culture is usually performed at 37° C. for 1 to 30 days in the presence of 5% $CO_2$. Antibiotics such as kanamycin and penicillin may be added to the medium as necessary during culture.

After culture, in a case in which the RNA-binding protein of the present invention is produced inside of cells or bacterial cells, the RNA-binding protein is extracted by disrupting the cells or bacterial cells. In addition, in a case in which the RNA-binding protein of the present invention is produced outside of cells or bacterial cells, the culture solution is directly used or the cells or bacterial cells are removed therefrom by centrifugation or the like. Thereafter, the RNA-binding protein of the present invention can be isolated and purified from the culture product by using any one of or an appropriate combination of general biochemical methods used for protein isolation and purification, such as ammonium sulfate precipitation, gel chromatography, ion exchange chromatography, and affinity chromatography.

<Comparison/Evaluation of Binding Ability by Gel Shift Assay>

It is possible to evaluate whether or not the RNA-binding protein of the present invention binds to a target sequence by gel shift assay.

A target RNA probe labeled with Alexa680 with absorption at 680 nm in the far infrared range (final concentration: 0.5 nM) and the RNA-binding protein (final concentration: 10 to 1000 nM) are mixed at 4° C. for 1 hour in a reaction buffer (10 mM Tris-HCl, pH 7.5, 100 mM NaCl, 1 mM EDTA, 1 mM DTT, 10% Glycerol, 0.05% BSA, 0.2 U RNase inhibitor) and then applied to 6% non-denaturing polyacrylamide gel equilibrated with 0.5×TBE buffer (size: 16×16 cm; thickness: 1 mm), followed by electrophoresis in a cold room (4° C.). Each band of RNA can be visualized by terminating electrophoresis when the dye marker flows 3 cm and detecting the fluorescence in the gel taken out from the device while scanning with a far-infrared detector.

EXAMPLES

Example 1: Verification of Interaction Via Phe (1) Vector Cloning

FIGS. 1 and 2 show the amino acid sequences of hPUF_MT(F856A), MT(F865A), MT(F856A/F865A), and MT(905A). Total synthesis of genes encoding hPUF_MT (F856A), MT(F865A), MT(F856A/F865A), and MT(905A) was carried out. Synthesized genes were cleaved with BsaI and ligated with pET24-MBP(—B)—R1'-MSC—R8' which was also cleaved with BsaI, thereby constructing expression vectors. pET24-MBP(—B)—R1'-MSC—R8' is a vector composed of a pET24 vector including a gene encoding a maltose-binding protein (MBP), a gene encoding R1', a multicloning site, and a gene encoding R8'.

(2) Protein Expression and Purification

Each obtained expression vector was transduced into *E. coli* BL21 (DE3). Protein expression was induced by performing shake culture in an LB-Kan medium containing 2% glucose until $OD_{600}$ reached a level of about 0.6 to 0.75, followed by shake culture in a 1 mM IPTG-containing LB-Kan medium at 37° C. for 3 h. *E. coli* was pelleted and suspended in a lysis buffer (25 mM Tris-HCl (pH 8.0), 500 mM NaCl). Each desired protein was adsorbed by performing freeze-thawing and sonication, mixing the centrifuged supernatant with Profinity™ IMAC Ni-Charged Resin (Biorad), followed by rotoring at 4° C. for 10 h. After washing with a buffer containing 25 mM Tris-HCl (pH 8.0) and 500 mM NaCl and then with a buffer containing 25 mM Tris-HCl (pH 8.0), 500 mM NaCl, and 20 mM imidazole, elution was performed with a buffer containing 25 mM Tris-HCl (pH 8.0), 500 mM NaCl, and 150 mM imidazole. The buffer was exchanged to a buffer containing 50 mM Tris-HCl (pH 7.5) and 300 mM NaCl and concentrated by ultrafiltration. The concentrate was mixed with 99.5% glycerol and 1M DTT such that the mixture had a composition of 25 mM Tris-HCl (pH 7.5), 150 mM NaCl, 50% glycerol, and 5 mM DTT, and then, stored at –20° C.

(3) Gel Shift Assay

An RNA probe (OTS-1511) containing a target sequence fluorescence-labeled with Alexa680 at both ends thereof was synthesized.

```
OTS-1511:
                                    (SEQ ID NO: 30)
5'-Alexa680-CCAGAAUUGUAUAUAUUCG-Alexa680-3'

(19 mer)
```

Each purified protein was diluted to a desired concentration with Binding Buffer, mixed with a binding buffer and Ribonuclease Inhibitor, Cloned (Invitrogen), and then, mixed with the RNA probe at a final concentration of 0.5 nM. A buffer in a binding reaction had a composition of 10% glycerol, 100 mM NaCl, 10 mM Tris-HCl (pH 7.5), 0.05% BSA, Ribonuclease Inhibitor (0.2 U), 1 mM DTT, and 1 mM EDTA. A binding reaction was performed at 4° C. for 30 min. Subsequently, the solution was gently mixed by pipetting. A binding reaction was performed again at 4° C. for 30 mM.

The solution obtained after the binding reaction was applied to 6% a non-denaturing polyacrylamide gel, followed by electrophoresis at 4° C. and 200 V. When the electrophoresis marker (2 μL of 6×Dye+10 μL of 1×binding buffer) moved by 0.5 cm, the voltage was changed to 100 V, and electrophoresis was continuously performed until the electrophoresis marker moved by 3 cm. Finally, RNA was detected with Odyssey.

FIG. 3 shows the results.

When Phe856 and Phe865 were each substituted with Ala, the binding force decreased (about 1/10). Substitution of Phe905 with Ala did not significantly affect the binding force.

The degree of contribution to binding force was found to be in the order of Phe856>Phe865>>Phe905.

Example 2: Confirmation of Recognition Repeats

Example 2-1

(1) Vector Cloning

FIG. 4 shows the amino acid sequences of hPUF_MT (R3→R5) and MT(R4→R6).

Total synthesis of genes encoding hPUF_MT(R3→R5) and MT(R4→R6) was carried out. Synthesized genes were cleaved with BsaI and ligated with pET24-R1'-MSC—R8' which was also cleaved with BsaI, thereby constructing expression vectors.

(2) Protein Expression and Purification

Protein expression and purification were performed by the same procedures as in (2) of Example 1. Note that protein expression was induced in a 0.01 mM IPTG-containing LB-Kan medium at 25° C. for 16 h. Rotoring for absorption to the resin was carried out for 8 h. FIGS. 5 and 6 show the results of examining solubility.

(3) Gel Shift Assay

Gel shift assay was performed by the same procedures as in (3) of Example 1

The following RNA probe was used.

```
OTS-1511:
                                    (SEQ ID NO: 30)
5'-Alexa680-CCAGAAUUGUAUAUAUUCG-Alexa680-3'

(19 mer)
```

FIG. 7 shows the results. Both MT(R3→R5) and MT(R4→R6) were found to have binding force comparable to that of the wild type.

Example 2-2

(1) Vector Cloning

FIGS. 8 and 9 show the amino acid sequences of hPUF_MT(R3→R5, R4→R5), hPUF_MT(R3→R5, R4→R5_R13H), hPUF_MT(R4→R6, R5→R6), and hPUF_MT(R4→R6, R5→R6_Y13R).

Vector cloning was performed by the same procedures as in Example 2-1.

(2) Protein Expression and Purification

Protein expression and purification were performed by the same procedures as in Example 1. Note that protein expression was induced in a 0.01 mM IPTG-containing LB-Kan medium at 30° C. for 7 h. Rotoring for absorption to the resin was carried out for 10 h.

FIG. 10 shows the results of examining solubility.

(3) Gel Shift Assay

Gel shift assay was performed by the same procedures as in Example 1.

The following RNA probes were used.

```
OTS-1511:
                                        (SEQ ID NO: 30)
5'-Alexa680-CCAGAAUUGUAUAUAUUCG-Alexa680-3'

(19 mer) (probe for the wild type)

OTS-1759:
                                        (SEQ ID NO: 31)
5'-Alexa680-CCAGAAUUGUAAAUAUUCG-Alexa680-3'

(19 mer) (hPUF_MT(R3→R5, R4→R5),
```

MT (probe for R3→R5, R4→R5_R13H)

FIG. 11 shows the results.

Example 2-3

(1) Vector Cloning

FIG. 12 shows the amino acid sequences of hPUF_MT (R3→R5, R4→R6) and hPUF_MT(1-6-5-6-5-6-7-8).

Vector cloning was performed by the same procedures as in Example 2-1.

(2) Protein Expression and Purification

Protein expression and purification of hPUF_MT (R3→R5, R4→R6) and hPUF_MT(1-6-5-6-5-6-7-8) were performed by the same procedures as in Example 1. Note that protein expression induction was carried out under the following conditions.

hPUF_MT(R3→R5, R4→R6): 25° C. for 16 h in a 0.01 mM IPTG-containing LB-Kan medium hPUF_MT(1-6-5-6-5-6-7-8): 37° C. for 3 h in a 1 mM IPTG-containing LB-Kan medium Rotoring for absorption to the resin was carried out for 10 h for hPUF_MT(R3→R5, R4→R6) and for 14 h for hPUF_MT(1-6-5-6-5-6-7-8).

Protein expression and purification of hPUF_MT (R4→R6, R5→R6) and hPUF_MT(R4→R6, R5→R6 Y13R) were performed by the following procedures. Each obtained expression vector was transduced into *E. coli* BL21(DE3)/pKJE7. Protein expression was induced by performing shake culture in an LB-Cm-Kan medium containing 0.5 mg/mL arabinose until $OD_{600}$ reached a level of about 0.4 to 0.8, and IPTG was added to the medium so as to yield a final concentration of 0.1 mM, followed by shake culture the medium at 30° C. for 7 h. *E. coli* was pelleted and suspended in a lysis buffer (25 mM Tris-HCl (pH 8.0), 500 mM NaCl). Each desired protein was adsorbed by performing freeze-thawing and sonication, mixing the centrifuged supernatant with Profinity™ IMAC Ni-Charged Resin (Biorad), followed by rotoring at 4° C. for 14 h. After washing with a buffer containing 25 mM Tris-HCl (pH 8.0) and 500 mM NaCl and then with a buffer containing 25 mM Tris-HCl (pH 8.0), 500 mM NaCl, and 20 mM imidazole, elution was performed with a buffer containing 25 mM Tris-HCl (pH 8.0), 500 mM NaCl, and 150 mM imidazole. The buffer was exchanged to a buffer containing 50 mM Tris-HCl (pH 7.5) and 300 mM NaCl and concentrated by ultrafiltration. The concentrate was mixed with 99.5% glycerol and 1M DTT such that the mixture had a composition of 25 mM Tris-HCl (pH 7.5), 150 mM NaCl, 50% glycerol, and 5 mM DTT, and then, stored at −20° C.

FIG. 13 shows the results of examining solubility.

(3) Gel Shift Assay

Gel shift assay was performed by the same procedures as in Example 1. Note that as the protein concentration could not be measured for hPUF_MT(R4→R6, R5→R6) and hPUF_MT(R4→R5→R6_Y13R), stock solutions of their purification samples were used without dilution.

The following RNA probes were used.

```
OTS-1511:
                                        (SEQ ID NO: 30)
5'-Alexa680-CCAGAAUUGUAUAUAUUCG-Alexa680-3'

(19 mer) (probe for the wild type, hPUF_MT(R3→R5,

R4→R6), MT(1-6-5-6-5-6-7-8))

OTS-1760:
                                        (SEQ ID NO: 32)
5'-Alexa680-CCAGAAUUGUUUAUAUUCG-Alexa680-3'

(19 mer) (probe for hPUF_MT(R4→R6, R5→R6),

MT(R4→R6, R5→R6_Y13R))
```

FIG. 14 shows the results. The binding force of hPUF_MT(1-6-5-6-5-6-7-8) was about one-tenth of that of the wild type (Kd: 50 to 10 nM). Electrophoresis of the R6×3 mutant was unsuccessful because of clogging of wells.

Example 2-4

(1) Vector Cloning

FIG. 15 shows the amino acid sequences of hPUF_MT (1-2-5-6-5-6-5_ILQ-8) and hPUF_MT(1-6-5-6-5-6-5-6_IRP).

Vector cloning was performed by the same procedures as in Example 2-1.

(2) Protein Expression and Purification

Protein expression and purification were performed by the same procedures as in Example 1.

Note that protein expression induction was carried out under the following conditions.

hPUF_MT(1-2-5-6-5-6-5_ILQ-8): 37° C. for 3 h in a 0.1 mM IPTG-containing LB-Kan medium hPUF_MT(1-2-5-6-5-6-5-6_IRP): 37° C. for 3 h in a 0.1 mM IPTG-containing LB-Kan medium Rotoring for absorption to the resin was carried out for 14 h.

(3) Gel Shift Assay

Gel shift assay was performed by the same procedures as in Example 1.

The following RNA probes were used.

```
OTS-1511:
                                        (SEQ ID NO: 30)
5'-Alexa680-CCAGAAUUGUAUAUAUUCG-Alexa680-3'

(19 mer) (wild-type probe)

OTS-1754:
                                        (SEQ ID NO: 33)
5'-Alexa680-CCAGAAUUAUAUAUAUUCG-Alexa680-3'

(19 mer) (probe for hPUF_MT(1-2-5-6-5-6-5_ILQ-8),

MT(1-2-5-6-5-6-5-6_IRP))
```

FIG. 16 shows the results.

MT(1-2-5-6-5-6-5_ILQ-8) and MT(1-2-5-6-5-6-5-6_IRP) are thought to have binding force weaker than that of the wild type (WT).

Example 2-5

(1) Vector Cloning

FIGS. 17 and 18*h* show the amino acid sequences of PUF_MT(1-5-5-5-5-6-7-8), hPUF_MT(1-2-5-6-5-6-5-6-7-8), and hPUF_MT(1-5-5-5-5-5-7-8).

Vector cloning was performed by the same procedures as in Example 2-1.

(2) Protein Expression and Purification

Protein expression and purification were performed by the same procedures as in Example 1.

Note that protein expression induction was carried out under the following conditions.

hPUF_MT(1-5-5-5-5-6-7-8): 20° C. for 24 h in a 1 mM IPTG-containing LB-Kan medium hPUF_MT(1-2-5-6-5-6-5-6-7-8): 37° C. for 3 h in a 1 mM IPTG-containing LB-Kan medium Rotoring for absorption to the resin was carried out for 10 h.

FIGS. 19 and 20 show the results of examining solubility.

(3) Gel Shift Assay

Gel shift assay was performed by the same procedures as in Example 1.

The following RNA probes were used.

```
OTS-1511:
                                         (SEQ ID NO: 30)
5'-Alexa680-CCAGAAUUGUAUAUAUUCG-Alexa680-3'

(19 mer) (probe for the wild type)

OTS-1818:
                                         (SEQ ID NO: 34)
5'-Alexa680-CCAGAAUUGUAAAAAUUCG-Alexa680-3'

(19 mer) (probe for hPUF_MT(1-5-5-5-5-6-7-8))

OTS-1844:
                                         (SEQ ID NO: 35)
5'-Alexa680-CCAGAAUUGUAUAUAUAUUCG-Alexa680-3'

(21 mer) (probe for hPUF_MT(1-2-5-6-5-6-5-6-7-8))
```

FIG. 21 shows the results. It was found that MT(1-5-5-5-5-6-7-8) has binding force weaker than that of WT, and MT(1-2-5-6-5-6-5-6-7-8) has binding ability almost comparable to that of WT.

Example 2-6

(1) Vector Cloning

FIGS. 22 and 23 show the amino acid sequences of hPUF_MT(R7→R5), hPUF_MT(R7_ILQ), and hPUF_MT(R7_IRG).

Vector cloning was performed by the same procedures as in Example 2-1.

(2) Protein Expression and Purification

Protein expression and purification were performed by the same procedures as in Example 1. Note that protein expression induction was carried out under the following conditions.

hPUF_MT(R7→R5): 25° C. for 16 h in a 0.01 mM IPTG-containing LB-Kan medium hPUF_MT(R7_IRG): 25° C. for 16 h in a 0.01 mM IPTG-containing LB-Kan medium hPUF_MT(R7_ILQ): 25° C. for 13 h in a 1 mM IPTG-containing LB-Kan medium Rotoring for absorption to the resin was carried out for 13 h.

(3) Gel Shift Assay

Gel shift assay was performed by the same procedures as in Example 1.

The following RNA probes were used.

```
OTS-1511:
                                         (SEQ ID NO: 30)
5'-Alexa680-CCAGAAUUGUAUAUAUUCG-Alexa680-3'

(19 mer) (probe for the wild type, hPUF_MT(R7_ILQ), MT(R7_IRG))

OTS-1754:
                                         (SEQ ID NO: 33)
5'-Alexa680-CCAGAAUUAUAUAUAUUCG-Alexa680-3'

(19 mer) (probe for hPUF_MT(R7→R5))
```

FIG. 24 shows the results. MT(R7→R5) has binding force weaker than that of WT, and the position of the shifted band is higher than expected. MT(R7_ILQ) and MT(R7_IRG) had binding force almost comparable to that of WT.

Example 2-7

(1) Vector Cloning

The same vector as in Example 2-6 was used.

(2) Protein Expression and Purification

Protein expression and purification were performed by the same procedures as in Example 2-6.

(3) Gel Shift Assay

Gel shift assay was performed by the same procedures as in Example 1. The following RNA probe was used.

```
OTS-1511:
                                         (SEQ ID NO: 30)
5'-Alexa680-CCAGAAUUGUAUAUAUUCG-Alexa680-3'

(19 mer)
```

FIG. 25 shows the results. It is understood that ILQ is a terminal sequence suitable for R7-R8 ligation.

Example 2-8

(1) Vector Cloning

FIG. 26 shows the amino acid sequences of hPUF_MT (R7→R5) and hPUF_MT(R8→R5).

Vector cloning was performed by the same procedures as in Example 2-1.

(2) Protein Expression and Purification

Protein expression and purification were performed by the same procedures as in Example 1.

Note that protein expression was induced in a 1 mM IPTG-containing LB-Kan medium at 37° C. for 3 h.

Rotoring for absorption to the resin was carried out for 8 h.

(3) Gel Shift Assay

Gel shift assay was performed by the same procedures as in Example 1.

The following RNA probes were used.

```
OTS-1511:
                                         (SEQ ID NO: 30)
5'-Alexa680-CCAGAAUUGUAUAUAUUCG-Alexa680-3'

(19 mer) (probe for the wild type, hPUF_MT(R7_ILQ), MT(R7_IRG))
```

```
OTS-1754:
                                   (SEQ ID NO: 33)
5'-Alexa680-CCAGAAUUAUAUAUAUUCG-Alexa680-3'

(19 mer) (probe for hPUF_MT(R7→R5))

OTS-1825:
                                   (SEQ ID NO: 36)
5'-Alexa680-CCAGAAUAGUAUAUAUUCG-Alexa680-3'

(19 mer) (probe for hPUF_MT(R8→R5))
```

FIG. 27 shows the results. MT(R7→R5) has binding force that is significantly weaker than that of WT, and MT(R8→R5) is thought to have substantially no binding ability.

Example 2-9

(1) Vector Cloning

FIG. 28 shows the amino acid sequences of hPUF_MT (R3→RC, R4→RC, R5→RC) and hPUF_MT(R3→RC2, R4→RC2, R5→RC2).

Vector cloning was performed by the same procedures as in Example 2-1.

(2) Protein Expression and Purification

Protein expression and purification were performed by the same procedures as in Example 1.

Note that protein expression induction was carried out under the following conditions.

hPUF_MT(R3→RC, R4→RC, R5→RC): 37° C. for 3 h in a 1 mM IPTG-containing LB-Kan medium hPUF_MT(R3→RC2,R4→RC2,R5→RC2): 37° C. for 3 h in a 1 mM IPTG-containing LB-Kan medium Rotoring for absorption to the resin was carried out for 9 h.

(3) Gel Shift Assay

Gel shift assay was performed by the same procedures as in Example 1.

The following RNA probe was used.

```
OTS-1759:
                                   (SEQ ID NO: 31)
5'-Alexa680-CCAGAAUUGUAAAUAUUCG-Alexa680-3'

(19 mer)
```

FIG. 29 shows the results.

MT(R3→RC, R4→RC, R5→RC) and MT(R3→RC2, R4→RC2, R5→RC2) may have binding force weaker than that of MT(R3→R5, R4→R5).

Example 3: Extension of Recognition Repeats

Example 3-1

Vector cloning and protein expression and purification were performed as in Example 2-5.

Gel shift assay was performed by the same procedures as in Example 1.

The following RNA probes were used.

```
OTS-1511:
                                   (SEQ ID NO: 30)
5'-Alexa680-CCAGAAUUGUAUAUAUUCG-Alexa680-3'

(19 mer) (probe for the wild type)

OTS-1844:
                                   (SEQ ID NO: 35)
5'-Alexa680-CCAGAAUUGUAUAUAUAUUCG-Alexa680-3'

(21 mer) (probe for hPUF_MT(1-2-5-6-5-6-5-6-7-8))
```

FIG. 30 shows the results. It is understood that MT(1-2-5-6-5-6-5-6-7-8) has binding force about 10 times greater than that of WT.

Example 3-2

(1) Vector Cloning

FIG. 31 shows the amino acid sequence of hPUF_MT(1-2-5-6-5-6-5-6-5-6-7-8).

Vector cloning was performed by the same procedures as in Example 2-1.

(2) Protein Expression and Purification

Protein expression and purification of hPUF_MT(1-2-5-6-5-6-5-6-5-6-7-8) were performed by the same procedures as in Example 1.

Note that protein expression was induced in a 1 mM IPTG-containing LB-Kan medium at 37° C. for 3 h.

Rotoring for absorption to the resin was carried out for 12.5 h.

(3) Gel Shift Assay

Gel shift assay was performed by the same procedures as in Example 1.

The following RNA probes were used.

```
OTS-1511:
                                   (SEQ ID NO: 30)
5'-Alexa680-CCAGAAUUGUAUAUAUUCG-Alexa680-3'

(19 mer) (probe for the wild type)

OTS-1844:
                                   (SEQ ID NO: 35)
5'-Alexa680-CCAGAAUUGUAUAUAUAUUCG-Alexa680-3'

(21 mer) (probe for hPUF_MT(1-2-5-6-5-6-5-6-7-8))

OTS-1924:
                                   (SEQ ID NO: 37)
5'-Alexa680-CCAGAAUUGUAUAUAUAUAUUCG-Alexa680-3'

(23 mer) (probe for hPUF_MT(1-2-5-6-5-6-5-6-5-6-7-8))
```

FIG. 32 shows the results. It is understood that MT(1-2-5-6-5-6-5-6-5-6-7-8) and MT(1-2-5-6-5-6-5-6-5-6-7-8) have binding ability greater than that of MT(R3→R5, R4→R6).

Example 3-3

(1) Vector Cloning

FIGS. 33 and 34 show the amino acid sequences of hPUF_MT(1-2-5-6-5-6-5-6-5-6-5-6-7-8) and hPUF_MT(1-2-5-6-5-6-5-6-5-6-5-6-7-8).

(2) Protein Expression and Purification

Protein expression and purification were performed by the same procedures as in Example 1.

Note that protein expression induction was carried out under the following conditions.

hPUF_MT(1-2-5-6-5-6-5-6-5-6-5-6-7-8): 37° C. for 3 h in a 1 mM IPTG-containing LB-Kan medium hPUF_MT(1-2-5-6-5-6-5-6-5-6-5-6-7-8): 37° C. for 3 h in a 1 mM IPTG-containing LB-Kan medium Rotoring for absorption to the resin was carried out for 16 h.

(3) Gel Shift Assay

Gel shift assay was performed by the same procedures as in Example 1.

The following RNA probes were used.

```
OTS-1844:
                                           (SEQ ID NO: 35)
5'-Alexa680-CCAGAAUUGUAUAUAUAUUCG-Alexa680-3'

(21 mer) (probe for hPUF_MT(1-2-5-6-5-6-5-6-7-8))

OTS-1925:
                                           (SEQ ID NO: 38)
5'-Alexa680-CCAGAAUUGUAUAUAUAUAUAUUCG-Alexa680-3'

(25 mer) (probe for hPUF_MT(1-2-5-6-5-6-5-6-5-

6-7-8))

OTS-1926:
                                           (SEQ ID NO: 39)
5'-Alexa680-CCAGAAUUGUAUAUAUAUAUAUAUUCG- Alexa680-3' (27 mer) (probe for hPUF_MT(1-2-5-6-5-

6-5-6-5-6-5-6-7-8))
```

FIG. 35 shows the results.

Example 4: Alteration of Recognition Specificity

Example 4-1

(1) Vector Cloning

FIGS. 36 and 37 show the amino acid sequences of hPUF_MT(R3→R5, R4→R5), hPUF_MT(R3→R5_C12N, R4→R5_C12N, R5_C12N), hPUF_MT(R3R5_C12S, Q16E, R4→R5_C12S, Q16E, R5_C12S, Q16E), and hPUF_MT(R3→R5_C12S, Q16R, R4→R5_C12S, Q16R, R5_C12S, Q16R).

Vector cloning was performed by the same procedures as in Example 2-1.

(2) Protein Expression and Purification hPUF_MT(R3→R5, R4→R5) is as described above.

Protein expression and purification of hPUF_MT (R3→R5_C12N, R4→R5_C12N, R5_C12N), hPUF_MT (R3→R5_C12S, Q16E, R4→R5_C12S, Q16E, R5_C12S, Q16E), and hPUF_MT(R3→R5_C12S, Q16R, R4→R5_C12S, Q16R, R5_C12S, Q16R) were performed by the same procedures as in Example 1. Note that protein expression induction was carried out under the following conditions.

hPUF_MT(R3→R5_C12N, R4→R5_C12N, R5_C12N): 37° C. for 3 h in a 1 mM IPTG-containing LB-Kan medium hPUF_MT(R3→R5_C12S, Q16E, R4→R5_C12N, Q16E, R5_C12S, Q16E): 37° C. for 3 h in a 0.01 mM IPTG-containing LB-Kan medium hPUF_MT(R3→R5_C12S, Q16R, R4→R5_C12N, Q16R, R5_C12S, Q16R): 20° C. for 24 h in a 1 mM IPTG-containing LB-Kan medium Rotoring for absorption to the resin was carried out for 12.5 h.

(3) Gel Shift Assay

Gel shift assay was performed by the same procedures as in Example 1.

The following RNA probe was used.

```
OTS-1511:
                                           (SEQ ID NO: 30)
5'-Alexa680-CCAGAAUUGUAUAUAUUCG-Alexa680-3'

(19 mer) (wild-type sequence)

OTS-1841:
                                           (SEQ ID NO: 40)
5'-Alexa680-CCAGAAUUGUUUUUAUUCG-Alexa680-3'

(19 mer) (A→U sequence)

OTS-1842:
                                           (SEQ ID NO: 41)
5'-Alexa680-CCAGAAUUGUGGGUAUUCG-Alexa680-3'

(19 mer) (A→G sequence)

OTS-1843:
                                           (SEQ ID NO: 42)
5'-Alexa680-CCAGAAUUGUCCCUAUUCG-Alexa680-3'

(19 mer) (A→C sequence)
```

FIG. 38 shows the results. C12N·C12S, Q16E·C12S, and Q16R were found to have binding ability greater than that of MT(R3→R5, R4→R5). It is understood that the degree of the binding force is in the following order: C12N (U recognition)>C12S, Q16E (G recognition)>C12S, Q16R (C recognition)>MT (R3→R5, R4→R5) (A recognition).

Example 4-2

The same protein as in Example 4-1 was used.
Gel shift assay was performed by the same procedures as in Example 1.
The following RNA probes were used.

```
OTS-1511:
                                           (SEQ ID NO: 30)
5'-Alexa680-CCAGAAUUGUAUAUAUUCG-Alexa680-3'

(19 mer) (wild-type sequence)

OTS-1841:
                                           (SEQ ID NO: 40)
5'-Alexa680-CCAGAAUUGUUUUUAUUCG-Alexa680-3'

(19 mer) (A→U sequence)

OTS-1842:
                                           (SEQ ID NO: 41)
5'-Alexa680-CCAGAAUUGUGGGUAUUCG-Alexa680-3'

(19 mer) (A→G sequence)

OTS-1843:
                                           (SEQ ID NO: 42)
5'-Alexa680-CCAGAAUUGUCCCUAUUCG-Alexa680-3'

(19 mer) (A→C sequence)
```

FIG. 39 shows the results. Each protein binds only to its target sequence and may have specificity.

Example 4-3

(1) Vector Cloning

FIGS. 40 and 41 show the amino acid sequences of hPUF_MT(R4→R6), hPUF_MT(R4→R6_N12C, R6_N12C), hPUF_MT(R4→R6_N12S, Q16E, R6_N12S, Q16E), and hPUF_MT(R4→R6_N12S, Q16R, R6_N12S, Q16R).

Vector cloning was performed by the same procedures as in Example 2-1.

(2) Protein Expression and Purification hPUF_MT(R4→R6) is as described above.

Protein expression and purification of hPUF_MT (R4→R6_N12C, R6_N12C), hPUF_MT(R4→R6_N12S, Q16E, R6_N12S, Q16E), and hPUF_MT(R4→R6_N12S, Q16R, R6_N12S, Q16R) were performed by the same procedures as in Example 1. Note that protein expression induction was carried out under the following conditions.

hPUF_MT(R4→R6_N12C, R6_N12C): 30° C. for 7 h in a 0.1 mM IPTG-containing LB-Kan medium hPUF_MT(R4→R6_N12S, Q16E, R6_N12S, Q16E): 25° C. for 22 h in a 0.1 mM IPTG-containing LB-Kan medium hPUF_MT(R4→R6_N12S, Q16R, R6_N12S, Q16R): 30° C. for 7 h in a 0.1 mM IPTG-containing LB-Kan medium Rotoring for absorption to the resin was carried out for 12 h.

(3) Gel Shift Assay

Gel shift assay was performed by the same procedures as in Example 1.

The following RNA probes were used.

```
OTS-1511:
                                    (SEQ ID NO: 30)
5'-Alexa680-CCAGAAUUGUAUAUAUUCG-Alexa680-3'

(19 mer) (wild-type sequence)

OTS-1819:
                                    (SEQ ID NO: 43)
5'-Alexa680-CCAGAAUUGAAAAUAUUCG-Alexa680-3'

(19 mer) (U→A sequence)

OTS-1978:
                                    (SEQ ID NO: 44)
5'-Alexa680-CCAGAAUUGGAGAUAUUCG-Alexa680-3'

(19 mer) (U→G sequence)

OTS-1979:
                                    (SEQ ID NO: 45)
5'-Alexa680-CCAGAAUUGCACAUAUUCG-Alexa680-3'

(19 mer) (U→C sequence)
```

FIG. 42 shows the results. In the cases of G recognition and C recognition, binding force was almost comparable to or relatively weaker than that of the wild type in the case of U recognition. In the case of A recognition, binding force significantly declined (to about 1/100).

Example 4-4

The same proteins as in Example 4-3 were used.

Gel shift assay was performed by the same procedures as in Example 1. The following RNA probes were used.

```
OTS-1511:
                                    (SEQ ID NO: 30)
5'-Alexa680-CCAGAAUUGUAUAUAUUCG-Alexa680-3'

(19 mer) (wild-type sequence)

OTS-1819:
                                    (SEQ ID NO: 43)
5'-Alexa680-CCAGAAUUGAAAAUAUUCG-Alexa680-3'

(19 mer) (U→A sequence)

OTS-1978:
                                    (SEQ ID NO: 44)
5'-Alexa680-CCAGAAUUGGAGAUAUUCG-Alexa680-3'

(19 mer) (U→G sequence)

OTS-1979:
                                    (SEQ ID NO: 45)
5'-Alexa680-CCAGAAUUGCACAUAUUCG-Alexa680-3'

(19 mer) (U→C sequence)
```

FIG. 43 shows the results. The results were the same as in Example 4-3 (reproducibility was confirmed).

Example 5: Optimization of Stacking Amino Acids

Example 5-1

(1) Vector Cloning

FIGS. 44 and 45 show the amino acid sequences of hPUF_MT(R5_R13K), hPUF_MT(R6_Y13F), hPUF_MT (R6_Y13H), and hPUF_MT(R6_Y13W).

Vector cloning was performed by the same procedures as in Example 2-1.

(2) Protein Expression and Purification

Protein expression and purification were performed by the same procedures as in Example 1.

Note that protein expression induction was carried out under the following conditions.

hPUF_MT(R5_13K): 37° C. for 3 h in a 0.1 mM IPTG-containing LB-Kan medium hPUF_MT(R6_13F): 37° C. for 3 h in a 0.1 mM IPTG-containing LB-Kan medium hPUF_MT(R6_13H): 37° C. for 3 h in a 0.1 mM IPTG-containing LB-Kan medium hPUF_MT(R6_13W): 37° C. for 3 h in a 0.1 mM IPTG-containing LB-Kan medium Rotoring for absorption to the resin was carried out for 8 h.

(2) Gel Shift Assay

Gel shift assay was performed by the same procedures as in Example 1.

The following RNA probe was used.

```
OTS-1511:
                                    (SEQ ID NO: 30)
5'-Alexa680-CCAGAAUUGUAUAUAUUCG-Alexa680-3'

(19 mer)
```

FIG. 46 shows the results. Arg was the optimal amino acid as a cationic amino acid between A and U (A-U), and Tyr was the optimal amino acid as an aromatic amino acid between U and A (U-A).

Example 5-2

(1) Vector Cloning

FIGS. 47 to 49 show the amino acid sequences of hPUF_MT(R3→R4→R5), hPUF_MT(R3→R5, R4→R5→R13H, R5→R13H), hPUF_MT(R3→R5, R4→R5→R13Y, R5→R13Y), hPUF_MT(R3→R5, R4→R5→R13Y, R5→R13Y), and hPUF_MT(R3→R5, R4→R5→R13W, R5→R13W).

Vector cloning was performed by the same procedures as in Example 2-1.

(2) Protein Expression and Purification hPUF_MT(R3→R5, R4→R5) is as described above. Protein expression and purification of hPUF_MT(R3→R5, R4→R5→R13H, R5→R13H), hPUF_MT(R3→R5, R4→R5→R13Y, R5→R13Y), hPUF_MT(R3→R4→R5→R13Y, R5→R13Y), and hPUF_MT(R3→R4→R5→R13W, R5→R13W) were performed by the same procedures as in Example 1. Note that protein expression was induced in a 1 mM IPTG-containing LB-Kan medium at 37° C. for 3 h.

Rotoring for absorption to the resin was carried out for 3 h.

(3) Gel Shift Assay

Gel shift assay was performed by the same procedures as in Example 1.
The following RNA probe was used.

```
OTS-1759:
                                        (SEQ ID NO: 31)
5'-Alexa680-CCAGAAUUGUAAAUAUUCG-Alexa680-3'

(19 mer)
```

FIG. 50 shows the results. The degree of binding force of a stacking amino acid between A and A (A-A) appears to be Trp>Tyr>>Phe>His.

Example 5-3

(1) Vector Cloning

FIG. 51 shows the amino acid sequence of hPUF_MT (R3→R5, R4→R5→R13K, R5→R13K).

Vector cloning was performed by the same procedures as in Example 2-1.

(2) Protein Expression and Purification

Protein expression and purification were performed by the same procedures as in Example 1.

Note that protein expression was induced in a 0.1 mM IPTG-containing LB-Kan medium at 30° C. for 7 h.

Rotoring for absorption to the resin was carried out for 16 h.

(3) Gel Shift Assay

Gel shift assay was performed by the same procedures as in Example 1.
The following RNA probe was used.

```
OTS-1759:
                                        (SEQ ID NO: 31)
5'-Alexa680-CCAGAAUUGUAAAUAUUCG-Alexa680-3'

(19 mer)
```

FIG. 52 shows the results. As the A-A stacking amino acid, aromatic amino acids have stronger binding force than cationic amino acids. Among aromatic amino acids, His and Tyr have high levels of binding force.

Example 5-4

(1) Vector Cloning

FIGS. 53 and 54 show the amino acid sequences of hPUF_MT(R5:A_13R)$_3$(R6:C_13Y)$_3$, hPUF_MT(R5:A_13R)$_3$(R6:C_13R)$_3$, and hPUF_MT(R5:A_13R)(R5:A_13Y)$_2$(R6:C_13Y)$_3$.

Vector cloning was performed by the same procedures as in Example 2-1.

(2) Protein Expression and Purification

Gel shift assay was performed by the same procedures as in Example 1.

Rotoring for absorption to the resin was carried out for 11 h.

(3) Gel Shift Assay

Gel shift assay was performed by the same procedures as in Example 1.
The following RNA probe was used.

```
OTS-2004:
                                        (SEQ ID NO: 46)
5'-Alexa680-CCAGAAUUGCACACAUAUUCG-Alexa680-3'

(21 mer)
```

FIG. 55 shows the results.

When comparing circled numbers 1 and 2, the circled number 1 has about three times greater binding force (Tyr>Arg).

When comparing circled numbers 1 and 3, the circled number 1 has about ten times greater binding force (Arg>Tyr).

Tyr is an appropriate aromatic amino acid between C and A (C-A), and Arg is an appropriate cationic amino acid between A and C (A-C).

Example 5-5

(1) Vector cloning

FIGS. 56 and 57 show the amino acid sequences of hPUF_MT(R5:A_13R)$_3$(R6:G_13Y)$_3$, hPUF_MT(R5:A_13R)$_3$(R6:G_13R)$_3$, and hPUF_MT(R5:A_13R)(R5:A_13Y)$_2$(R6:G_13Y)$_3$.

Vector cloning was performed by the same procedures as in Example 2-1.

(2) Protein Expression and Purification

Protein expression and purification were performed by the same procedures as in Example 1.

Rotoring for absorption to the resin was carried out for 11 h.

(3) Gel Shift Assay

Gel shift assay was performed by the same procedures as in Example 1.
The following RNA probe was used.

```
OTS-2008:
                                        (SEQ ID NO: 30)
5'-Alexa680-CCAGAAUUGGAGAGAUAUUCG-Alexa680-3'

(21 mer)
```

FIG. 58 shows the results.

When comparing circled numbers 1 and 2, the circled number 1 has at least 30 times greater binding force (Tyr>Arg).

Tyr is an appropriate aromatic amino acid between G and A (G-A).

When comparing circled numbers 1 and 3, the circled number 1 has slightly greater binding force (Arg>Tyr). Arg is an appropriate cationic amino acid between A and G (A-G).

Example 5-6

(1) Vector Cloning

FIGS. 59 and 60 show the amino acid sequences of hPUF_MT(R5:G_13R)$_3$(R6:U_13Y)$_3$, hPUF_MT(R5:G_13R)$_3$(R6:U_13R)$_3$, and hPUF_MT(R5:A_13R)(R5:A_13Y)$_2$(R6:G_13Y)$_3$.

Vector cloning was performed by the same procedures as in Example 2-1.

(2) Protein Expression and Purification

Gel shift assay was performed by the same procedures as in Example 1.

Rotoring for absorption to the resin was carried out for 11 h.

(3) Gel Shift Assay

Gel shift assay was performed by the same procedures as in Example 1.

The following RNA probe was used.

```
OTS-2004:
                                       (SEQ ID NO: 46)
5'-Alexa680-CCAGAAUUGUGUGUGUAUUCG-Alexa680-3'

(21 mer)
```

FIG. 61 shows the results. When comparing circled numbers 1 and 2, the circled number 2 has about 3 times greater binding force (Tyr>Arg). When comparing circled numbers 1 and 3, the circled number 1 has about 30 times greater binding force (Arg>Tyr). Arg is an appropriate cationic amino acid between U and G (U-G), and Arg is also an appropriate cationic amino acid between G and U (G-U).

Example 6: Comparison with Pumby (1) Vector Cloning

FIGS. 62 and 63 show the amino acid sequences of hPUF_MT(5_(6)8), MT(6_(56)4), and MT(4_(56)4).

Total synthesis of genes encoding hPUF_MT(5_(6)8), MT(6_(56)4), and MT(4_(56)4) was carried out. Synthesized genes were cleaved with EcoRI and HindIII and ligated with pET24-R1'-MSC—R8' which was also cleaved with EcoRI and HindIII, thereby constructing expression vectors. R1' and R8' were removed from the constructed expression vectors.

(2) Protein Expression and Purification

Gel shift assay was performed by the same procedures as in Example 1. Note that protein expression was induced in a 1 mM IPTG-containing LB-Kan medium at 37° C. for 3 h.

hPUF_MT(5_(5)$_8$): 20° C. for 21 h in a 0.1 mM IPTG-containing LB-Kan medium hPUF_MT(6_(56)$_4$): 37° C. for 3 h in a 0.1 mM IPTG-containing LB-Kan medium hPUF_MT(4 (56)$_4$): 37° C. for 3 h in a 0.1 mM IPTG-containing LB-Kan medium Rotoring for absorption to the resin was carried out for 11 h.

(3) Gel Shift Assay

Gel shift assay was performed by the same procedures as in Example 1.

The following RNA probe was used.

```
OTS-1511:
                                       (SEQ ID NO: 30)
5'-Alexa680-CCAGAAUUGUAUAUAUUCG-Alexa680-3'

(19 mer)
```

FIG. 64 shows the results.

Example 7: Extension of Recognition Repeats [2]

Example 7-1

(1) Vector Cloning

FIGS. 65 to 67 show the amino acid sequences of hPUF_MT(1-2-6-5-6-5-6-7-8), hPUF_MT(1-2-5-5-6-5-6-7-8), and hPUF_MT(1-2-5-6-5-6-6-7-8).

Vector cloning was performed by the same procedures as in Example 2-1.

(2) Protein Expression and Purification

Protein expression and purification were performed by the same procedures as in Example 1.

(3) Gel Shift Assay

Gel shift assay was performed by the same procedures as in Example 1.

FIG. 68 shows the results. The proteins having extended recognition repeats were found to have binding ability about three times greater than that of WT. The proteins having extended recognition repeats (circled numbers 2 to 4 of 9 repeats in FIG. 67) each had almost the same binding ability.

Example 7-2

(1) Vector Cloning

FIGS. 69 to 71 show the amino acid sequences of hPUF_MT(1-2-6-5-6-5-6-7-8), hPUF_MT(1-2-5-5-6-5-6-7-8), and hPUF_MT(1-2-5-6-5-6-6-7-8).

Vector cloning was performed by the same procedures as in Example 2-1.

(2) Protein Expression and Purification

Protein expression and purification were performed by the same procedures as in Example 7-1.

Note that protein expression of hPUF_MT(1-2-6-5-6-5-6-7-8) was induced in a 0.1 mM IPTG-containing LB-Kan medium at 37° C. for 3 h. Rotoring for absorption to the resin was carried out for 10 h. Protein expression of hPUF_MT(1-2-5-5-6-5-6-7-8) was induced in a 1 mM IPTG-containing LB-Kan medium at 37° C. for 3 h. Rotoring for absorption to the resin was carried out for 10 h. Protein expression of hPUF_MT(1-2-5-6-5-6-6-7-8) was induced in a 0.1 mM IPTG-containing LB-Kan medium at 37° C. for 3 h. Rotoring for absorption to the resin was carried out for 10 h.

(3) Gel Shift Assay

Gel shift assay was performed by the same procedures as in Example 7-1.

Note that the following RNA probes were used.

```
OTS-1511:
                                       (SEQ ID NO: 30)
5'-Alexa680-CCAGAAUUGUAUAUAUUCG-Alexa680-3'

(19 mer) (wild-type sequence)

OTS-2080:
                                       (SEQ ID NO: 48)
5'-Alexa680-CCAGAAUUGUAUAUUAUUCG-Alexa680-3'

(20 mer) (9 repeats (2))
```

```
                               -continued
OTS-2081:
                                              (SEQ ID NO: 49)
5'-Alexa680-CCAGAAUUGUAUAAUAUUCG-Alexa680-3'

(20 mer) (9 repeats (3))

OTS-2082:
                                              (SEQ ID NO: 50)
5'-Alexa680-CCAGAAUUGUUAUAUAUUCG-Alexa680-3'

(20 mer) (9 repeats (4))
```

FIG. 72 shows the results. The protein having 13 repeats was found to have the highest binding ability. The protein having 11 repeats was found to have the second highest binding ability, which was about three times greater than that of WT. The protein having 15 repeats was found to have binding ability slightly greater than that of WT.

Example 8: Alteration of Recognition Specificity [2]

Example 8-1

(1) Vector Cloning

FIGS. 73 to 76 show the amino acid sequences of hPUF_MT(R3→R5, R4→R6), hPUF_MT(R1_S12N, R3→R5, R4→R6), hPUF_MT(R1_Q16E, R3→R5, R4→R6), and hPUF_MT(R1_Q16R, R3→R4→R6).

Vector cloning was performed by the same procedures as in Example 2-1.

(2) Protein Expression and Purification

Protein expression and purification were performed by the same procedures as in Example 1.

Note that the expression of each protein was induced under the following conditions.

hPUF_MT(R1_S12N, R3→R5, R4→R6): 30° C. for 7 h in a 0.001 mM IPTG-containing LB-Kan medium hPUF_MT(R1_Q16E, R3→R5, R4→R6): 30° C. for 7 h in a 0.1 mM IPTG-containing LB-Kan medium hPUF_MT(R1_Q16R, R3→R5, R4→R6): 30° C. for 7 h in a 0.1 mM IPTG-containing LB-Kan medium Rotoring for absorption to the resin was carried out for 14 h.

(3) Gel Shift Assay

Gel shift assay was performed by the same procedures as in Example 1.

Note that the following RNA probes were used.

```
OTS-1511:
                                              (SEQ ID NO: 30)
5'-Alexa680-CCAGAAUUGUAUAUAUUCG-Alexa680-3'

(19 mer) (wild-type sequence)

OTS-2022:
                                              (SEQ ID NO: 51)
5'-Alexa680-CCAGAAUUGUAUAUUUUCG-Alexa680-3'

(19 mer) (A→U sequence)

OTS-2020:
                                              (SEQ ID NO: 52)
5'-Alexa680-CCAGAAUUGUAUAUGUUCG-Alexa680-3'

(19 mer) (A→G sequence)

OTS-2021:
                                              (SEQ ID NO: 53)
5'-Alexa680-CCAGAAUUGUAUAUCUUCG-Alexa680-3'

(19 mer) (A→C sequence)
```

The results are as shown in FIG. 77. As is understood from the figures, the proteins having extended recognition repeats were found to have binding ability about three times greater than that of WT. The results confirmed that the degree of the binding force is in the following order: Q16R (C recognition)>Q16E (G recognition)=MT(R3→R4→R5) (A recognition)>S12N (U recognition).

Further, the results of recognition specificity (FIG. 78) confirmed specificity as described below.

(1) MT(R3→R5, R4→R5): The degree of the binding force is in the order of U=C>A>G.

(2) MT(R1_S12N,R3→R5, R4→R5) (U recognition): The degree of the binding force is in the order of U>C>>G=A.

(3) MT(R1_Q16E,R3→R5, R4→R5) (G recognition): The degree of the binding force is in the order of G>>U=C.

(3) MT(R1_Q16E,R3→R5, R4→R5) (C recognition): The degree of the binding force is in the order of C>U>>G>A.

Note that the number in each pair of parentheses corresponds to the relevant circled number in the figures.

Example 8-2

(1) Vector Cloning

FIG. 79 shows the amino acid sequence of hPUF_MT (R3→R4→R6) (=novel backbone).

Vector cloning was performed by the same procedures as in Example 2-1.

(2) Protein Expression and Purification

Protein expression and purification were performed by the same procedures as in Example 8-1.

(3) Gel Shift Assay

Gel shift assay was performed by the same procedures as in Example 8-1.

Note that the following RNA probes were used.

```
OTS-1511:
                                              (SEQ ID NO: 30)
5'-Alexa680-CCAGAAUUGUAUAUAUUCG-Alexa680-3'

(19 mer) (wild-type sequence)

OTS-2022:
                                              (SEQ ID NO: 51)
5'-Alexa680-CCAGAAUUGUAUAUUUUCG-Alexa680-3'

(19 mer) (A→U sequence)

OTS-2020:
                                              (SEQ ID NO: 52)
5'-Alexa680-CCAGAAUUGUAUAUGUUCG-Alexa680-3'

(19 mer) (A→G sequence)

OTS-2021:
                                              (SEQ ID NO: 53)
5'-Alexa680-CCAGAAUUGUAUAUCUUCG-Alexa680-3'

(19 mer) (A→C sequence)
```

The results are as shown in FIG. 80. As is understood from the figure, since the wild type originally did not have base specificity, it was confirmed that the alteration of the skeleton was not the reason for the results.

In testing, the first and second samples of WT were tagged with MBP. The results indicating lack of specificity were obtained also for the wild type. In this regard, reproducibility of the novel backbone was confirmed for the third and fourth samples of WT.

Example 8-3

(1) Vector Cloning

FIGS. 81 to 85 show the amino acid sequences of hPUF_MT(R3→R5, R4→R6), hPUF_MT(R2_N12C, R3→R5, R4→R6), hPUF_MT(R2_N12S, R3→R5, R4→R6), hPUF_MT(R2_N12S, Q16E, R3→R5, R4→R6), and hPUF_MT(R2_N12S, Q16R, R3→R5, R4→R6).

Vector cloning was performed by the same procedures as in Example 2-1.

(2) Protein Expression and Purification

Protein expression and purification were performed by the same procedures as in Example 8-1.

Note that protein expression induction was carried out under the following conditions.

hPUF_MT(R2_N12C, R3→R5, R4→R6): 30° C. for 7 h in a 0.1 mM IPTG-containing LB-Kan medium hPUF_MT(R2_N12S, R3→R5, R4→R6): 30° C. for 7 h in a 0.1 mM IPTG-containing LB-Kan medium hPUF_MT(R2_N12S, Q16E, R3→R5, R4→R6): 30° C. for 7 h in a 0.1 mM IPTG-containing LB-Kan medium hPUF_MT(R2_N12S, Q16R, R3→R5, R4→R6): 30° C. for 7 h in a 0.1 mM IPTG-containing LB-Kan medium Rotoring for absorption to the resin was carried out for 12.5 h.

(3) Gel Shift Assay

Gel shift assay was performed by the same procedures as in Example 8-1.

Note that the following RNA probes were used.

```
OTS-1511:
                                       (SEQ ID NO: 30)
5'-Alexa680-CCAGAAUUGUAUAUAUUCG-Alexa680-3'

(19 mer) (wild-type sequence)

OTS-2023:
                                       (SEQ ID NO: 54)
5'-Alexa680-CCAGAAUUGUAUAAAUUCG-Alexa680-3'

(19 mer) (U→A sequence)

OTS-2024:
                                       (SEQ ID NO: 55)
5'-Alexa680-CCAGAAUUGUAUAGAUUCG-Alexa680-3'

(19 mer) (U→G sequence)

OTS-2025:
                                       (SEQ ID NO: 56)
5'-Alexa680-CCAGAAUUGUAUACAUUCG-Alexa680-3'

(19 mer) (U→C sequence)
```

The results are as shown in FIG. 86. As is understood from the figure, the results confirmed that the binding proteins having the above amino acid sequences which were prepared as above did not have binding ability greater than that of MT(R3→R5, R4→R5) (left side on the figure) which were prepared as described earlier. The results confirmed that the degree of the binding force is in the following order: MT(R3→R5, R4→R5) (U recognition)>N12S, Q16E (G recognition)>N12S, Q16R (C recognition)>S12C (U recognition).

Example 8-4

(1) Vector Cloning

FIGS. 87 to 90 show the amino acid sequences of hPUF_MT(R3→R5, R4→R6), hPUF_MT(R2_N12C, R3→R5, R4→R6), hPUF_MT(R2_N12S, Q16E, R3→R5, R4→R6), and hPUF_MT(R2_N12S, Q16R, R3→R5, R4→R6).

Vector cloning was performed by the same procedures as in Example 2-1.

(2) Protein Expression and Purification

Protein expression and purification were performed by the same procedures as in Example 8-1.

Note that protein expression induction was carried out under the following conditions.

hPUF_MT(R2_N12C, R3→R5, R4→R6): 30° C. for 7 h in a 0.1 mM IPTG-containing LB-Kan medium hPUF_MT(R2_N12S, Q16E, R3→R5, R4→R6): 30° C. for 7 h in a 0.1 mM IPTG-containing LB-Kan medium hPUF_MT(R2_N12S, Q16R, R3→R5, R4→R6): 30° C. for 7 h in a 0.1 mM IPTG-containing LB-Kan medium Rotoring for absorption to the resin was carried out for 12.5 h.

(3) Gel Shift Assay

Gel shift assay was performed by the same procedures as in Example 8-1.

Note that the following RNA probes were used.

```
OTS-1511:
                                       (SEQ ID NO: 30)
5'-Alexa680-CCAGAAUUGUAUAUAUUCG-Alexa680-3'

(19 mer) (wild-type sequence)

OTS-2023:
                                       (SEQ ID NO: 54)
5'-Alexa680-CCAGAAUUGUAUAAAUUCG-Alexa680-3'

(19 mer) (U→A sequence)

OTS-2024:
                                       (SEQ ID NO: 55)
5'-Alexa680-CCAGAAUUGUAUAGAUUCG-Alexa680-3'

(19 mer) (U→G sequence)

OTS-2025:
                                       (SEQ ID NO: 56)
5'-Alexa680-CCAGAAUUGUAUACAUUCG-Alexa680-3'

(19 mer) (U→C sequence)
```

The results are as shown in FIG. 91. As is understood from the figure, the following were indicated.
(1) MT(R3→R5, R4→R5): The degree of the binding force is in the order of U>>C.
(2) MT(R2_S12C, R3→R5, R4→R5) (A recognition): The degree of the binding force is in the order of A=U=C>>G.
(3) MT(R2_N12S, Q16E R3→R4→R5) (G recognition): Binding to G occurred exclusively.
(4) MT(R2_N12S, Q16R, R3→R4→R5) (C recognition): Binding to C occurred exclusively.

Circle numbers 1 to 4 in the figure correspond to (1) to (4) above.

Example 8-5

(1) Vector Cloning

FIGS. 92 to 96 show the amino acid sequences of hPUF_MT(R3→R5, R4→R6), hPUF_MT(R7_S12C,E16Q, R3→R5, R4→R6), hPUF_MT(R7_E16Q, R3→R5, R4→R6), hPUF_MT(R7_S12N,E16Q, R3→R4→R6), and hPUF_MT(R7_E16R, R3→R4→R6).

Vector cloning was performed by the same procedures as in Example 2-1.

(2) Protein Expression and Purification

Protein expression and purification were performed by the same procedures as in Example 8-1.

Note that protein expression induction was carried out under the following conditions.

hPUF_MT(R7_S12C, E16Q, R3→R5, R4→R6): 37° C. for 3 h in a 1 mM IPTG-containing LB-Kan medium hPUF_MT(R7_E16Q, R3→R5, R4→R6): 37° C. for 3 h in a 1 mM IPTG-containing LB-Kan medium hPUF_MT(R7_S12N, E16Q, R3→R5, R4→R6): 37° C. for 3 h in a 1 mM IPTG-containing LB-Kan medium hPUF_MT(R7_E16R, R3→R5, R4→R6): 37° C. for 3 h in a 1 mM IPTG-containing LB-Kan medium Rotoring for absorption to the resin was carried out for 3.5 h.

(3) Gel Shift Assay

Gel shift assay was performed by the same procedures as in Example 8-1.

Note that the following RNA probes were used.

```
OTS-1511:
                                        (SEQ ID NO: 30)
5'-Alexa680-CCAGAAUUGUAUAUAUUCG-Alexa680-3'

(19 mer) (wild-type sequence)

OTS-1754:
                                        (SEQ ID NO: 33)
5'-Alexa680-CCAGAAUUAUAUAUAUUCG-Alexa680-3'

(19 mer) (G→A sequence)

OTS-2032:
                                        (SEQ ID NO: 57)
5'-Alexa680-CCAGAAUUUUAUAUAUUCG-Alexa680-3'

(19 mer) (G→U sequence)

OTS-2033:
                                        (SEQ ID NO: 58)
5'-Alexa680-CCAGAAUUCUAUAUAUUCG-Alexa680-3'

(19 mer) (G→C sequence)
```

The results are as shown in FIG. 97. As is understood from the figure, the following were indicated.

The binding proteins having the above amino acid sequences which were prepared as above did not have binding ability greater than that of MT(R3→R5, R4→R5).

The results confirmed that the degree of the binding force is in the following order: MT(R3→R5, R4→R5 (G recognition)>MT(R3→R5, R4→R5, R7_S12N, E16Q) (U recognition)>MT(R3→R5, R4→R5, R7_E16R) (C recognition) >MT(R3→R5, R4→R5, R7_S12C, E16Q (A_E16Q)>MT (R3→R5, R4→R5, R7_S12C, E16Q) (A_S12C, E16Q).

Example 8-6

(1) Vector Cloning

FIGS. 98 to 101 show the amino acid sequences of hPUF_MT(R3→R4→R6), hPUF_MT(R7_S12C,E16Q, R3→R5, R4→R6), hPUF_MT(R7_S12N,E16Q, R3→R5, R4→R6), and hPUF_MT(R7_E16R, R3→R5, R4→R6).

Vector cloning was performed by the same procedures as in Example 2-1.

(2) Protein Expression and Purification

Protein expression and purification were performed by the same procedures as in Example 8-1.

Note that protein expression induction was carried out under the following conditions.

hPUF_MT(R7_S12C, E16Q, R3→R5, R4→R6): 37° C. for 3 h in a 1 mM IPTG-containing LB-Kan medium hPUF_MT(R7_S12N, E16Q, R3→R5, R4→R6): 37° C. for 3 h in a 1 mM IPTG-containing LB-Kan medium hPUF_MT(R7_E16R, R3→R5, R4→R6): 37° C. for 3 h in a 1 mM IPTG-containing LB-Kan medium Rotoring for absorption to the resin was carried out for 3.5 h.

(3) Gel Shift Assay

Gel shift assay was performed by the same procedures as in Example 8-1.

Note that the following RNA probes were used.

```
OTS-1511:
                                        (SEQ ID NO: 30)
5'-Alexa680-CCAGAAUUGUAUAUAUUCG-Alexa680-3'

(19 mer) (wild-type sequence)

OTS-1754:
                                        (SEQ ID NO: 33)
5'-Alexa680-CCAGAAUUAUAUAUAUUCG-Alexa680-3'

(19 mer) (G→A sequence)

OTS-2032:
                                        (SEQ ID NO: 57)
5'-Alexa680-CCAGAAUUUUAUAUAUUCG-Alexa680-3'

(19 mer) (G→U sequence)

OTS-2033:
                                        (SEQ ID NO: 58)
5'-Alexa680-CCAGAAUUCUAUAUAUUCG-Alexa680-3'

(19 mer) (G→C sequence)
```

The results are as shown in FIG. 102. As is understood from the figure, the following were indicated.

(1) MT(R3→R5, R4→R5): Binding to G occurred exclusively.

(2) MT(R3→R5, R4→R5, R7_S12C, E16Q) (A recognition): The degree of the binding force is in the order of U>C.

(3) MT(R3→R5, R4→R5, R7_S12N, E16Q) (U recognition): Binding to U occurred exclusively.

(4) MT(R3→R5, R4→R5, R7E16R) (C recognition): Binding to C and U occurred.

Note that the number in each pair of parentheses corresponds to the relevant circled number in the figure.

Example 8-7

(1) Vector Cloning

FIGS. 103 to 107 show the amino acid sequences of hPUF_MT(R3→R5, R4→R6), hPUF_MT(R8_N12C, R3→R5, R4→R6), hPUF_MT(R8_N12S, R3→R5, R4→R6), hPUF_MT(R8_N12S, Q16E, R3→R5, R4→R6), and hPUF_MT(R8_N12S, Q16R, R3→R5, R4 R6).

Vector cloning was performed by the same procedures as in Example 2-1.

(2) Protein Expression and Purification

Protein expression and purification were performed by the same procedures as in Example 8-1.

Note that protein expression induction was carried out under the following conditions.

hPUF_MT(R8_N12C, R3→R5, R4→R6): 37° C. for 3 h in a 0.01 mM IPTG-containing LB-Kan medium hPUF_MT(R8_N12S, R3→R5, R4→R6): 37° C. for 3 h in a 1 mM IPTG-containing LB-Kan medium hPUF_MT(R8_N12S, Q16E, R3→R5, R4→R6): 37° C. for 3 h in a 0.01 mM IPTG-containing LB-Kan medium hPUF_MT(R8_N12S, Q16R, R3→R5, R4→R6): 37° C. for 3 h in a 0.01 mM IPTG-containing LB-Kan medium Rotoring for absorption to the resin was carried out for 11 h.

(3) Gel Shift Assay

Gel shift assay was performed by the same procedures as in Example 8-1.

Note that the following RNA probes were used.

```
OTS-1511:
                                          (SEQ ID NO: 30)
5'-Alexa680-CCAGAAUUGUAUAUAUUCG-Alexa680-3'

(19 mer) (wild-type sequence)

OTS-1825:
                                          (SEQ ID NO: 36)
5'-Alexa680-CCAGAAUAGUAUAUAUUCG-Alexa680-3'

(19 mer) (U→A sequence)

OTS-2034:
                                          (SEQ ID NO: 59)
5'-Alexa680-CCAGAAUGGUAUAUAUUCG-Alexa680-3'

(19 mer) (U→G sequence)

OTS-2035:
                                          (SEQ ID NO: 60)
5'-Alexa680-CCAGAAUCGUAUAUAUUCG-Alexa680-3'

(19 mer) (U→C sequence)
```

The results are as shown in FIG. 108. As is understood from the figure, the following were indicated.

The binding proteins having the above amino acid sequences which were prepared as above did not have binding ability greater than that of MT(R3→R5, R4→R5). The results confirmed that the degree of the binding force is in the following order: MT(R3→R5, R4→R5) (U recognition)>N12S, Q16R (C recognition)>N12S, Q16E (G recognition). No binding was confirmed for S12C (A recognition) =N12S (A recognition).

Example 8-8

(1) Vector Cloning

FIGS. 109 to 112 show the amino acid sequences of hPUF_MT(R3→R5, R4→R6), hPUF_MT(R8_N12C, R3→R5, R4→R6), hPUF_MT(R8_N12S, Q16E, R3→R5, R4→R6), and hPUF_MT(R8_N12 S, Q16R, R3→R4→R6).

Vector cloning was performed by the same procedures as in Example 2-1.

(2) Protein Expression and Purification

Protein expression and purification were performed by the same procedures as in Example 8-1.

Note that protein expression induction was carried out under the following conditions.

hPUF_MT(R8_N12C, R3→R5, R4→R6): 37° C. for 3 h in a 0.01 mM IPTG-containing LB-Kan medium hPUF_MT(R8_N12S, Q16E, R3→R5, R4→R6): 37° C. for 3 h in a 0.01 mM IPTG-containing LB-Kan medium hPUF_MT(R8_N12S, Q16R, R3→R4→R6): 37° C., 3 h in a 0.01 mM IPTG-containing LB-Kan medium Rotoring for absorption to the resin was carried out for 11 h.

(3) Gel Shift Assay

Gel shift assay was performed by the same procedures as in Example 8-1.

Note that the following RNA probes were used.

```
OTS-1511:
                                          (SEQ ID NO: 30)
5'-Alexa680-CCAGAAUUGUAUAUAUUCG-Alexa680-3'

(19 mer) (wild-type sequence)

OTS-1825:
                                          (SEQ ID NO: 36)
5'-Alexa680-CCAGAAUAGUAUAUAUUCG-Alexa680-3'

(19 mer) (U→A sequence)

OTS-2034:
                                          (SEQ ID NO: 59)
5'-Alexa680-CCAGAAUGGUAUAUAUUCG-Alexa680-3'

(19 mer) (U→G sequence)

OTS-2035:
                                          (SEQ ID NO: 60)
5'-Alexa680-CCAGAAUCGUAUAUAUUCG-Alexa680-3'

(19 mer) (U→C sequence)
```

The results are as shown in FIG. 113. As is understood from the figure, the following were indicated.
(1) MT(R3→R5, R4→R5): Binding to U occurred exclusively.
(2) MT(R3→R5, R4→R5, R8_N12C) (A recognition): No binding occurred.
(3) MT(R3→R5, R4→R5, R8_N12S, Q16E) (G recognition): Binding to G occurred exclusively.
(4) MT(R1_Q16E, R3→R5, R4→R5) (C recognition): The degree of the binding force is in the order of C>>G>C.

Note that the number in each pair of parentheses corresponds to the relevant circled number in the figure.

Example 9: Optimization of Stacking Amino Acids [2]

The following 16 types of combinations can be considered for the optimization of the confirmed stacking amino acids. In this Example, experiments were conducted on the levels marked with "*" below to confirm the results.

Stacking between different bases (12 types)
Between A-C/Between C-A
Between A-U/Between U-A*
Between G-A/Between A-G
Between U-G/Between G-U
Between C-G/Between G-C*
Between U—C/Between C—U*
Stacking between the same bases (4 types)
Between A-A*
Between G-G*
Between U—U*
Between C—C*

<Verification of Stacking Amino Acids Regarding Stacking Between Different Bases (FIG. 114)>

Example 9-1: Between A-U/Between U-A (FIG. 115)

(1) Vector Cloning

FIGS. 116 to 118 show the amino acid sequences of hPUF_MT(R5:A_13R)$_3$(R6:U_13Y)$_3$, hPUF_MT(R5:A_13R)$_3$(R6:U_13R)$_3$, and hPUF_MT(R5:A_13R)(R5:A_13Y)$_2$(R6:U_13Y)$_3$.

Vector cloning was performed by the same procedures as in Example 2-1.

(2) Protein Expression and Purification

Protein expression and purification were performed by the same procedures as in Example 1.

Note that protein expression induction was carried out under the following conditions. hPUF_MT(R5:A_13R)$_3$ (R6:U_13Y)$_3$: 37° C. for 3 h in a 1 mM IPTG-containing LB-Kan medium Rotoring for absorption to the resin was carried out for 9.5 h.

hPUF_MT(R5:A_13R)$_3$(R6:U_13R)$_3$: 30° C. for 7 h in a 0.1 mM IPTG-containing LB-Kan medium hPUF_MT(R5:A_13R)(R5:A_13Y)$_2$(R6:U_13Y)$_3$: 37° C. for 3 h in a 1 mM IPTG-containing LB-Kan medium Rotoring for absorption to the resin was carried out for 8 h.

(3) Gel Shift Assay

Gel shift assay was performed by the same procedures as in Example 1.

Note that the following RNA probe was used.

```
OTS-1844:
                                    (SEQ ID NO: 35)
5'-Alexa680-CCAGAAUUGUAUAUAUAUUCG-Alexa680-3'

(21 mer)
```

FIG. 119 shows the results. A comparison of circled numbers 1 and 2 showed that the circled number 1 has at least 30 times greater binding force (Tyr>Arg). A comparison of circled numbers 1 and 3 showed that both the circled numbers 1 and 3 have the equivalent binding force (Arg=Tyr). It was found that there was no significant difference between U-A for Tyr as an aromatic amino acid, and there was no significant difference between A-U for Arg and Tyr.

Example 9-2: Between C-G/Between G-C (FIG. 120)

(1) Vector Cloning

FIGS. 121 to 123 show the amino acid sequences of hPUF_MT(R5:G_13R)$_3$(R6:C_13Y)$_3$, hPUF_MT(R5:G_13R)$_3$(R6:C_13R)$_3$, and hPUF_MT(R5:G_13R)(R5:G_13Y)$_2$(R6:C_13Y)$_3$.

Vector cloning was performed by the same procedures as in Example 2-1.

(2) Protein Expression and Purification

Protein expression and purification were performed by the same procedures as in Example 1.

Note that protein expression induction was carried out under the following conditions.

hPUF_MT(R5:G_13R)$_3$(R6:C_13Y)$_3$: 37° C. for 3 h in a 1 mM IPTG-containing LB-Kan medium hPUF_MT(R5:G_13R)$_3$(R6:C_13R)$_3$: 37° C. for 3 h in a 1 mM IPTG-containing LB-Kan medium hPUF_MT(R5:G_13R)(R5:G_13Y)$_2$(R6:C_13Y)$_3$: 37° C. for 3 h in a 1 mM IPTG-containing LB-Kan medium Rotoring for absorption to the resin was carried out for 12 h.

(3) Gel Shift Assay

Gel shift assay was performed by the same procedures as in Example 1.

Note that the following RNA probe was used.

```
OTS-2007:
                                    (SEQ ID NO: 61)
5'-Alexa680-CCAGAAUUGCGCGCGUAUUCG-Alexa680-3'

(24 mer)
```

FIG. 124 shows the results. A comparison of circled numbers 1 and 2 showed that the circled number 2 has slightly greater binding force (Tyr<Arg). A comparison of circled numbers 1 and 3 showed that the circled number 1 has slightly greater binding force (Arg>Tyr). It was found that Arg was a suitable cationic amino acid between C-G, and Arg was also a suitable cationic amino acid between G-C.

Example 9-3: Between U—C/Between C—U (FIG. 125)

(1) Vector Cloning

FIGS. 126 to 128 show the amino acid sequences of hPUF_MT(R5:C_13R)$_3$(R6:U_13Y)$_3$, hPUF_MT(R5:C_13R)$_3$(R6:U_13R)$_3$, and hPUF_MT(R5:C_13R)(R5:C_13Y)$_2$(R6:U_13Y)$_3$.

Vector cloning was performed by the same procedures as in Example 2-1.

(2) Protein Expression and Purification

Protein expression and purification were performed by the same procedures as in Example 1.

Note that protein expression induction was carried out under the following conditions.

hPUF_MT(R5:C_13R)$_3$(R6:U_13Y)$_3$: 37° C. for 3 h in a 0.1 mM IPTG-containing LB-Kan medium hPUF_MT(R5:C_13R)$_3$(R6:U_13R)$_3$: 37° C. for 3 h in a 0.1 mM IPTG-containing LB-Kan medium hPUF_MT(R5:C_13R)(R5:C_13Y)$_2$(R6:U_13Y)$_3$: 37° C. for 3 h in a 0.1 mM IPTG-containing LB-Kan medium Rotoring for absorption to the resin was carried out for 13.5 h.

(3) Gel Shift Assay

Gel shift assay was performed by the same procedures as in Example 1.

Note that the following RNA probe was used.

```
OTS-2006:
                                    (SEQ ID NO: 62)
5'-Alexa680-CCAGAAUUGUCUCUCUAUUCG-Alexa680-3'

(21 mer)
```

FIG. 129 shows the results. A comparison of circled numbers 1 and 2 showed that the circled number 1 has about 10 times greater binding force (Tyr>Arg). A comparison of circled numbers 1 and 3 showed that the circled number 3 has slightly greater binding force (Arg<Tyr). In other words, Tyr was an appropriate aromatic amino acid between U—C, and Tyr is was also an appropriate aromatic amino acid between C—U.

<Verification of Stacking Amino Acids Regarding Stacking Between the Same Bases (FIG. 130)>

Example 9-4: Between A-A (FIG. 131)

(1) Vector Cloning

FIGS. 132 to 137 show the amino acid sequences of hPUF_MT(R3→R5, R4→R5), hPUF_MT(R3→R5, R4→R5→R13K, R5→R13K), hPUF_MT(R3→R5, R4→R5→R13F, R5→R13F), hPUF_MT(R3→R5, R4→R5→R13H, R5→R13H), hPUF_MT(R3→R5, R4→R5→R13W, R5→R13W), and hPUF_MT(R3→R5, R4→R5→R13Y, R5→R13Y).

Vector cloning was performed by the same procedures as in Example 2-1.

(2) Protein Expression and Purification

Protein expression and purification were performed by the same procedures as in Example 1.

Note that protein expression induction was carried out under the following conditions. hPUF_MT(R3→R5, R4→R5): 30° C. for 7 h in a 0.01 mM IPTG-containing LB-Kan medium Rotoring for absorption to the resin was carried out for 10 h.

hPUF_MT(R3→R5, R4→R5→R13K, R5→R13K): 30° C. for 7 h in a 0.1 mM IPTG-containing LB-Kan medium Rotoring for absorption to the resin was carried out for 16 h.

hPUF_MT(R3→R5, R4→R5→R13F, R5→R13F): 37° C. for 3 h in a 1 mM IPTG-containing LB-Kan medium hPUF_MT(R3→R5, R4→R5→R13H, R5→R13H): 37° C. for 3 h in a 1 mM IPTG-containing LB-Kan medium hPUF_MT(R3→R5, R4→R5→R13W, R5→R13W): 37° C. for 3 h in a 1 mM IPTG-containing LB-Kan medium hPUF_MT(R3→R5, R4→R5→R13Y, R5→R13Y): 37° C. for 3 h in a 1 mM IPTG-containing LB-Kan medium Rotoring for absorption to the resin was carried out for 3 h.

(3) Gel Shift Assay

Gel shift assay was performed by the same procedures as in Example 1.

Note that the following RNA probe was used.

```
OTS-1759:
                                    (SEQ ID NO: 31)
5'-Alexa680-CCAGAAUUGUAAAUAUUCG-Alexa680-3'

(19 mer)
```

FIG. 138 shows the results. It was found that aromatic amino acids have greater binding force than that of cationic amino acids. It was found that among aromatic amino acids, His and Tyr have the greatest binding force (H=Y>R>F=W>K).

Example 9-5: Between G-G (FIG. 139)

(1) Vector Cloning

FIGS. 140 to 145 show the amino acid sequences of hPUF_MT(R5:G_134, hPUF_MT(R5:G_13K)₃, hPUF_MT (R5:G_13F)₃, hPUF_MT(R5:G_13H)₃, hPUF_MT(R5: G_13W)₃, and hPUF_MT(R5:G_13Y)₃.

Vector cloning was performed by the same procedures as in Example 2-1.

(2) Protein Expression and Purification

Protein expression and purification were performed by the same procedures as in Example 1.

Note that protein expression induction was carried out under the following conditions. hPUF_MT(R5:G_13R)₃: 37° C. for 3 h in a 0.01 mM IPTG-containing LB-Kan medium Rotoring for absorption to the resin was carried out for 12.5 h.

hPUF_MT(R5:G_13K)₃: 37° C. for 7 h in a 1 mM IPTG-containing LB-Kan medium hPUF_MT(R5:G_13F)₃: 37° C. for 7 h in a 1 mM IPTG-containing LB-Kan medium hPUF_MT(R5:G_13H)₃: 37° C. for 7 h in a 1 mM IPTG-containing LB-Kan medium hPUF_MT(R5:G_13W)₃: 37° C. for 7 h in a 1 mM IPTG-containing LB-Kan medium hPUF_MT(R5:G_13Y)₃: 37° C. for 7 h in a 1 mM IPTG-containing LB-Kan medium Rotoring for absorption to the resin was carried out for 14 h.

(3) Gel Shift Assay

Gel shift assay was performed by the same procedures as in Example 1.

Note that the following RNA probe was used.

```
OTS-1842:
                                    (SEQ ID NO: 41)
5'-Alexa680-CCAGAAUUGUGGGUAUUCG-Alexa680-3'

(19 mer)
```

FIG. 146 shows the results. It was found that cationic amino acids have greater binding force than that of aromatic amino acids. It was found that among aromatic amino acids, Arg has the greatest binding force (R=H>K>W=Y>F).

Example 9-6: Between U—U (FIG. 147)

(1) Vector Cloning

FIGS. 148 to 153 show the amino acid sequences of hPUF_MT(R5:U_134, hPUF_MT(R5:U_13K)₃, hPUF_MT (R5:U_13F)₃, hPUF_MT(R5:U_13H)₃, hPUF_MT(R5: U_13W)₃, and hPUF_MT(R5:U_13Y)₃.

Vector cloning was performed by the same procedures as in Example 2-1.

(2) Protein Expression and Purification

Protein expression and purification were performed by the same procedures as in Example 1.

Note that protein expression induction was carried out under the following conditions. hPUF_MT(R5:U_13R)₃: 37° C. for 3 h in a 1 mM IPTG-containing LB-Kan medium Rotoring for absorption to the resin was carried out for 12.5 h.

hPUF_MT(R5:U_13K)₃: 37° C. for 3 h in a 0.1 mM IPTG-containing LB-Kan medium hPUF_MT(R5:U_13F)₃: 37° C. for 3 h in a 1 mM IPTG-containing LB-Kan medium hPUF_MT(R5:U_13H)₃: 37° C. for 3 h in a 0.1 mM IPTG-containing LB-Kan medium hPUF_MT(R5:U_13W)₃: 37° C. for 3 h in a 1 mM IPTG-containing LB-Kan medium hPUF_MT(R5:U_13Y)₃: 37° C. for 3 h in a 1 mM IPTG-containing LB-Kan medium Rotoring for absorption to the resin was carried out for 14 h.

(3) Gel Shift Assay

Gel shift assay was performed by the same procedures as in Example 1.

Note that the following RNA probe was used.

```
OTS-1841:
                                     (SEQ ID NO: 40)
5'-Alexa680-CCAGAAUUGUUUUUAUUCG-Alexa680-3'

(19 mer)
```

FIG. 154 shows the results. It was found that aromatic amino acids have greater binding forth than that of cationic amino acids. It was found that among aromatic amino acids, Trp has the greatest binding force (W=R>H>F=Y>K).

Example 9-7: Between C—C (FIG. 155)

(1) Vector Cloning

FIGS. 156 to 161 show the amino acid sequences of hPUF_MT(R5:C_134, hPUF_MT(R5:C_13K)$_3$, hPUF_MT(R5:C_13F)$_3$, hPUF_MT(R5:C_13H)$_3$, hPUF_MT(R5:C_13W)$_3$, and hPUF_MT(R5:C_13Y)$_3$.

Vector cloning was performed by the same procedures as in Example 2-1.

(2) Protein Expression and Purification

Protein expression and purification were performed by the same procedures as in Example 1.

Note that protein expression induction was carried out under the following conditions. hPUF_MT(R5:C_13R)$_3$: 20° C. for 24 h in a 1 mM IPTG-containing LB-Kan medium Rotoring for absorption to the resin was carried out for 12.5 h.

hPUF_MT(R5:C_13K)3: 30° C. for 7 h in a 0.1 mM IPTG-containing LB-Kan medium hPUF_MT(R5:C_13F)$_3$: 30° C. for 7 h in a 0.1 mM IPTG-containing LB-Kan medium hPUF_MT(R5:C_13H)$_3$: 30° C. for 7 h in a 0.1 mM IPTG-containing LB-Kan medium hPUF_MT(R5:C_13W)$_3$: 30° C. for 7 h in a 0.1 mM IPTG-containing LB-Kan medium hPUF_MT(R5:C_13Y)$_3$: 30° C. for 7 h in a 0.1 mM IPTG-containing LB-Kan medium Rotoring for absorption to the resin was carried out for 14 h.

(3) Gel Shift Assay

Gel shift assay was performed by the same procedures as in Example 1.

Note that the following RNA probe was used.

```
OTS-1843:
                                     (SEQ ID NO: 42)
5'-Alexa680-CCAGAAUUGUCCCUAUUCG-Alexa680-3'

(19 mer)
```

FIG. 162 shows the results. It was found that F is most suitable (F>H>W>R=K>Y).

The invention claimed is:

1. An RNA-binding protein having an amino acid sequence represented by R1'—R1X—R2X—(R5X or R6Y)$_L$-(R5X—R6Y)$_M$—(R5X or R6Y)$_N$—R7X—R8X—R8':
wherein
R1X represents R1, R1(S12N), R1(S12C), R1(Q16E), or R1(Q16R),
R2X represents R2, R2(N12C), R2(N12S), R2(N12S, Q16E), or R2(N12S, Q16R),
R5X represents any one of R5, R5(C12S), R5(C12N), R5(C12S, Q16E), or R5(C12S, Q16R),
R6Y represents any one of R6, R6(N12C), R6(N12S), R6(N12S, Q16E), or R6(N12S, Q16R),
R7X represents R7, R7(S12C, E16Q), R7(E16Q), R7(S12N, E16Q), or R7(E16R),
R8X represents R8, R8(N12C), R8(N12S), R8(N12S, Q16E), or R8(N12S, Q16R),
S12N represents a substitution of a 12th amino acid S with N,
S12C represents a substitution of a 12th amino acid S with C,
N12C represents a substitution of a 12th amino acid N with C,
N12S represents a substitution of a 12th amino acid N with S,
C12N represents a substitution of a 12th amino acid C with N,
C12S represents a substitution of a 12th amino acid C with S,
Q16E represents a substitution of a 16th amino acid Q with E,
Q16R represents a substitution of a 16th amino acid Q with R,
E16Q represents a substitution of a 16th amino acid E with Q,
E16R represents a substitution of a 16th amino acid E with R,
L and N each independently represent 0 or 1, and M represents an integer of 2 or more, and each repeat corresponds to the following relevant amino acid sequence:

```
                                          (SEQ ID NO: 9)
R1': GRSRLLEDFRNNRYPNLQLREIAG;

(SEQ ID NO: 1)
R1: HIMEFSQDQHGSRFIQLKLERATPAERQLVFNEILQ;

(SEQ ID NO: 2)
R2: AAYQLMVDVFGNYVIQKFFEFGSLEQKLALAERIRG;

(SEQ ID NO: 5)
R5: QVFALSTHPYGCRVIQRILEHCLPDQTLPILEELHQ;

(SEQ ID NO: 6)
R6: HTEQLVQDQYGNYVIQHVLEHGRPEDKSKIVAEIRG;

(SEQ ID NO: 7)
R7: NVLVLSQHKFASNVVEKCVTHASRTERAVLIDEVCTMNDGPHS;

(SEQ ID NO: 8)
R8: ALYTMMKDQYANYVVQKMIDVAEPGQRKIVMHKIRP;

(SEQ ID NO: 10)
R8': HIATLRKYTYGKHILAKLEKYYMKNGVDLG.
```

2. An RNA-binding protein having an amino acid sequence represented by EIRG-(R5X—R6Y)$_n$: wherein n R5Xs each independently represent R5, R5(C12N), R5(C12S, Q16E), or R5(C12S, Q16E), n R6Ys each independently represent R6, R6(N12C), R6(N12S, Q16E), or R6(N12S, Q16R), and n represents an integer of 4 to 15:

```
R5:
                                          (SEQ ID NO: 5)
QVFALSTHPYGCRVIQRILEHCLPDQTLPILEELHQ;

R5(C12N):
                                         (SEQ ID NO: 11)
QVFALSTHPYGNRVIQRILEHCLPDQTLPILEELHQ;

R5(C12S, Q16E):
                                         (SEQ ID NO: 12)
QVFALSTHPYGSRVIERILEHCLPDQTLPILEELHQ;

R5(C12S, Q16R):
                                         (SEQ ID NO: 13)
QVFALSTHPYGSRVIRRILEHCLPDQTLPILEELHQ;

R6:
                                          (SEQ ID NO: 6)
HTEQLVQDQYGNYVIQHVLEHGRPEDKSKIVAEIRG;

R6(N12C):
                                         (SEQ ID NO: 14)
HTEQLVQDQYGCYVIQHVLEHGRPEDKSKIVAEIRG;

R6(N12S, Q16E):
                                         (SEQ ID NO: 15)
HTEQLVQDQYGSYVIEHVLEHGRPEDKSKIVAEIRG;

R6(N12S, Q16R):
                                         (SEQ ID NO: 16)
HTEQLVQDQYGSYVIRHVLEHGRPEDKSKIVAEIRG.
```

3. An RNA-binding protein having an amino acid sequence represented by AFKG-(R5X—R6YZ)$_{n-1}$→R5X—R6Y, wherein n R5Xs each independently represent R5, R5(C12N), R5(C12S, Q16E), or R5(C12S, Q16E), (n−1) R6YZs each independently represent R6 (AFKG), R6(N12C) (AFKG), R6(N12S, Q16E) (AFKG), or R6(N12S, Q16R) (AFKG), R6Y represents R6, R6(N12C), R6(N12S, Q16E), or R6(N12S, Q16R), and n represents an integer of 4 to 15:

```
R5:
                                          (SEQ ID NO: 5)
QVFALSTHPYGCRVIQRILEHCLPDQTLPILEELHQ;

R5(C12N):
                                         (SEQ ID NO: 11)
QVFALSTHPYGNRVIQRILEHCLPDQTLPILEELHQ;

R5(C12S, Q16E):
                                         (SEQ ID NO: 12)
QVFALSTHPYGSRVIERILEHCLPDQTLPILEELHQ;

R5(C12S, Q16R):
                                         (SEQ ID NO: 13)
QVFALSTHPYGSRVIRRILEHCLPDQTLPILEELHQ;

R6(AFKG):
                                         (SEQ ID NO: 17)
HTEQLVQDQYGNYVIQHVLEHGRPEDKSKIVAAFKG;

R6(N12C) (AFKG):
                                         (SEQ ID NO: 18)
HTEQLVQDQYGCYVIQHVLEHGRPEDKSKIVAAFKG;

R6(N12S, Q16E) (AFKG):
                                         (SEQ ID NO: 19)
HTEQLVQDQYGSYVIEHVLEHGRPEDKSKIVAAFKG;

R6(N12S, Q16R) (AFKG):
                                         (SEQ ID NO: 20)
HTEQLVQDQYGSYVIRHVLEHGRPEDKSKIVAAFKG;
```

-continued

R6:
(SEQ ID NO: 6)
HTEQLVQDQYGNYVIQHVLEHGRPEDKSKIVAEIRG;

R6(N12C):
(SEQ ID NO: 14)
HTEQLVQDQYGCYVIQHVLEHGRPEDKSKIVAEIRG;

R6(N12S, Q16E):
(SEQ ID NO: 15)
HTEQLVQDQYGSYVIEHVLEHGRPEDKSKIVAEIRG;

R6(N12S, Q16R):
(SEQ ID NO: 16)
HTEQLVQDQYGSYVIRHVLEHGRPEDKSKIVAEIRG.

4. The protein according to claim 2, which further has R1' at the N terminus and/or R8' at the C terminus:

(SEQ ID NO: 9)
R1': GRSRLLEDFRNNRYPNLQLREIAG;

(SEQ ID NO: 10)
R8': HIATLRKYTYGKHILAKLEKYYMKNGVDLG.

5. The protein according to claim 2, which further has R1'-R1-R2 at the N terminus and/or R8-R8' at the C terminus.

(SEQ ID NO: 9)
R1': GRSRLLEDFRNNRYPNLQLREIAG;

(SEQ ID NO: 10)
R8': HIATLRKYTYGKHILAKLEKYYMKNGVDLG;

(SEQ ID NO: 1)
R1: HIMEFSQDQHGSRFIQLKLERATPAERQLVFNEILQ;

(SEQ ID NO: 2)
R2: AAYQLMVDVFGNYVIQKFFEFGSLEQKLALAERIRG;

(SEQ ID NO: 8)
R8: ALYTMMKDQYANYVVQKMIDVAEPGQRKIVMHKIRP.

6. A nucleic acid encoding the RNA-binding protein according to claim 1.

7. A recombinant expression vector including the nucleic acid according to claim 6.

8. A host cell including the recombinant expression vector according to claim 7.

9. The protein according to claim 3, which further has R1' at the N terminus and/or R8' at the C terminus:

(SEQ ID NO: 9)
R1': GRSRLLEDFRNNRYPNLQLREIAG;

(SEQ ID NO: 10)
R8': HIATLRKYTYGKHILAKLEKYYMKNGVDLG.

10. The protein according to claim 3, which further has R1'-R1-R2 at the N terminus and/or R8-R8' at the C terminus, (SEQ ID NO: 9)
R1': GRSRLLEDFRNNRYPNLQLREIAG;

(SEQ ID NO: 10)
R8': HIATLRKYTYGKHILAKLEKYYMKNGVDLG;

(SEQ ID NO: 1)
R1: HIMEFSQDQHGSRFIQLKLERATPAERQLVFNEILQ;

(SEQ ID NO: 2)
R2: AAYQLMVDVFGNYVIQKFFEFGSLEQKLALAERIRG;

(SEQ ID NO: 8)
R8: ALYTMMKDQYANYVVQKMIDVAEPGQRKIVMHKIRP.

* * * * *